(12) United States Patent
Bennett et al.

(10) Patent No.: US 8,467,875 B2
(45) Date of Patent: *Jun. 18, 2013

(54) STIMULATION OF DORSAL GENITAL NERVES TO TREAT UROLOGIC DYSFUNCTIONS

(75) Inventors: Maria E Bennett, Lyndhurst, OH (US); Julie Grill, Chapel Hill, NC (US); Tina E Lechman, Chagrin Falls, OH (US); Joseph J Mrva, Euclid, OH (US); Jonathan L Sakai, Fairview Park, OH (US); Robert B Strother, Willoughby Hills, OH (US); Geoffrey B Thrope, Shaker Heights, OH (US); Therese M Zmina, Willoughby, OH (US)

(73) Assignee: Medtronic, Inc., Minneapolis, MN (US)

( * ) Notice: Subject to any disclaimer, the term of this patent is extended or adjusted under 35 U.S.C. 154(b) by 918 days.

This patent is subject to a terminal disclaimer.

(21) Appl. No.: 11/729,333

(22) Filed: Mar. 28, 2007

(65) Prior Publication Data

US 2007/0239224 A1      Oct. 11, 2007

Related U.S. Application Data

(63) Continuation-in-part of application No. 11/149,654, filed on Jun. 10, 2005, now Pat. No. 7,565,198, and a continuation-in-part of application No. 11/595,556, filed on Nov. 10, 2006, now Pat. No. 8,086,318, which is a continuation-in-part of application No. 10/777,771, filed on Feb. 12, 2004, now Pat. No. 7,120,499.

(60) Provisional application No. 60/578,742, filed on Jun. 10, 2004.

(51) Int. Cl.
*A61N 1/36* (2006.01)

(52) U.S. Cl.
USPC ............................................................. 607/41

(58) Field of Classification Search
USPC .................................................... 607/39–41
See application file for complete search history.

(56) References Cited

U.S. PATENT DOCUMENTS

| 3,421,511 A | 1/1969 | Schwartz et al. |
| 3,654,933 A | 4/1972 | Hagfors |

(Continued)

FOREIGN PATENT DOCUMENTS

| CA | 2 121 219 | 10/1995 |
| EP | 0245547 | 8/1990 |

(Continued)

OTHER PUBLICATIONS

PCT Search Report and Written Opinion dated Sep. 9, 2009.

(Continued)

*Primary Examiner* — Carl H Layno
*Assistant Examiner* — Luther Behringer
(74) *Attorney, Agent, or Firm* — Shumaker & Sieffert, P.A.

(57) ABSTRACT

Systems and methods treat urologic dysfunctions by implanting a lead and electrode in a tissue region affecting urologic function, and implanting a pulse generator in an anterior pelvic region remote from the electrode. Bilateral stimulation of the left and/or right branches of the dorsal genital nerves using a single lead implanted in adipose or other tissue in the region at or near the pubic symphysis is able to treat urinary incontinence.

37 Claims, 28 Drawing Sheets

U.S. PATENT DOCUMENTS

| | | |
|---|---|---|
| 3,727,616 A | 4/1973 | Lenzkes |
| 3,774,618 A | 11/1973 | Avery |
| 3,807,551 A | 4/1974 | Ankney |
| 3,870,051 A | 3/1975 | Brindley |
| 3,902,501 A | 9/1975 | Citron et al. |
| 3,926,198 A | 12/1975 | Kolenik |
| 3,939,841 A | 2/1976 | Dohring et al. |
| 3,939,843 A | 2/1976 | Smyth |
| 3,941,136 A | 3/1976 | Bucalo |
| 3,943,932 A | 3/1976 | Woo |
| 3,943,938 A | 3/1976 | Wexler |
| 4,014,346 A | 3/1977 | Brownless |
| 4,106,512 A | 8/1978 | Bisping |
| 4,232,679 A | 11/1980 | Schulman |
| 4,254,775 A | 3/1981 | Langer |
| 4,257,423 A | 3/1981 | McDonald |
| 4,262,678 A | 4/1981 | Stokes |
| 4,398,545 A | 8/1983 | Wilson |
| 4,406,288 A | 9/1983 | Horwinski |
| 4,407,303 A | 10/1983 | Akerstrom |
| 4,476,868 A | 10/1984 | Thompson |
| 4,512,351 A | 4/1985 | Pohndorf |
| 4,519,404 A | 5/1985 | Fleischhacker |
| 4,566,063 A | 1/1986 | Zolnowsky et al. |
| 4,569,351 A | 2/1986 | Tang |
| 4,573,481 A | 3/1986 | Bullara |
| 4,585,005 A | 4/1986 | Lue |
| 4,585,013 A | 4/1986 | Harris |
| 4,590,689 A | 5/1986 | Rosenberg |
| 4,590,946 A | 5/1986 | Loeb |
| 4,592,360 A | 6/1986 | Lesnick |
| 4,602,624 A | 7/1986 | Naples et al. |
| 4,607,639 A | 8/1986 | Tanagho |
| 4,628,942 A | 12/1986 | Sweeney et al. |
| 4,649,936 A | 3/1987 | Ungar et al. |
| 4,658,515 A | 4/1987 | Oatman |
| 4,692,147 A | 9/1987 | Duggan |
| 4,703,755 A | 11/1987 | Tanagho |
| 4,716,888 A | 1/1988 | Wesner |
| 4,721,118 A | 1/1988 | Harris |
| 4,739,764 A | 4/1988 | Lue |
| 4,750,499 A | 6/1988 | Hoffer |
| 4,771,779 A | 9/1988 | Tanagho |
| 4,793,353 A | 12/1988 | Borkan |
| 4,835,372 A | 5/1989 | Gombrich |
| 4,881,526 A | 11/1989 | Johnson et al. |
| 4,920,979 A | 5/1990 | Bullara |
| 4,926,875 A | 5/1990 | Rabinovitz et al. |
| 4,934,368 A | 6/1990 | Lynch |
| 4,940,065 A | 7/1990 | Tanagho et al. |
| 4,987,897 A | 1/1991 | Funke |
| 4,989,617 A | 2/1991 | Memberg |
| 4,994,019 A | 2/1991 | Fernandez et al. |
| 5,083,908 A | 1/1992 | Gagnebin et al. |
| 5,095,905 A | 3/1992 | Klepinski |
| 5,113,869 A | 5/1992 | Nappholz |
| 5,144,946 A | 9/1992 | Weinberg |
| 5,154,172 A | 10/1992 | Terry |
| 5,199,428 A | 4/1993 | Obel et al. |
| 5,207,218 A | 5/1993 | Carpentier et al. |
| 5,215,086 A | 6/1993 | Terry |
| 5,222,494 A | 6/1993 | Baker |
| D337,820 S | 7/1993 | Hooper et al. |
| 5,235,980 A | 8/1993 | Varrichio et al. |
| 5,257,634 A | 11/1993 | Kroll |
| 5,265,608 A | 11/1993 | Lee et al. |
| 5,282,845 A | 2/1994 | Bush |
| 5,289,821 A | 3/1994 | Swartz |
| 5,300,107 A | 4/1994 | Stokes |
| 5,312,453 A | 5/1994 | Shelton et al. |
| 5,324,322 A | 6/1994 | Grill, Jr. et al. |
| 5,330,507 A | 7/1994 | Schwartz |
| 5,330,515 A | 7/1994 | Rutecki |
| 5,335,664 A | 8/1994 | Nigashima |
| 5,344,439 A | 9/1994 | Otten |
| 5,350,413 A | 9/1994 | Miller |
| 5,369,257 A | 11/1994 | Gibbon |
| 5,370,671 A | 12/1994 | Maurer |
| 5,382,236 A | 1/1995 | Otto et al. |
| 5,397,338 A | 3/1995 | Grey et al. |
| 5,400,784 A | 3/1995 | Durand et al. |
| 5,411,537 A | 5/1995 | Munshi |
| 5,417,719 A | 5/1995 | Hull et al. |
| 5,425,751 A | 6/1995 | Baeten et al. |
| 5,449,378 A | 9/1995 | Schouenborg |
| 5,454,840 A | 10/1995 | Krakovsky et al. |
| 5,461,256 A | 10/1995 | Yamada |
| 5,474,552 A | 12/1995 | Paiti |
| 5,476,500 A | 12/1995 | Fain |
| 5,480,416 A | 1/1996 | Garcia et al. |
| 5,480,656 A | 1/1996 | Okada et al. |
| 5,486,202 A | 1/1996 | Bradshaw |
| 5,487,756 A | 1/1996 | Kallesoe et al. |
| 5,501,703 A | 3/1996 | Holsheimer |
| 5,505,201 A | 4/1996 | Grill, Jr. et al. |
| 5,509,888 A | 4/1996 | Miller |
| 5,531,778 A | 7/1996 | Maschino et al. |
| 5,540,730 A | 7/1996 | Terry et al. |
| 5,551,849 A | 9/1996 | Christiansen |
| 5,562,717 A | 10/1996 | Tippey |
| 5,588,960 A | 12/1996 | Edwards |
| 5,607,461 A | 3/1997 | Lathrop |
| 5,609,575 A | 3/1997 | Larson et al. |
| 5,634,462 A | 6/1997 | Tyler et al. |
| 5,639,275 A | 6/1997 | Baetge et al. |
| 5,643,330 A | 7/1997 | Holscheimer et al. |
| 5,645,586 A | 7/1997 | Meltzer |
| 5,660,854 A | 8/1997 | Haynes et al. |
| 5,669,161 A | 9/1997 | Huang |
| 5,683,432 A | 11/1997 | Goedeke et al. |
| 5,683,447 A | 11/1997 | Bush |
| 5,690,693 A | 11/1997 | Wang et al. |
| 5,702,431 A | 12/1997 | Wang et al. |
| 5,707,642 A | 1/1998 | Yue |
| 5,713,939 A | 2/1998 | Nedungadi et al. |
| 5,716,384 A | 2/1998 | Snell |
| 5,722,482 A | 3/1998 | Buckley |
| 5,722,999 A | 3/1998 | Snell |
| 5,733,322 A | 3/1998 | Starkebaum |
| 5,733,937 A | 3/1998 | Thompson et al. |
| 5,741,313 A | 4/1998 | Davis et al. |
| 5,741,319 A | 4/1998 | Woloszko et al. |
| 5,752,977 A | 5/1998 | Grevious |
| 5,755,767 A | 5/1998 | Doan |
| 5,759,199 A | 6/1998 | Snell |
| 5,792,187 A | 8/1998 | Adams |
| 5,807,397 A | 9/1998 | Barreras |
| 5,824,027 A | 10/1998 | Hoffer et al. |
| 5,843,141 A | 12/1998 | Bischoff et al. |
| 5,857,968 A | 1/1999 | Benja-Athon |
| 5,861,015 A | 1/1999 | Benja-Athon |
| 5,861,016 A | 1/1999 | Swing |
| 5,899,933 A | 5/1999 | Bhadra et al. |
| 5,913,881 A * | 6/1999 | Benz et al. ..................... 607/36 |
| 5,919,220 A | 7/1999 | Stieglitz et al. |
| 5,922,015 A | 7/1999 | Schaldach |
| 5,938,584 A * | 8/1999 | Ardito et al. ..................... 600/38 |
| 5,938,596 A | 8/1999 | Woloszko et al. |
| 5,948,006 A | 9/1999 | Mann |
| 5,957,951 A | 9/1999 | Cazaux et al. |
| 5,957,958 A | 9/1999 | Schulman et al. |
| 5,984,854 A | 11/1999 | Ishikawa |
| 6,002,964 A | 12/1999 | Feler et al. |
| 6,004,662 A | 12/1999 | Buckley |
| 6,006,133 A | 12/1999 | Lessar |
| 6,015,393 A | 1/2000 | Hovland et al. |
| 6,016,451 A | 1/2000 | Sanchez-Rodarte |
| 6,026,328 A | 2/2000 | Peckham et al. |
| 6,055,456 A | 4/2000 | Gerber |
| 6,055,457 A | 4/2000 | Bonner |
| 6,061,596 A | 5/2000 | Richmond |
| 6,072,299 A | 6/2000 | Kurle et al. |
| 6,091,995 A | 7/2000 | Ingle |
| 6,092,531 A | 7/2000 | Chen |
| 6,125,645 A | 10/2000 | Horn |
| 6,126,611 A | 10/2000 | Bougeois et al. |
| 6,166,518 A | 12/2000 | Echarri et al. |

| Patent | Type | Date | Inventor |
|---|---|---|---|
| 6,169,924 | B1 | 1/2001 | Meloy et al. |
| 6,169,925 | B1 | 1/2001 | Villaseca et al. |
| 6,181,965 | B1 | 1/2001 | Loeb |
| 6,181,973 | B1 | 1/2001 | Ceron et al. |
| 6,185,452 | B1 | 2/2001 | Schulman et al. |
| 6,185,542 | B1 | 2/2001 | Schulman |
| 6,200,265 | B1 | 3/2001 | Walsh et al. |
| 6,208,894 | B1 | 3/2001 | Schulman |
| 6,210,368 | B1 | 4/2001 | Rogers |
| 6,212,431 | B1 | 4/2001 | Hahn et al. |
| 6,216,038 | B1 | 4/2001 | Hartlaub et al. |
| 6,238,423 | B1 | 5/2001 | Bardy |
| 6,240,316 | B1 | 5/2001 | Richmond |
| 6,240,317 | B1 | 5/2001 | Villaseca et al. |
| 6,249,703 | B1 | 6/2001 | Stanton |
| 6,257,906 | B1 | 7/2001 | Price et al. |
| 6,266,557 | B1 | 7/2001 | Roe |
| 6,275,737 | B1 | 8/2001 | Mann |
| 6,283,949 | B1 | 9/2001 | Roorda |
| 6,292,703 | B1 | 9/2001 | Meier et al. |
| 6,308,101 | B1 | 10/2001 | Faltys |
| 6,308,105 | B1 | 10/2001 | Duysens et al. |
| 6,319,208 | B1 | 11/2001 | Abita et al. |
| 6,319,599 | B1 | 11/2001 | Buckley |
| 6,321,124 | B1 | 11/2001 | Cigaina |
| 6,322,330 | B1 | 11/2001 | Thomas |
| 6,338,347 | B1 | 1/2002 | Chung |
| 6,345,202 | B2 | 2/2002 | Richmond |
| 6,358,202 | B1 | 3/2002 | Arent |
| 6,360,750 | B1 | 3/2002 | Gerber |
| 6,366,814 | B1 | 4/2002 | Boveja et al. |
| 6,381,496 | B1 | 4/2002 | Meadows |
| 6,409,675 | B1 | 6/2002 | Turcott |
| 6,421,566 | B1 | 7/2002 | Holsheimer |
| 6,432,037 | B1 | 8/2002 | Eini |
| 6,442,432 | B2 | 8/2002 | Lee |
| 6,442,433 | B1 | 8/2002 | Linberg |
| 6,445,955 | B1 | 9/2002 | Michelson et al. |
| 6,449,512 | B1 | 9/2002 | Boveja |
| 6,450,172 | B1 | 9/2002 | Hartlaub et al. |
| 6,453,198 | B1 | 9/2002 | Torgerson et al. |
| 6,456,866 | B1 | 9/2002 | Tyler et al. |
| 6,458,118 | B1 | 10/2002 | Lent et al. |
| 6,464,670 | B1 | 10/2002 | Mulholland |
| 6,464,672 | B1 | 10/2002 | Buckley |
| 6,471,645 | B1 | 10/2002 | Warkentin et al. |
| 6,482,154 | B1 | 11/2002 | Haubrich et al. |
| 6,485,464 | B1 | 11/2002 | Christenson et al. |
| 6,493,587 | B1 | 12/2002 | Eckmiller et al. |
| 6,493,881 | B1 | 12/2002 | Picotte |
| 6,505,074 | B2 | 1/2003 | Boveja |
| 6,505,077 | B1 | 1/2003 | Kast et al. |
| 6,510,347 | B2 | 1/2003 | Borkan |
| 6,516,227 | B1 | 2/2003 | Meadows |
| 6,535,766 | B1 | 3/2003 | Thompson et al. |
| 6,542,776 | B1 | 4/2003 | Gordon et al. |
| 6,551,290 | B1 | 4/2003 | Elsberry et al. |
| 6,553,263 | B1 | 4/2003 | Meadows et al. |
| 6,574,510 | B2 | 6/2003 | Von Arx et al. |
| 6,587,719 | B1 | 7/2003 | Barrett et al. |
| 6,591,137 | B1 | 7/2003 | Fischell et al. |
| 6,597,954 | B1 | 7/2003 | Pless et al. |
| 6,600,956 | B2 | 7/2003 | Maschino et al. |
| 6,605,094 | B1 | 8/2003 | Mann et al. |
| 6,607,500 | B2 | 8/2003 | DaSilva et al. |
| 6,609,025 | B2 | 8/2003 | Barrett et al. |
| 6,613,953 | B1 | 9/2003 | Altura |
| 6,622,037 | B2 | 9/2003 | Kasano |
| 6,622,048 | B1 | 9/2003 | Mann et al. |
| 6,641,533 | B2 | 11/2003 | Causey et al. |
| 6,643,552 | B2 | 11/2003 | Edell et al. |
| 6,650,943 | B1 | 11/2003 | Whitehurst |
| 6,652,449 | B1 | 11/2003 | Gross |
| 6,658,297 | B2 | 12/2003 | Loeb |
| 6,658,300 | B2 | 12/2003 | Gorari et al. |
| 6,660,265 | B1 | 12/2003 | Chen |
| 6,669,663 | B1 | 12/2003 | Thompson |
| 6,672,895 | B2 | 1/2004 | Scheiner |
| 6,684,109 | B1 | 1/2004 | Osypka |
| 6,687,543 | B1 | 2/2004 | Isaac |
| 6,701,188 | B2 | 3/2004 | Stroebel et al. |
| 6,721,602 | B2 | 4/2004 | Engmark et al. |
| 6,735,474 | B1 | 5/2004 | Loeb |
| 6,735,475 | B1 | 5/2004 | Whitehurst |
| 6,754,538 | B2 | 6/2004 | Linberg |
| 6,775,715 | B2 | 8/2004 | Spitaels |
| 6,804,558 | B2 | 10/2004 | Haller et al. |
| 6,836,684 | B1 | 12/2004 | Rijkhoff |
| 6,836,685 | B1 | 12/2004 | Fitz |
| 6,845,271 | B2 | 1/2005 | Fang et al. |
| 6,855,410 | B2 | 2/2005 | Buckley |
| 6,856,506 | B2 | 2/2005 | Doherty |
| 6,859,364 | B2 | 2/2005 | Yuasa et al. |
| 6,862,479 | B1 | 3/2005 | Whitehurst et al. |
| 6,862,480 | B2 | 3/2005 | Cohen |
| 6,868,288 | B2 | 3/2005 | Thompson |
| 6,885,895 | B1 | 4/2005 | Whitehurst et al. |
| 6,891,353 | B2 | 5/2005 | Tsukamoto |
| 6,895,280 | B2 | 5/2005 | Meadows et al. |
| 6,901,287 | B2 | 5/2005 | Davis et al. |
| 6,904,324 | B2 | 6/2005 | Bishay |
| 6,907,293 | B2 | 6/2005 | Grill |
| 6,907,295 | B2 | 6/2005 | Gross et al. |
| 6,920,359 | B2 | 7/2005 | Meadows |
| 6,925,330 | B2 | 8/2005 | Kleine |
| 6,928,320 | B2 | 8/2005 | King |
| 6,937,894 | B1 | 8/2005 | Isaac |
| 6,941,171 | B2 | 9/2005 | Mann |
| 6,944,497 | B2 | 9/2005 | Stypulkowski |
| 6,963,780 | B2 | 11/2005 | Ruben et al. |
| 6,974,411 | B2 | 12/2005 | Belson |
| 6,985,773 | B2 | 1/2006 | Von Arx |
| 6,990,376 | B2 | 1/2006 | Tanagho |
| 6,993,393 | B2 | 1/2006 | Von Arx et al. |
| 6,999,819 | B2 | 2/2006 | Swoyer |
| 7,031,768 | B2 | 4/2006 | Anderson et al. |
| 7,047,078 | B2 | 5/2006 | Boggs, II |
| 7,078,359 | B2 | 7/2006 | Stepanian et al. |
| 7,101,607 | B2 | 9/2006 | Mollendorf |
| 7,103,923 | B2 | 9/2006 | Picotte |
| 7,118,801 | B2 | 10/2006 | Ristic-Lehmann |
| 7,120,499 | B2 | 10/2006 | Thrope et al. |
| 7,136,695 | B2 | 11/2006 | Pless |
| 7,167,756 | B1 | 1/2007 | Torgerson et al. |
| 7,177,690 | B2 | 2/2007 | Woods et al. |
| 7,177,698 | B2 | 2/2007 | Klosterman |
| 7,187,968 | B2 | 3/2007 | Wolf |
| 7,187,983 | B2 | 3/2007 | Dahlberg et al. |
| 7,191,012 | B2 | 3/2007 | Boveja |
| 7,198,603 | B2 | 4/2007 | Penner et al. |
| 7,225,032 | B2 | 5/2007 | Schmeling et al. |
| 7,239,918 | B2 | 7/2007 | Strother et al. |
| 7,254,448 | B2 | 8/2007 | Almendinger et al. |
| 7,269,457 | B2 | 9/2007 | Shafer et al. |
| 7,280,872 | B1 | 10/2007 | Mosesov et al. |
| 7,283,867 | B2 | 10/2007 | Strother |
| 7,292,890 | B2 | 11/2007 | Whitehurst et al. |
| 7,317,947 | B2 | 1/2008 | Wahlstrand |
| 7,328,068 | B2 | 2/2008 | Spinelli |
| 7,342,793 | B2 | 3/2008 | Ristic-Lehmann |
| 7,343,202 | B2 | 3/2008 | Mrva |
| 7,369,894 | B2 | 5/2008 | Gerber |
| 7,369,897 | B2 | 5/2008 | Boveja |
| 7,376,467 | B2 | 5/2008 | Thrope |
| 7,437,193 | B2 | 10/2008 | Parramon et al. |
| 7,443,057 | B2 | 10/2008 | Nunally |
| 7,475,245 | B1 | 1/2009 | Healy et al. |
| 7,499,758 | B2 | 3/2009 | Cates |
| 7,565,198 | B2 | 7/2009 | Bennett |
| 7,734,355 | B2 | 6/2010 | Cohen et al. |
| 7,761,166 | B2 | 7/2010 | Giftakis et al. |
| 7,809,443 | B2 | 10/2010 | Giftakis et al. |
| 2001/0022719 | A1 | 9/2001 | Armitage |
| 2002/0019652 | A1 | 2/2002 | Da Silva et al. |
| 2002/0055761 | A1 | 5/2002 | Mann |
| 2002/0055779 | A1 | 5/2002 | Andrews |
| 2002/0077572 | A1 | 6/2002 | Fang et al. |
| 2002/0082665 | A1 | 6/2002 | Haller et al. |

| | | |
|---|---|---|
| 2002/0115992 A1 | 8/2002 | Utley et al. |
| 2002/0164474 A1 | 11/2002 | Buckley |
| 2003/0004434 A1 | 1/2003 | Greco et al. |
| 2003/0004533 A1 | 1/2003 | Dieck et al. |
| 2003/0004553 A1 | 1/2003 | Grill |
| 2003/0018365 A1 | 1/2003 | Loeb |
| 2003/0045919 A1 | 3/2003 | Swoyer et al. |
| 2003/0065368 A1 | 4/2003 | Van Der Hoeven |
| 2003/0074030 A1 | 4/2003 | Leyde et al. |
| 2003/0078633 A1 | 4/2003 | Firlik et al. |
| 2003/0100930 A1 | 5/2003 | Cohen |
| 2003/0114897 A1 | 6/2003 | Von Arx et al. |
| 2003/0114905 A1 | 6/2003 | Kuzma |
| 2003/0120259 A1 | 6/2003 | Mickley |
| 2003/0220673 A1 | 11/2003 | Snell |
| 2003/0236557 A1 | 12/2003 | Whitehurst et al. |
| 2004/0015205 A1* | 1/2004 | Whitehurst et al. .............. 607/48 |
| 2004/0030360 A1 | 2/2004 | Eini |
| 2004/0049240 A1 | 3/2004 | Gerber et al. |
| 2004/0073197 A1 | 4/2004 | Kim |
| 2004/0088024 A1 | 5/2004 | Firlik |
| 2004/0093093 A1 | 5/2004 | Andrews |
| 2004/0098068 A1 | 5/2004 | Carbunaru et al. |
| 2004/0111126 A1 | 6/2004 | Tanagho |
| 2004/0122477 A1 | 6/2004 | Whitehurst et al. |
| 2004/0147886 A1 | 7/2004 | Bonni |
| 2004/0150963 A1 | 8/2004 | Holmberg |
| 2004/0162594 A1 | 8/2004 | King |
| 2004/0193228 A1 | 9/2004 | Gerber |
| 2004/0209061 A1 | 10/2004 | Farnworth |
| 2005/0010259 A1 | 1/2005 | Gerber |
| 2005/0010260 A1 | 1/2005 | Gerber |
| 2005/0015117 A1 | 1/2005 | Gerber |
| 2005/0020970 A1 | 1/2005 | Gerber |
| 2005/0021008 A1 | 1/2005 | Gerber |
| 2005/0033372 A1 | 2/2005 | Gerber |
| 2005/0033373 A1 | 2/2005 | Gerber |
| 2005/0033374 A1 | 2/2005 | Gerber |
| 2005/0038491 A1 | 2/2005 | Haack |
| 2005/0055063 A1 | 3/2005 | Loeb |
| 2005/0070969 A1 | 3/2005 | Gerber |
| 2005/0080463 A1 | 4/2005 | Stahmann |
| 2005/0096709 A1 | 5/2005 | Skwarek et al. |
| 2005/0113878 A1* | 5/2005 | Gerber ............................ 607/39 |
| 2005/0131484 A1 | 6/2005 | Boveja et al. |
| 2005/0143787 A1 | 6/2005 | Boveja |
| 2005/0143789 A1 | 6/2005 | Whitehurst et al. |
| 2005/0149146 A1 | 7/2005 | Boveja |
| 2005/0175799 A1 | 8/2005 | Farnworth |
| 2005/0192526 A1 | 9/2005 | Biggs et al. |
| 2005/0209652 A1 | 9/2005 | Whitehurst et al. |
| 2005/0216069 A1 | 9/2005 | Cohen et al. |
| 2005/0222628 A1 | 10/2005 | Krakousky |
| 2005/0228451 A1 | 10/2005 | Jaax et al. |
| 2005/0261746 A1 | 11/2005 | Gross et al. |
| 2005/0278000 A1 | 12/2005 | Strother |
| 2006/0004421 A1 | 1/2006 | Bennett et al. |
| 2006/0004429 A1 | 1/2006 | Mrva et al. |
| 2006/0020297 A1 | 1/2006 | Gerber et al. |
| 2006/0025829 A1 | 2/2006 | Armstrong |
| 2006/0033720 A1 | 2/2006 | Robbins |
| 2006/0035054 A1 | 2/2006 | Stepanian et al. |
| 2006/0069415 A1 | 3/2006 | Cameron et al. |
| 2006/0095088 A1 | 5/2006 | De Ridder |
| 2006/0100673 A1 | 5/2006 | Koinzer |
| 2006/0122659 A9 | 6/2006 | Gerber |
| 2006/0122660 A1 | 6/2006 | Boveja et al. |
| 2006/0149345 A1 | 7/2006 | Boggs, II et al. |
| 2006/0155344 A1 | 7/2006 | Rezai et al. |
| 2006/0173507 A1 | 8/2006 | Mrva |
| 2006/0184208 A1 | 8/2006 | Boggs et al. |
| 2006/0195153 A1 | 8/2006 | DiUbaldi et al. |
| 2006/0205995 A1* | 9/2006 | Browning ........................ 600/29 |
| 2006/0271112 A1 | 11/2006 | Martinson et al. |
| 2007/0021801 A1 | 1/2007 | Heruth et al. |
| 2007/0021802 A1 | 1/2007 | Heruth et al. |
| 2007/0039625 A1 | 2/2007 | Heruth et al. |
| 2007/0060967 A1 | 3/2007 | Strother |
| 2007/0100411 A1 | 5/2007 | Bonde |
| 2007/0123952 A1 | 5/2007 | Strother |
| 2007/0173900 A1 | 7/2007 | Siegel et al. |
| 2007/0239224 A1 | 10/2007 | Bennett |
| 2007/0253997 A1 | 11/2007 | Giftakis et al. |
| 2007/0253998 A1 | 11/2007 | Giftakis et al. |
| 2007/0255333 A1 | 11/2007 | Giftakis et al. |
| 2007/0255341 A1 | 11/2007 | Giftakis et al. |
| 2008/0065167 A1 | 3/2008 | Boggs, II et al. |
| 2008/0071322 A1 | 3/2008 | Bennett |
| 2008/0097564 A1 | 4/2008 | Lathrop |
| 2008/0132969 A1 | 6/2008 | Bennett |
| 2008/0161874 A1 | 7/2008 | Bennett |
| 2008/0183236 A1 | 7/2008 | Gerber |

FOREIGN PATENT DOCUMENTS

| | | |
|---|---|---|
| EP | 1 468 648 | 10/2004 |
| EP | 1468648 | 10/2004 |
| EP | 1 790 304 | 5/2007 |
| EP | 1790304 | 5/2007 |
| WO | WO 00/19939 | 4/2000 |
| WO | 01/83029 | 11/2003 |
| WO | 03/092227 | 11/2003 |
| WO | 2005/122727 | 12/2005 |
| WO | WO 2005/122727 | 12/2005 |
| WO | 2006/055547 | 5/2006 |
| WO | 2006/133445 | 12/2006 |
| WO | WO 2006/133445 | 12/2006 |
| WO | 2008/054448 | 5/2008 |
| WO | WO 2005/544448 | 5/2008 |
| WO | WO 2009/58984 | 5/2009 |

OTHER PUBLICATIONS

A Breakthrough in Advanced Materials, Aspen Aerogels, Inc. (1 pg) www.aerogels.com, 2003.

Brindley, "Sacral root and hypogastric plexus stimulators and what these models tell us about autonomic actions on the bladder and urethra," Clinical Science, vol. 70 (Suppl. 14), pp. 41s-44s, 1986.

Berman et al., "Female Sexual Function and Dysfunction," Annual Meeting of American Urological Association, Inc., May 29, 2002, 33 pp.

Bolandard et al., European Society of Regional Anaesthesia and Pain Therapy, "Ilioinguinal-Iliohypogastric Block—Single Shot," 2006, 2 pp.

Chalfin, "Neural Stimulation as a Method of Controlling Prostatitis Symptoms," disclosed in 1999 Selected Abstracts from American Urological Association Annual Meeting, 2 pp.

Corbett http://crisp.cit.nih.gov/ Abstract, High-Density Liquid Crystal Polymer Cochlear Electrodes, downloaded Sep. 18, 2006, 2 pp.

Crampon et al., "Nerve Cuff Electrode with Shape Memory Alloy Armature: Design and Fabrication," Bio-Medical Materials and Engineering 12; 2002:397-410.

Crampon et al., "New Easy to Install Nerve Cuff Electrode Using Shape Memory Alloy Armature," Artificial Organs, 23(5):392-395, 1999.

Edell, David J., PhD, Boston Healthcare Research Device, Feb. 15, 2006, 3 pp.

Granitsiotis et al., "Chronic Testicular Pain: An Overview," European Urology, vol. 45, pp. 430-436, 2004.

Gillitzer et al., "Pudendal Nerve Branch Injury During Radical Perineal Prostatectomy," Journal of Urology, vol. 67, No. 2, 2006 (3 pp.).

Hruby et al., "Anatomy of pudendal nerve at urogenital diaphragm—new critical site for nerve entrapment," Journal of Urology, vol. 66, Issue 5, Nov. 2005, pp. 949-952.

Kim et al., "Surgical Management of 33 Ilioinguinal and Iliohypogastric Neuralgias at the Louisiana State University Health Sciences Center," Neurosurgery, vol. 56, No. 5, pp. 1013-1020, www.neurosurgery-online.com, May 2005.

Lamer et al., "Treatment of Iliohypogastric Neuralgia with Subcutaneous Peripheral Nerve Stimulation," Poster Abstract Form, 9th Annual Meeting, North American Neuromodulation Society, Nov. 10-12, 2005,1 p.

Levine et al., "Microsurgical Denervation of the Spermatic Cord as Primary Surgical Treatment of Chronic Orchialgia," The Journal of Urology, vol. 165, pp. 1927-1929, Jun. 2001.

Loeb et al., "Cuff Electrodes for Chronic Stimulation and Recording of Peripheral Nerve Activity," Journal of Neuroscience Methods, 64 (1996), 95-103.

Mayo Foundation for Medical Education and Research, "Urinary Incontinence," http://www.mayoclinic.com/health/urinaryincontinence/DS00404/DECTION=8, Jan. 8, 2007, 5 pp.

Mayo Foundation for Medical Education and Research, "Erectile Dysfunction," http://www.mayoclinic.com/health/erectiledysfunction/DS00162/DSECTION=7, Jan. 18, 2006 (3 pp.).

Medtronic Instruction for Use Manual, "Interstim® Therapy," Model 3080, 3092, 3886 and 3966 (32 pages) Jul. 18, 2005.

Medtronic Instruction for Use Manual, "Interstim®," Model 3080, 3092, 3886 and 3966 (36 pages) Oct. 24, 2005.

Medtronic Instruction for Use Manual, "Pisces Quad®, Compact® and Pisces Quad Plus®," Model 3487A, 3887 and 3888 (16 pages) Jan. 22, 2004.

Medtronic Instruction for Use Manual, "Interstim®," Model 4350 (40 pages) 2005.

Medtronic Instruction for Use Manual, "Interstim® Therapy," Model 3058 and 3023 (32 pages) May 5, 2006.

Medtronic Instruction for Use Manual, "Itrel®3," Model 7425 (78 pages) Jul. 12, 2005.

Medtronic Instruction for Use Manual, "Synergy™ and Synergy Versitrel™," Model 7427 and 7427V (96 pages) Oct. 30, 2003.

Medtronic Instruction for Use Manual, Model 7424 (58 pages) Sep. 1993.

Midgley, www.machinedesign.texterity.com, Vacuum-Formed Films for Fit and Function, Oct. 7, 2004, 2 pp.

Modern Plastics Worldwide, Notables: 10 waves of the future, Sample Molding in Progress, Sep. 1, 2005, 2 pp.

Murovic et al., "Surgical Management of 10 Genitofemoral Neuralgias at the Louisiana State University Health Sciences Center," Neurosurgery, vol. 56, No. 2, pp. 298-303, www.neurosurgery-online.com, Feb. 2005.

Naples et al., "A Spiral Nerve Cuff Electrode for Peripheral Nerve Stimulation," IEEE Transactions on Biomedical Engineering, vol. 35, No. 11, Nov. 1988, pp. 905-916.

NeuroControl Corp., The NeuroControl StiM System, "World's First Miniturized Multi.Channel Programmable Neuromuscular Stimulator" brochure, undated, 4 pp.

New York School of Regional Anesthesia, "Genitofemoral Block," http://www.nysora.com/techniques/genitofemoral_block/, 2006, 3 pp.

Riley, www.flipchips.com, Advanced Packaging—Wafer-level Hermetic Cavity Packaging, originally published in Advanced Packaging Magazine, May 2004, 9 pp.

Riley, www.flipchips.com, Tutorial 31—A Survey of Wafer Level Hermetic Cavity Chip Scale Packages for RF Applications, Jun. 2003, 8 pp.

Romero et al., "Neural Morphological Effects of Long-term Implantation of the Self-Sizing Spiral Cuff Nerve Electrode," Medical & Biological Engineering & Computing, 2001, vol. 39, pp. 90-100.

Sahin et al., "Spiral Nerve Cuff Electrode for Recordings of Respiratory Output," The Spiral Nerve Cuff Electrode, J. Appl. Physiol 83(1):317-322, 1997.

Sasaoka et al., "Evaluation of genitofemoral nerve block, in addition to ilioinguinal and iliohypogastric nerve block, during inguinal hernia repair in children," British Journal of Anaesthesia, vol. 94, No. 2, pp. 243-246, 2005.

Schmidt, "Technique of Pudendal Nerve Localization for Block or Stimulation," The Journal of Urology, vol. 142, pp. 1528-1531, Dec. 1989.

Sweeney et al., "A Nerve Cuff Technique for Selective Excitation of Peripheral Nerve Trunk Regions," IEEE Transactions on Biomedical Engineering, vol. 37, No. 7, Jul. 1990, pp. 706-715.

The Pain Clinic, "Peripheral Nerve Blocks," http://www.painclinic.org/treatment-peripheralnerveblocks.htm, 2006, 10 pp.

Tyler et al., "Chronic Response of the Rat Sciatic Nerve to the Flat Interface Nerve Electrode," Annals of Biomedical Engineering, vol. 31, pp. 633-642, 2003.

Uchio et al., "Cortical Evoked Responses from the Perineal Nerve," The Journal of Urology, vol. 162, pp. 1983-1986, Dec. 1999.

Vodusek et al., "Detrusor Inhibition Induced by Stimulation of Pudendal Nerve Afferents," Neurology and Urodynamics., 1986; 5:381-389.

Wallace, www.devicelink.com, MPMN, Liquid-Crystal Polymer Meets the Challenges of RF Power Packaging; The plastic air-cavity packages are hermetically sealed using a proprietary process, May 2004, 2 pp.

www.foster.miller.com, Project Examples, Packaging for Implantable Electronics, Foster-Miller, Inc. Feb. 15, 2006.

Yucel et al., "The neuroanatomy of the human scrotum:surgical ramifications," BJU International, vol. 51, pp. 393-397, 2003.

Restriction Requirement from U.S. Appl. No. 12/059,243, dated Aug. 30, 2010, 5 pp.

Response to Restriction Requirement dated Aug. 30, from U.S. Appl. No. 12/059,243, filed Sep. 29, 2010, 1 p.

Office Action from U.S. Appl. No. 12/059,243, dated Dec. 14, 2010, 10 pp.

Response to Office Action dated Dec. 14, 2010, from U.S. Appl. No. 12/059,243, filed Mar. 14, 2011, 9 pp.

Restriction Requirement from U.S. Appl. No. 11/414,509, dated Feb. 8, 2010, 7 pp.

Response to Restriction Requirement dated Feb. 8, 2010, from U.S. Appl. No. 11/414,509, filed Mar. 10, 2010, 2 pp.

Office Action from U.S. Appl. No. 11/414,509, dated Jun. 14, 2010, 11 pp.

Response to Office Action dated Jun. 14, 2010, from U.S. Appl. No. 11/414,509, filed Sep. 14, 2010, 14 pp.

Office Action from U.S. Appl. No. 11/414,509, dated Nov. 26, 2010, 9 pp.

Response to Office Action dated Nov. 26, 2010, from U.S. Appl. No. 11/414,509, filed Feb. 28, 2011, 17 pp.

Office Action from U.S. Appl. No. 12/059,243, dated Jun. 15, 2011, 8 pp.

Office Action from U.S. Appl. No. 12/059,243, dated Nov. 28, 2011, 10 pp.

Response to Office Action dated Nov. 28, 2011, from U.S. Appl. No. 12/059,243, filed Feb. 28, 2012, 4 pp.

Advisory Action for U.S. Appl. No. 12/059,243, dated Mar. 12, 2012, 3 pp.

Pre-Appeal Brief Request for Review for U.S. Appl. No. 12/059,243, dated Mar. 28, 2012, 5 pp.

Notice of Panel Decision from Pre-Appeal Brief for U.S. Appl. No. 12/059,243, dated May 30, 2012, 2 pp.

Appeal Brief for U.S. Appl. No. 12/059,243, dated Jul. 2, 2012, 14 pp.

Examiner's Answer from Appeal Brief for U.S. Appl. No. 12/059,243, dated Sep. 4, 2012, 8 pp.

Office Action from U.S. Appl. No. 11/891,214, dated May 16, 2011, 10 pp.

Office Action from U.S. Appl. No. 11/981,424, dated Dec. 7, 2011, 14 pp.

Office Action from U.S. Appl. No. 11/981,113, dated Nov. 16, 2011, 12 pp.

Response to Office Action dated Nov. 6, 2012, from U.S. Appl. No. 13/031,482, filed Feb. 6, 2013, 15 pp.

U.S. Appl. No. 60/486,573, filed Jul. 2003, Loeb.

"Neuromodulation of the lower unirary tract", Experimental Physiology, 84, 149-160. Craggs, M. & McFarlane, J.P. (1999).

"Detection and inhibition of hyper-reflexia-like bladder contractions in the cat by sacral nerve root recording and electrical stimulation," Neuroroloty and Urodynamics, 20(2), 215-230 Jezemik S., Grill, W.M. & Sinkjaer, T. (2001).

"Prolonged enhancement of the micturition reflex in the cat by repetitive stimulation of bladder afferents,", Journal of Physiology, 517.2, 599-605; Jiang, C-H. & Lindstrom, S. (1999).

"Self-controlled dorsal penile nerve stimulation to inhibit bladder hyperreflexia in incomplete spinal injury: A case report", Arch. Phys. Med. Rehabil. 83, 273-7, Lee, Y.h. & Creasey, G.H. (2002).

"Detrusor inhibition induced from mechanical stimulation of the anal region and from electrical stimulation of pudendal nerve afferents," Investigate Urology, 5, 374-8; Sundin, T., Carlsson, C-A & Kock, N.G., (1974).

"Bladder inhibition by penile nerve stimulation in spinal cord injury patients", The Journal of Urology, 147(1), 100-3; Wheeler et al. (1992).

"Aberrant reflexes and function of the pelvic organs following spinal cord injury in man,", M.D. Craggs et al., Autonomic Neurosicence: Basic & Clinical; 126-127 (2006) 355-370.

"Emerging Clinical Applications of Electrical Stimulation: Opportunities for Restoration of Function", Grill et al.; Journal of Rehabilitation Research and Development, vol. 38, No. 6, Nov./Dec. 2001.

2005 Biocontrol Medical Article: "Lower Unirary Tract", Israel Nissenkorn and Peter R. De Jong, pp. 1253-1258.

Mar. 2002 Physician's Manual: Cybernonics Model 201 NeuroCybernetic Prothesis (NCP) Programming Wand, pp. 1-18.

Aug. 2002 Physician's Manual: Cyberonics Model Models 100 and 101 NeuroCybernetic Prosthesis System, NCP Pulse Generator, pp. 1-92.

2005 Advanced Neuromodulation Systems, Inc.; ANS Medical—Determining Chronic Pain Causes and Treatments; Website: http://www.ans-medical.com/medicalprofessional/physician/rechargeableipgsystems.cfm.

Sweeney, J.D., D.A. Ksienski, J.T. Mortimer, (1990), A nerve cuff technique for selective excitation of peripheral nerve trunk regions, IEEE Trans. Biomed. Eng. 37:706-715.

2004 Advanced Bionics Corporation Summary of Safety and Effectiveness, pp. 1-18.

2004 Advanded Bionics Corporation Physician Implant Manual.

2005 Cyberonics VNS Therapy website: http://www.vnstherapy.com/Epilepsy;ncp/forsurgeons/implantedcomponents.aspx.

2004 Advanced Bionics Corporation Patient System Handbook.

Oct. 2001 Advanced Neuromodulation System, Inc. ANS Genesis Neurostimulation System Programmer User's Guide.

Nov. 21, 2001 Advaned Neuromodulation Systems, Inc. (ANS) Summary of Safety and Effectiveness Data, pp. 1-17.

Starbuck, D.L. Mortimer, J.T. Sheally C.N., Reswick, J.B. (1966) An implantable electrodes system for nerve stimulation, Proc. $19^{th}$ Ann. Conf. on Eng. in Med. and Biol. 8:38.

Grill, W.M., J.T. Mortimer (1996) Quantification of recruitment properties of multiple contact cuff electodes. IEEE Transactions on Rehabilitation Engineering 4(2):49-62.

Veraart, C., W.M. Grill, J.T. Mortimer (1993) Selective control of muscle activation with a multipolar nerve cuff electrode, IEEE Trans. Biomed. Engineering 40:640-653.

Grill, W.M. (2001), "Selective Activation of the Nervous System for Motor System Neural Prostheses" in Intelligent Systems and Technologies in Rehabilitation Engineering, H.-N.L. Teodorescu, LC. Jain, Eds. CRC Press, 211-241.

McNeal, D.R., B.R. Bowman (1985) Selective activation of muscles using peripheral nerve electrodes, Med. and Biol. Eng. and Comp. 23:249-253.

Starbuck, D.L. (1965) Myo-electric control of paralyzed muscles. IEEE Transactions on Biomedical Engineering 12(3):169-172, Jul.-Oct.

Caldwell, C. (1971), Multielectrode Electrical Stimulation of Nerve, in Development of Orthotic Systems Using Functional Electrical Stimulation and Myoelectric Control, Final Report Project #19-P-58391-F-01, University of Lubijana, Faculty of Electrical Engineering, Lubijana, Yugoslavia.

McNeal, D.R. (1974) Selective stimulation, in Annual reports of Progress, Rehabilitation Engineering Center, Ranchio Los Amigos Hospital, Downey, CA pp. 24-25.

Wheeler et al., "Management of Incontienent SCI patients with penile stimulation; preliminary results," J. Am. Paraplegia Soc. Apr. 1994; 17(2):55-9.

Bemelmans, Bart L. H., "Neuromodulation by Implant for Treating Lower Urinary Tract Symptoms and Dysfunction", Eur. Urol. Aug. 1999 36(2):81-91.

Bower WF et al., "A Urodynamic Study of Surface Neuromodulation Versus Sham in Detrusor Instability and Sensory Urgency", J. Urology 1998: 160:2133-2136.

Brindley, G. et al., "Sacral Anterior Root Stimulators for Bladder Control in Paraplegia", Paraplegia 1982: 20(6):365-381.

Dalmose AL et al., "Conditional Stimulation of the Dorsal Penile/Clitoral Nerve", Neurourol. Urodyn 2003:22(2):130-37.

Fossberg E. et al., "Maximal Electrical Stimulation in the Treatment of Unstable Detrusor and Urge Incontinence", Eur. Urol. 1990; 18:120-123.

Gustafson, K. et al., "Catheter Based Method to Activate Urethral Sensory Nerve Fibers", J. Urol 2003 170(1):126-129.

Gustafson, K. et al., "A Urethral Afferent Mediated Excitatory Bldder Reflex Exists in Humans", Neurosci. Letter 2004:360(1-2)9-12.

Jezernik S. et al., "Electrical Stimulation for the Treatment of Bladder Dysfunction: Current Status and Future Possibilities", Nuerol Res 2002; 24:413-30.

Jiang C et al., "Prolonged Increase in Micturition Threshold Volume by Anogenttal Afferent Stimulation in the Rat", Br J Urol 1998; 82(3); 398-403.

Juenemann K et al., "Clinical Significance of Sacral and Pudendal Nerve Anatomy", J Orol 1988: 139(1)74-80.

Madersbacher, H., "Urinary Urge and Reflex Incontinence", Urologe A 1991: 30(4):215-222 (Abstract only—Article in German).

Mazieres, L. et al., "The C Fibre Reflex of the Cat Urinary Bladder", J. Physiol. 1998; 513 (Pt 2):531-541.

Mazieres, L. et al., "Bladder Paraymphathetic Response to Electrical Stimulation of Urethral Afferents in the Cat", Nuerol Urodynam 1997; 16:471-472.

Nakaumra M. et al., "Bladder Inhibition by Penile electrical Stimulation", Br J. Urol 1984:56:413-415.

Oliver S. et al., "Measuring the Sensations of Urge and Bladder Filling During Cystometry in Urge Incontinence and the Effects of Neuromodulation", Neurourol Urodyn 2003; 22:7-16.

Previnaire JG et al., "Shore-Term Effect of Pudendal Nerve Electrical Stimulation on Detrusor Hyperreflexia in Spinal Cord Injury Patients; Importance of Current Strength", Paraplegia 1996; 34:95-99.

Rijkhoff N. et al., "Urinary Bladder Control by electrical Stimulation: Review of electrical Stimulation Techniquies in Spinal Cord Injury", Nuerourol Urodyn 1997; 16(1) 39-53.

Schmidt, RA, Applications of Nuerostimulation in Urology:, 1988: 7:585-92.

Spinelli, M. et al., "A New Minimally Invasive Procedure for Pudentdal Nerve Stimulation to Treat Neurogenic Bladder: Description of the Method and Preliminary Data", Nuerorol and Urodyn. 2005; 24:305-309.

Talaat, M., "Afferent Impluses in the Nerves Supplying the Urinary Bladder", Journal of Physiology 1937: 89:1-13.

Tanagho EA et al., "Electrical Stimulation in the Clinical Management of the Neurogenic bladder", J. urol. 1988; 140-1331-1339.

Yang C. et al., Peripheral Distribution of the Human Dorsal Nerve of the Penis, J. Urol 1998: 159(6):1912-6, discussion 1916.

PCT Search Report and Written Opinion dated Feb. 25, 2009.

Office Action from Canadian patent application No. 2,608,017, dated Jan. 16, 2013, 3 pp.

Office Action from U.S. Appl. No. 11/414,509, dated Mar. 15, 2013, 11 pp.

* cited by examiner

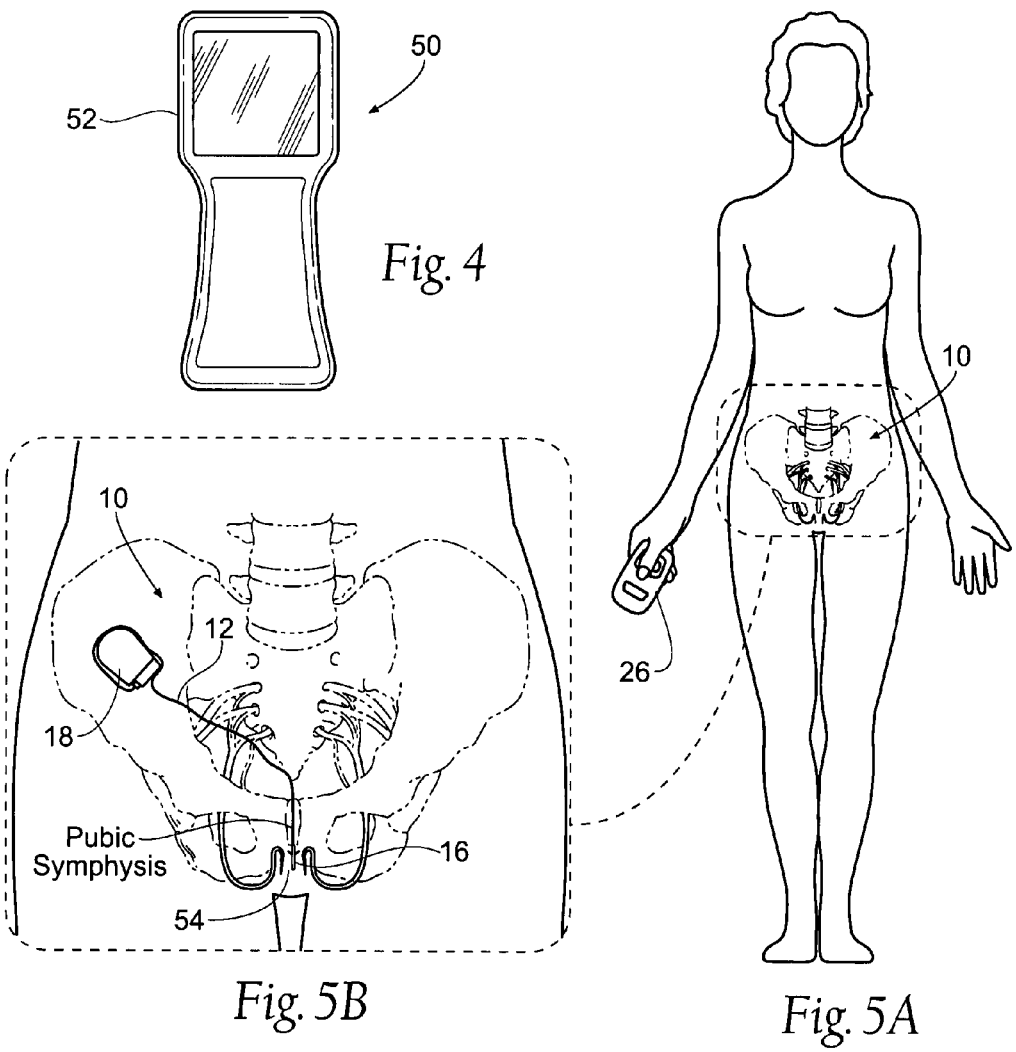
Fig. 4
Fig. 5B
Fig. 5A
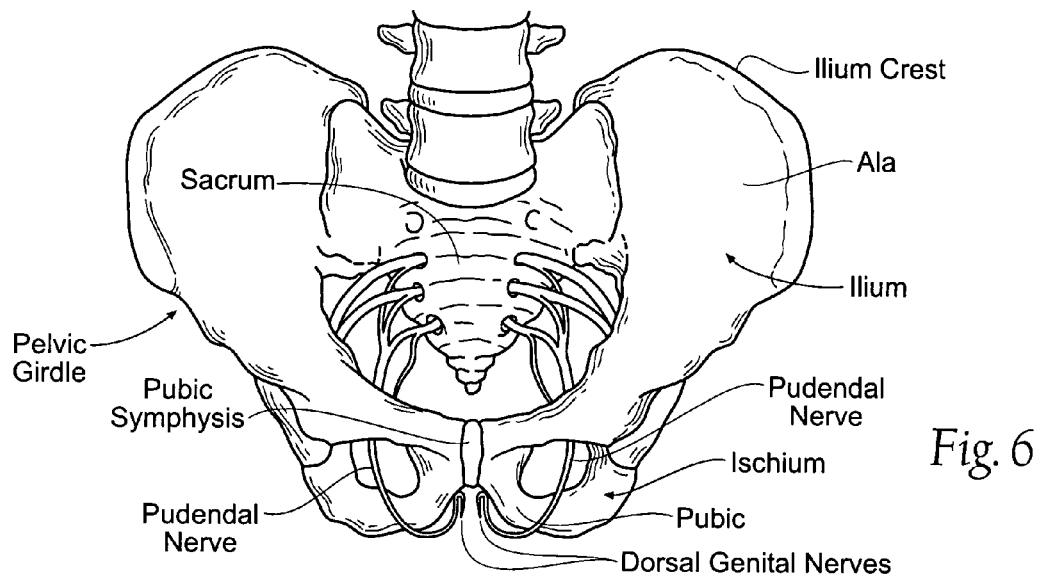
Fig. 6

STIMULATION OF DORSAL GENITAL NERVES TO TREAT UROLOGIC DYSFUNCTIONS

RELATED APPLICATIONS

This application is a continuation-in-part of U.S. patent application Ser. No. 11/149,654, now issued as U.S. Pat. No. 7,565,198 filed Jun. 10, 2005, and entitled "Systems and Methods for Bilateral Stimulation of Left and Right Branches of the Dorsal Genital Nerves to Treat Dysfunctions Such as Urinary Incontinence," which claims the benefit of U.S. Provisional Patent Application Ser. No. 60/578,742, filed Jun. 10, 2004, and entitled "Systems and Methods for Bilateral Stimulation of Left and Right Branches of the Dorsal Genital Nerves to Treat Dysfunctions, Such as Urinary Incontinence."

This application is also a continuation-in-part of U.S. patent application Ser. No. 11/595,556, filed Nov. 10, 2006, now U.S. Pat. No. 8,086,318 and entitled "Portable Assemblies, Systems, and Methods for Providing Functional or Therapeutic Neurostimulation," which is a continuation-in-part of U.S. patent application Ser. No. 10/777,771, filed Feb. 12, 2004, (now U.S. Pat. No. 7,120,499), and entitled "Portable Percutaneous Assemblies, Systems, and Methods for Providing Highly Selective Functional or Therapeutic Neurostimulation." Each of the preceding applications is incorporated herein by reference.

STATEMENT REGARDING FEDERALLY SPONSORED RESEARCH

This invention was made with government support under grant numbers 1R43AG021851-01 awarded by the National Institutes of Health, through the National Institute of Aging, and 1R43AG022292-01 awarded by the National Institutes of Health, through the National Institute of Aging. The Government has certain rights in the invention.

FIELD OF THE INVENTION

This invention relates to systems and methods for stimulating nerves and muscles in animals, including humans.

BACKGROUND OF THE INVENTION

Many millions of people throughout the world suffer from a variety of urologic dysfunctions. Urologic dysfunctions are generally understood to include indications such as urinary incontinence, fecal incontinence, micturition/retention, defecation/constipation, sexual dysfunctions, pelvic floor muscle activity, and pelvic pain.

As one example, thirteen million Americans suffer from various types of urinary incontinence. The most prevalent type of urinary incontinence (22% of the total) is called Stress Incontinence (SUI). SUI is characterized by the unintended emission of urine during everyday activities and events, such as laughing, coughing, sneezing, exercising, or lifting. These activities and events cause an increase in bladder pressure resulting in loss of urine due to inadequate contraction of the sphincter muscle around the outlet of the bladder.

Another prevalent type of urinary incontinence (18% of the total) is called Urinary Urge Incontinence (UUI). UUI is characterized by a strong desire to urinate, followed by involuntary contractions of the bladder. Because the bladder actually contracts, urine is released quickly, making it impossible for urge incontinence sufferers to predict when the problem will occur. UUI can be caused by infections, sphincter disorders, or nervous system disorders that affect the bladder.

Many people (47% of the total) encounter a combination of bladder control disorders.

Damage to the bladder, urethra, periurethral muscles and sphincters, nerves, and accessory organs can be experienced by women during childbirth or hysterectomy. This damage can lead to urinary incontinence. Prostate problems can lead to urinary incontinence in men. The number of people suffering from urinary incontinence is on the rise as the population ages.

Various treatment modalities for urinary incontinence have been developed. These modalities typically involve drugs, surgery, or both. Disposable pads can also used, not to treat the disorder, but to deal with its consequences.

Pharmocotherapy (with and without attendant behavioral therapy) appears to moderate the incidence of urinary incontinence episodes, but not eliminate them. Drug therapy alone can lead to a reduction of incontinence episodes after eight weeks by about 73%. When combined with behavioral therapy, the reduction after eight weeks is about 84% (Burgio et al, JAGS. 2000; 48:370-374). However, others have questioned the clinical significance of the results, noting that the differences in outcomes using anticholinergic drugs and placebo were small, apart from the increased rate of dry mouth in patients receiving active treatment (Herbison P, Hay-Smith J, Ellis J, Moore K, BMJ 2003; 326:841).

One present surgical modality involves the posterior installation by a percutaneous needle of electrodes through the muscles and ligaments over the S3 spinal foramen near the right or left sacral nerve roots (INTERSTIM® Treatment, Medtronic). The electrodes are connected to a remote neurostimulator pulse generator implanted in a subcutaneous pocket on the right hip to provide unilateral spinal nerve stimulation. This surgical procedure near the spine is complex and requires the skills of specialized medical personnel. Furthermore, in terms of outcomes, the modality has demonstrated limited effectiveness. For people suffering from UUI, less than 50% have remained dry following the surgical procedure. In terms of frequency of incontinence episodes, less than 67% of people undergoing the surgical procedure reduced the number of voids by greater than 50%, and less than 69% reduced the number of voids to normal levels (4 to 7 per day). This modality has also demonstrated limited reliability. Fifty-two percent (52%) of people undergoing this surgical procedure have experienced therapy-related adverse events, and of these 54% required hospitalization or surgery to resolve the issue. Many (33%) require surgical revisions.

It has been reported that 64% of people undergoing some form of treatment for urinary incontinence are not satisfied with their current treatment modality (National Association for Incontinence, 1988).

A recently proposed alternative surgical modality (Advanced Bionics Corporation) entails the implantation through a 12 gauge hypodermic needle of an integrated neurostimulator and bi-polar electrode 16 assembly (called the BION® System) through the perineum into tissue near the pudendal nerve on the left side adjacent the ischial spine. See, e.g., Mann et al, Published Patent Application US2002/0055761. The clinical effectiveness of this modality is not known.

Stimulation of a target nerve N, such as the dorsal nerve of the penis (DNP) afferents activates spinal circuitry that coordinates efferent activity in the cavernous nerve (CN), increasing filling via dilation of penile arteries, and efferent activity in the pudendal nerve (PN), preventing leakage via occlusion of penile veins, producing a sustained reflex erection (see FIG. 1).

As an additional example, Erectile Dysfunction (ED) is often a result of a combination of psychological and organic factors, but it is thought to be purely psychological in origin in less than 30% of the cases. Organic factors can include complications from neurologic diseases (stroke, multiple sclerosis, Alzheimer's disease, brain or spinal tumors), chronic renal failure, prostate cancer, diabetes, trauma, surgery, medications, and abnormal structure. However, most cases of ED are associated with vascular diseases. An erection cannot be sustained without sufficient blood flow into and entrapment within the erectile bodies of the penis, and vascular related ED can be due to a malfunction of either the arterial or the venous system.

Stimulation of a target nerve or nerves (generally the afferents), such as the cavernous nerves, pudendal nerves, perineal nerves, pelvic splanchnic nerves, dorsal genital nerves, hypogastric nerves, sacral nerve roots, and/or lumbar nerve roots, activates spinal circuitry that coordinates efferent activity in the cavernous nerve (CN), increasing filling via dilation of penile arteries, and efferent activity in the pudendal nerve (PN), preventing leakage via occlusion of penile veins, producing a sustained reflex erection.

There remains a need for systems and methods that can treat urologic dysfunctions, such as urinary incontinence, as a first line of treatment and for those who have not responded to conventional therapies, in a straightforward manner, without requiring drug therapy and complicated surgical procedures.

SUMMARY OF THE INVENTION

One aspect of the invention provides systems and methods for the treatment of urologic dysfunctions by the stimulation of the left and/or right branches of the dorsal genital nerves, the pudendal nerve and/or its branches, and/or the perineal nerves, and/or its branches, using a lead implanted in adipose or other tissue in the region at or near the pubic symphysis.

The left and right dorsal genital (clitoral or penile) nerves are afferent branches of the pudendal nerve that carry sensory information from the clitoris (or glans of the penis). In one embodiment, the systems and methods will stimulate specifically and directly this purely sensory nerve that has a consistent inhibitory effect on reflex bladder contraction. This differs from other electrical stimulation approaches to treat urinary incontinence, which apply electrical stimulation to the mixed (sensory and motor) sacral and pudendal nerve bundles.

Another aspect of the invention provides systems and methods for treating urologic dysfunctions. The systems and methods include providing a pulse generator, providing a lead comprising a proximal portion and a distal portion, the distal portion including at least one stimulation electrode, creating a first incision near-midline over the pubic symphysis, inserting the distal portion of the lead through the first incision to position the at least one stimulation electrode at a target site between the pubic symphysis and the clitoris of a female or the base of the penis of a male, creating a second incision remote from the first incision, tunneling the proximal portion of the lead between the first incision and the second incision, coupling the lead to the pulse generator, and operating the pulse generator to convey stimulation waveforms treat the urologic dysfunction. The pulse generator may be implanted in the second incision. The second incision may be located in an anterior pelvic region.

The urologic dysfunctions can include urinary incontinence, fecal incontinence, micturition/retention, defecation/constipation, sexual dysfunctions, pelvic floor muscle activity, and pelvic pain.

Creating the first incision may further include advancing a sleeve and needle percutaneously about five centimeters to about seven centimeters into the target site to position the needle, coupling the needle to a test stimulator, and applying stimulation waveforms through the tip of the needle concurrent with positioning of the needle.

In one aspect, the stimulation electrode is sized and configured to be implanted in adipose tissue. The stimulation waveforms conveyed to the at least one stimulation electrode affect bilateral stimulation of the left and right branches of the dorsal genital nerves.

In another aspect, the distal portion of the lead includes at least one visual marker. The distal portion of the lead may also include flexible anchoring structure comprising an array of expandable shovel-like paddles. The shovel-like paddles define a scalloped shape.

Yet another aspect of the invention provides systems and methods for treating urologic dysfunctions. The systems and methods comprise implanting a stimulation electrode in tissue at or near a pubic symphysis, implanting a pulse generator at a location remote from the pubic symphysis, coupling the pulse generator to the stimulation electrode, and applying stimulation waveforms to the stimulation electrode to achieve stimulation of left and/or right branches of the dorsal genital nerves. Each implanting step may be performed without fluoroscopy and the method may be performed without urodynamics.

In one aspect, the stimulation electrode further comprises a lead comprising a proximal portion and a distal portion, the distal portion including the stimulation electrode and at least on visual marker, and implanting the stimulation electrode further includes visually observing the lead marker for desired electrode placement. The physician may request feedback from the patient about sensations felt during the lead implant as a result of applying stimulation waveforms.

An additional aspect of the invention provides systems and methods for treating urologic dysfunctions. The systems and methods comprise a lead comprising a proximal portion and a distal portion, the distal portion including at least one stimulation electrode and at least one visual marker, the stimulation electrode being sized and configured to be implanted near a nerve at a target site between the pubic symphysis and the clitoris of a female or the base of the penis of a male, a hand-held test stimulator adapted to couple to the lead to convey electrical stimulation waveforms through the lead to test the placement of the stimulation electrode, an external pulse generator sized and configured to convey electrical stimulation waveforms through the lead, the external pulse generator being used on a temporary basis to evaluate if an individual is a suitable candidate for extended placement of an implantable pulse generator, a percutaneous extension cable including a proximal portion and a distal portion, the proximal portion including an IS-1 connector for connection to the proximal portion of the lead 12, the distal portion including a touch-proof connector to couple either directly or indirectly to the external pulse generator, an implantable pulse generator adapted to convey electrical stimulation waveforms through the lead, the implantable pulse generator sized and configured to be implanted in an anterior pelvic region remote from the at least one stimulation electrode, the implantable pulse generator to be implanted after use of the external pulse generator, and a programmer for programming and/or interrogating the implantable pulse generator using transcutaneous communication circuitry.

In one aspect, conveying electrical stimulation waveforms includes operating the external pulse generator and the implantable pulse generator to convey electrical stimulation waveforms through the lead and to the stimulation electrode to achieve selective stimulation of the nerve to treat the urologic dysfunction. The nerves to be stimulated may include one or more of the left and/or right branches of the dorsal genital nerves, the pudendal nerve and/or its branches, the perineal nerves, and/or its branches, the urethral nerves, and/or its branches, and/or the sacral nerve roots.

Another aspect of the invention provides families of functional kits that consolidate for use systems and methods that can be implanted in tissue in the region at or near the pubic symphysis, together with instructions for implanting and operating such systems and apparatus to treat urinary incontinence by the stimulation of the left and/or right branches of the dorsal genital nerves.

Another aspect of the invention provides a neuromuscular stimulation system comprising at least one electrically conductive surface sized and configured for implantation in a targeted neural or muscular tissue region affecting urologic function, a lead electrically coupled to the electrically conductive surface, the lead sized and configured to be positioned subcutaneous a tissue surface, an implantable pulse generator sized and configured to be coupled to the lead and positioned subcutaneous to a tissue surface in an anterior pelvic region remote from the at least one electrically conductive surface, the implantable pulse generator comprising a case having a size between about 5 mm and about 10 mm thick, between about 15 mm and about 40 mm wide, and between about 40 mm and about 60 mm long, and the implantable pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator.

Yet another aspect of the invention provides a neuromuscular stimulation system comprising at least one electrically conductive surface sized and configured for implantation in a targeted neural or muscular tissue region affecting urologic function, a lead electrically coupled to the electrically conductive surface, the lead sized and configured to be positioned subcutaneous a tissue surface, an implantable pulse generator comprising a case sized and configured to be coupled to the lead and positioned subcutaneous to a tissue surface in an anterior pelvic region remote from the at least one electrically conductive surface, the implantable pulse generator being sized and configured for implanting in subcutaneous tissue at an implant depth of between about 0.5 cm and about 1.5 cm, and the implantable pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator.

Yet another aspect of the invention provides a method comprising providing at least one electrically conductive surface sized and configured for implantation in a targeted neural or muscular tissue region affecting urologic function, the at least one electrically conductive surface including a lead electrically coupled to the electrically conductive surface, the lead sized and configured to be positioned subcutaneous a tissue surface, providing an implantable pulse generator sized and configured to be positioned subcutaneous to a tissue surface in an anterior pelvic region remote from the at least one electrically conductive surface, the implantable pulse generator comprising a case having a size between about 5 mm and about 10 mm thick, between about 15 mm and about 40 mm wide, and between about 40 mm and about 60 mm long, and the implantable pulse generator comprising non-inductive wireless telemetry circuitry using VHF/UHF signals, the non-inductive wireless telemetry circuitry being functional at a distance as far as arm's reach away from the patient, and being adapted for programming and interrogation of the implantable pulse generator, implanting the at least one electrically conductive surface in a targeted neural or muscular tissue region affecting urologic function, implanting the lead in subcutaneous tissue, implanting the pulse generator in an anterior pelvic region remote from the at least one electrically conductive surface, coupling the pulse generator to the lead implanted in subcutaneous tissue, and operating the pulse generator to apply neuromuscular stimulation pulses to the at least one electrically conductive surface to treat the urologic function. The method may further include programming and/or interrogating the implantable pulse generator using the non-inductive wireless telemetry circuitry.

Another aspect of the invention provides a method comprising providing a stimulation electrode assembly comprising an elongated lead sized and configured to be implanted in adipose tissue, the lead including an electrically conductive portion to apply electrical stimulation to nerve tissue innervating the adipose tissue, and at least one expandable anchoring structure deployable from the lead to engage adipose tissue and resist dislodgment and/or migration of the electrically conductive portion within adipose tissue, selecting within the adipose tissue an adipose tissue region at or near a pubic symphysis innervated by a nerve affecting urinary function, implanting the electrically conductive portion and at least one expandable anchoring structure in the selected adipose tissue region, with the expandable anchoring structure deploying and engaging adipose tissue to resist dislodgment and/or migration of the electrically conductive portion within the selected adipose tissue region, and conveying electrical stimulation waveforms through the stimulation electrode assembly to achieve selective stimulation of the nerve to affect urinary function.

An aspect of the invention may include the expandable anchoring structure comprises an array of circumferentially spaced-apart, radiating tines, and wherein implanting the electrically conductive portion and the expandable anchoring structure in the selected adipose tissue region includes placing the array of circumferentially spaced-apart, radiating tines in a collapsed condition, implanting the electrically conductive portion and the array of circumferentially spaced-apart, radiating tines in the selected adipose tissue region, and expanding the array of circumferentially spaced-apart, radiating tines into the adipose tissue to resist dislodgment and/or migration of the electrically conductive portion within the selected adipose tissue region.

In one embodiment, the selected adipose tissue region is innervated by a left and/or right branch of the dorsal genital nerve. Implanting the electrically conductive portion and at least one expandable anchoring structure in the selected adipose tissue region may include placing the expandable anchoring structure in a collapsed condition, implanting the electrically conductive portion and the expandable anchoring structure in the selected adipose tissue region, and expanding the anchoring structure into the adipose tissue to resist dislodgment and/or migration of the electrically conductive portion within the selected adipose tissue region. The expandable anchoring structure, when in the expanded condition, assumes an open, proximal-pointing configuration that resists proximal passage of the lead through adipose tissue in response to a pulling force that is less than or equal to a threshold axial force level. The open, proximal-pointing configuration yields to permit proximal passage of the lead through adipose tissue in response to a pulling force that is greater than the threshold axial force level.

An aspect of the invention may include providing a sleeve having an interior bore sized and configured to create percutaneous access to adipose tissue, and implanting the electrically conductive portion and at least one expandable anchoring structure in the selected adipose tissue region includes passing the electrically conductive portion and at least one expandable anchoring structure through the interior bore of the sleeve, the interior bore of the sleeve retaining the expandable anchoring structure in the collapsed condition to accommodate passage of the electrically conductive portion and the expandable anchoring structure through the interior bore into the selected adipose tissue region. The expandable anchoring structure may be normally biased toward the expanded condition.

An additional aspect of the invention may include providing a sleeve having an interior bore sized and configured to create percutaneous access to adipose tissue, wherein implanting the electrically conductive portion and at least one expandable anchoring structure in the selected adipose tissue region includes passing the electrically conductive portion and at least one expandable anchoring structure through the interior bore of the sleeve, the interior bore of the sleeve retaining the expandable anchoring structure in the collapsed condition to accommodate passing of the electrically conductive portion and the expandable anchoring structure through the interior bore into the selected adipose tissue region, and wherein upon passing the electrically conductive portion and the expandable anchoring structure into the adipose tissue region, the expandable anchoring structure returns toward the normally biased expanded condition.

Another aspect of the invention may include providing an implantable pulse generator sized and configured to be positioned subcutaneous to a tissue surface in an anterior pelvic region remote from the at least one electrically conductive portion, implanting the implantable pulse generator in an anterior pelvic region remote from the at least one electrically conductive surface, coupling the implantable pulse generator to the stimulation electrode assembly, and wherein conveying electrical stimulation waveforms includes operating the implantable pulse generator to convey electrical stimulation waveforms through the stimulation electrode assembly to achieve selective stimulation of the nerve to affect urinary function. Programming and/or interrogating the implantable pulse generator using transcutaneous communication circuitry may also be included.

The invention may further include providing an external pulse generator sized and configured to convey electrical stimulation waveforms through the stimulation electrode assembly, coupling the external pulse generator to the stimulation electrode assembly, and wherein conveying electrical stimulation waveforms includes operating the external pulse generator to convey electrical stimulation waveforms through the stimulation electrode assembly to achieve selective stimulation of the nerve to affect urinary function.

Another aspect of the invention may include providing an implantable pulse generator sized and configured to be positioned subcutaneous to a tissue surface in an anterior pelvic region remote from the at least one electrically conductive portion, uncoupling the stimulation electrode assembly from the external pulse generator and coupling the implantable pulse generator to the stimulation electrode assembly, implanting the pulse generator in an anterior pelvic region remote from the at least one electrically conductive portion, and wherein conveying electrical stimulation waveforms includes operating the implantable pulse generator to convey electrical stimulation waveforms through the stimulation electrode assembly to achieve selective stimulation of the nerve to affect urinary function.

Other features and advantages of the inventions are set forth in the following specification and attached drawings.

BRIEF DESCRIPTION OF THE DRAWINGS

FIG. 4 is a plane view of a clinical programmer that can be used in conjunction with the system shown in FIG. 1A.

FIGS. 5A and 5B are anterior anatomic views of the system shown in FIGS. 1A and 1B after implantation in an adipose tissue region at or near the pubic symphysis.

FIG. 6 is an anterior anatomic view of the pelvic girdle in a human.

FIG. 38 is an anterior anatomic view of the system shown in FIG. 1A after implantation, showing the use of the clinical programmer shown in FIG. 4 to program or test the system.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with the treatment of urologic dysfunctions. In one embodiment, urinary incontinence is treated by the bilateral stimulation of the left and/or right branches of the dorsal genital nerves using a single lead implanted in adipose or other tissue in the region at or near the pubic symphysis. That is because the features and advantages of the invention are well suited for this purpose. Still, it should be appreciated that the various aspects of the invention can be applied in other forms and in other locations in the body to achieve other objectives as well.

I. System Overview

A. The Implant System

Figure 1A:
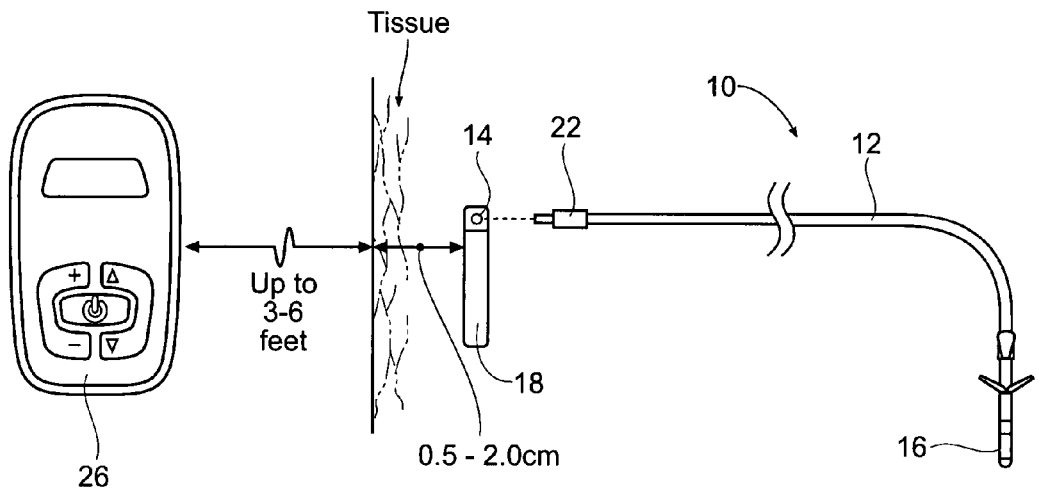
FIG. 1A is a plane view of an implant system for treating urinary incontinence in humans.
Figure 1B:
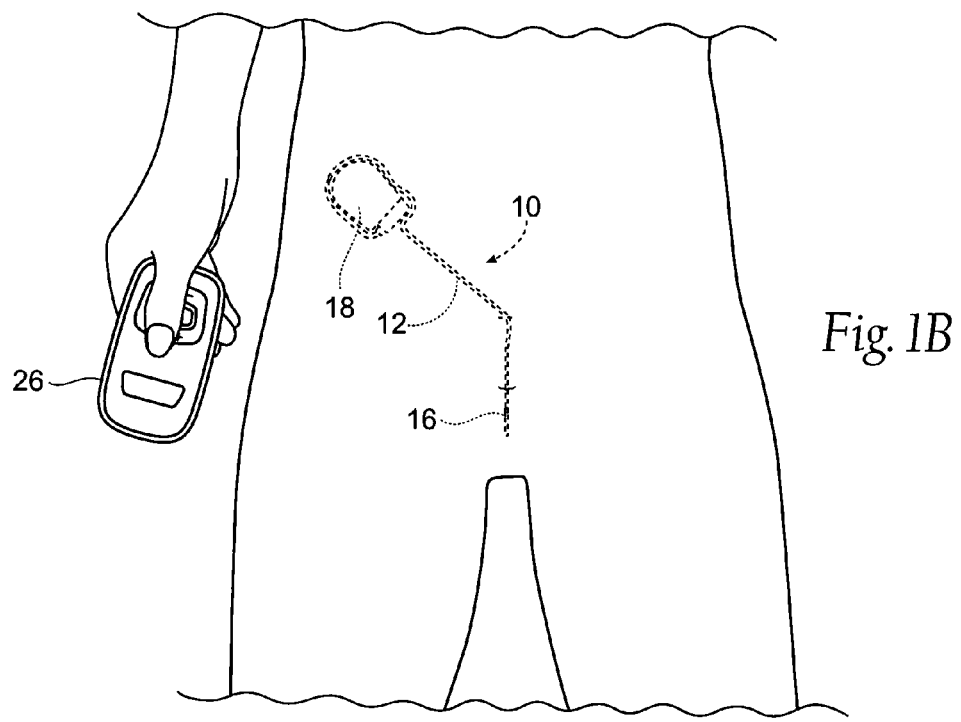
FIG. 1B is an anterior anatomical view of the implant system shown in FIG. 1A for treating urinary incontinence in humans, and showing the use of a patient controller-charger to operate the system.

FIGS. 1A and 1B show an implant system 10 for treating urinary incontinence in humans.

The implant system 10 includes an implantable lead 12 having a proximal and a distal end. The proximal end carries a plug 22, which is desirably of an industry-standard size, for coupling to an industry-sized connector 14 on a pulse generator 18. The distal end includes at least one electrically conductive surface, which will also in shorthand be called an electrode 16 (two are shown). The lead electrically connects the electrode 16 to the connector 14, and thus to the pulse generator 18 itself, while electrically insulating the wire from the body tissue except at the electrode 16.

The lead 12 and electrode 16 are sized and configured to be implanted percutaneously in tissue, and to be tolerated by an individual during extended use without pain or discomfort. The comfort is both in terms of the individual's sensory perception of the electrical waveforms that the electrode applies, as well as the individual's sensory perception of the physical or mechanical presence of the electrode and lead. In the case of the mechanical presence, the lead 12 and electrode 16 are desirably "imperceptible."

In particular, the lead 12 and electrode 16 are sized and configured to reside with stability in soft or adipose tissue 54 in the lower anterior pelvic region of the body (see FIG. 5B). It has been discovered that, when properly placed in this region, a single lead 12/electrode 16 is uniquely able to deliver electrical stimulation current simultaneously to one or both the left and right branches of the dorsal genital nerves, present near the clitoris in a female and near the base of the penis of a male (see FIGS. 5A and 5B). Specific features of the lead 12 and electrode 16 that make them well suited for this purpose, as well as other purposes, will be described in greater detail later. It is to be appreciated that the term "stimulation" includes both excitation and inhibition (blocking) of action potentials in nerves.

The implant system 10 also includes an implantable stimulation pulse generator 18 of the type described in co-pending U.S. patent application Ser. No. 11/517,056, filed Sep. 7, 2006, and entitled "Implantable Pulse Generator Systems and Methods for Providing Functional and/or Therapeutic Stimulation of Muscles and/or Nerves and/or Central Nervous System Tissue," which is incorporated herein by reference. The pulse generator 18 includes a circuit that generates electrical stimulation waveforms. An on-board battery (primary or rechargeable) provides the power. The pulse generator 18 also includes an on-board, programmable microprocessor, which carries embedded code. The code expresses pre-programmed rules or algorithms under which the desired electrical stimulation waveforms are generated by the circuit. The small metal case (e.g., titanium) of the pulse generator may also serve as the return electrode for the stimulus current introduced by the lead/electrode when operated in a monopolar configuration.

The case of the pulse generator 18 defines a small cross section; e.g., desirably about (5 mm to 10 mm thick)×(15 mm to 40 mm wide)×(40 mm to 60 mm long), and more desirably about (7 mm to 8 mm thick)×(25 mm to 35 mm wide)×(45 mm to 55 mm long). The pulse generator also defines a generally pear-shaped case. The generally pear-shaped case can be described as including a bottom portion defining a curved surface having a radius, inwardly tapering sides, and a top portion being generally flat, as shown in the Figures. This geometry provides a case including a larger end (bottom portion) and a smaller end (top portion) and allows the smaller end of the case to be placed into the skin pocket first, with the larger end being pushed in last. The shape and dimensions of the pulse generator 18 produce a volume of approximately seven to nine cubic centimeters, and more desirably about eight cubic centimeters, and a weight of approximately seventeen grams.

In an alternative embodiment, the case of the pulse generator 18 defines a small cross section; e.g., desirably about (7 mm to 13 mm thick)×(45 mm to 65 mm wide)×(30 mm to 50 mm long), and more desirably about (9 mm to 11 mm thick)×(50 mm to 60 mm wide)×(35 mm to 45 mm long). The pulse generator also defines a generally oval-shaped case. The generally oval-shaped case can be described as consisting of two congruent semicircles and two equal and parallel lines. The shape and dimensions of the pulse generator 18 produce a volume of approximately fifteen to nineteen cubic centimeters, and more desirably about seventeen cubic centimeters, and a weight of approximately twenty-seven grams.

The pulse generator 18 can deliver a range of stimulation parameters to the lead 12 and electrode 16, e.g., output current ranges of about 0.5 mA to about 20 mA, pulse duration ranges of about 0.1 microseconds to about 500 microseconds, frequency ranges of about one pulse per second to about 130 pulses per second, and duty cycle ranges from about zero to about 100 percent. The delivered stimulus is an asymmetric biphasic waveform with zero net DC (direct current).

The pulse generator 18 is sized and configured to be implanted subcutaneously in tissue at an implant depth of between about five millimeters and about twenty millimeters, desirably in a subcutaneous pocket remote from the electrode 16 and using a minimally invasive surgical procedure. As shown in FIGS. 5A and 5B, the implantation site can comprise a more medial tissue region in the lower abdomen (see also FIG. 1B). There, the pulse generator 18 can reside for extended use without causing pain and/or discomfort and/or without effecting body image. Alternatively, the implantation site can comprise a tissue region on the posterior hip, for example.

The implant system 10 includes an external patient controller-charger 26 (see FIGS. 1A and 5A). The controller 26 is sized and configured to be held by the user to transcutaneously activate and deactivate or modify the output of the pulse generator. The controller 26 may, e.g., be a simple magnet that, when placed near the site where the pulse generator 18 is implanted, toggles a magnetic switch within the implantable pulse generator 18 between an on condition and an off condition, or advances through a sequence of alternative stimulus modes pre-programmed by the clinician into implantable pulse generator 18. Alternatively, the controller 26 may comprise more sophisticated circuitry that would allow the individual to make these selections through RF (Radio Frequency) wireless telemetry communications that passes through the skin and tissue and can operate as far as an arm's length distance away from the implanted pulse generator, e.g., the controller 26 is capable of communicating with the pulse generator 18 approximately three to six feet away from the implanted pulse generator (and the pulse generator is able to communicate with the controller). The wireless telemetry circuitry provides reliable, bidirectional communications with a patient controller-charger and a clinical programmer, for example via an RF link in the 402 MHz to 405 MHz Medical Implant Communications Service (MICS) band per FCC 47 CFR Part 95, or other VHF/UHF low power, unlicensed bands.

A clinical programmer 52 (described in greater detail later) is used by a clinician to program the pulse generator 18 with a range of preset stimulus parameters. The user will then turn the implant system On/Off using the wireless patient controller-charger 26. The controller-charger is then programmed by the pulse generator, i.e., the range of or a subset of the preset stimulus parameters previously downloaded by the clinical programmer 52 is uploaded to the controller-charger 26. This range of preset stimulus parameters allows the user to make adjustments to the stimulus strength within the preset range. Stimulation will be delivered at a level that is initially set at or above the sensory threshold of the user, but is not uncomfortable. The user may get accustomed to the stimulation level, and may adjust the stimulation up or down within the preset range.

The patient controller-charger 26 may also be belt or clothing worn and used to charge the rechargeable batteries of the pulse generator 18 as needed. Charging is achieved via an inductive RF link using a charge coil on or near the skin in close proximity to the IPG. The patient controller-charger 26 may also be configured to provide the user with information on pulse generator battery status and stimulus levels.

When a rechargeable battery is used, the battery desirably has a capacity of at least 30 mA-hr and recharging of the rechargeable battery is required less than weekly. When the rechargeable battery has only a safety margin charge remaining, it can be recharged in a time period of not more than six hours.

According to its programmed rules, when switched on, the implantable pulse generator 18 generates prescribed stimulation waveforms through the lead 12 and to the electrode 16. These waveforms bilaterally stimulate the left and right branches of the dorsal genital nerves in a manner that achieves the desired physiologic response.

It has been discovered that bilateral stimulation of the dorsal genital nerves achieved by placement of a single electrode 16 at a unique location in the body (which will be described in greater detail later), achieves the desired physiologic result of consistently and effectively inhibiting unwanted bladder contractions. This makes possible the treatment of UUI and/or mixed UUI and SUI or other urinary continence dysfunctions. Using the controller 26, the individual may turn on or turn off the continence control waveforms at will or adjust the strength, depending, e.g., upon the time of day or fluid consumption.

Feasibility study results have shown significant benefits in all endpoints. For example, 21 females were enrolled in a feasibility study with a one week trial usage of a representative study system 10. Improvements identified in the study include: leaks per day reduced in 79% of reporting subjects; heavy leakage reduced in 92% of reporting subjects; pads changed per day reduced in 83% of reporting subjects; pad weight reduced in 88% of reporting subjects; frequency reduced in 72% of reporting subjects; and severe urgency reduced in 88% of reporting subjects. The study also confirmed the lead 12 and electrode 16 can implanted with a minimally invasive pre-pubic approach, and is well tolerated by the subjects. The physicians required minimal training to perform the implant procedure, which requires no fluoroscopy.

B. Physician Surgical Tools

The implant system 10 shown in FIG. 1A makes desirable a system of physician surgical tools (shown in FIGS. 2 and 3) to facilitate implantation of the implant system 10 in the intended way, desirably on an outpatient basis.

Figure 2:
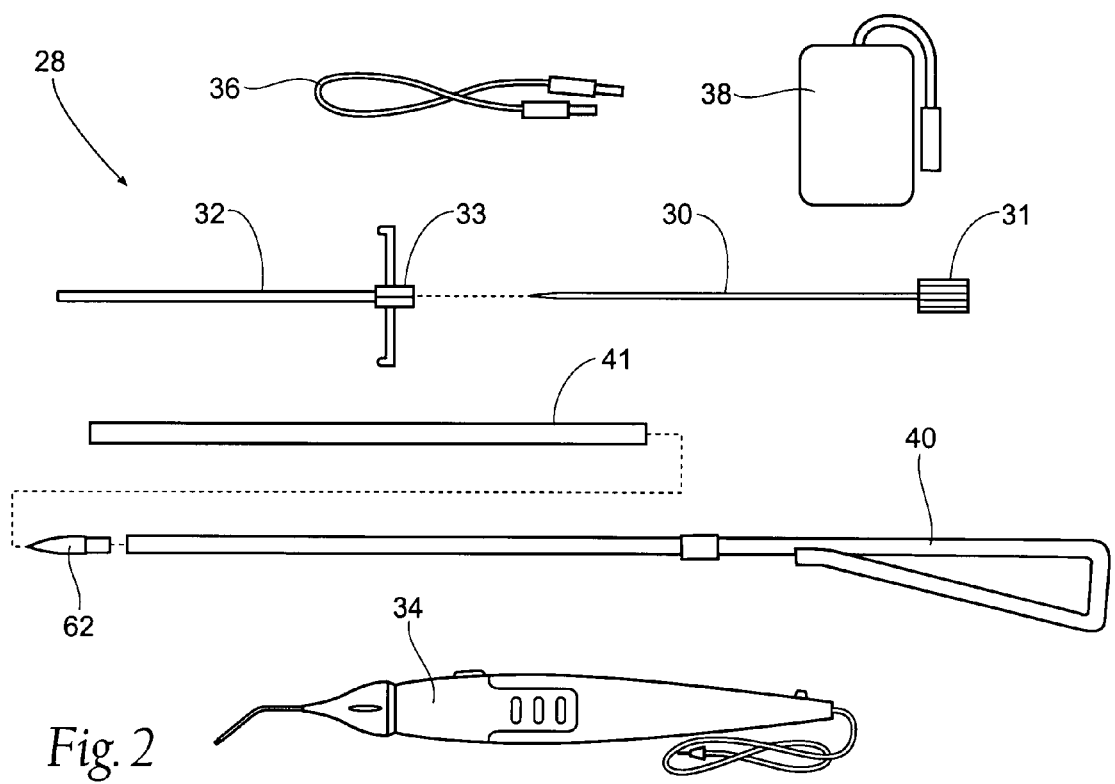
FIG. 2 is a plane view of a system of surgical tools that can be use to implant the system shown in FIG. 1A.

The surgical tool system 28 shown in FIG. 2 includes all the tools necessary for a single stage surgical procedure (i.e., without a test screening phase). The tool system 28 includes a needle 30 (or trocar) and a companion introducer sleeve 32. The needle 30 may include a luer fitting 31 to secure to a hub 33 on the introducer sleeve 32.

The needle 30 can be about 10 cm to about 15 cm long and the sleeve about 8 cm to about 13 cm long. When the needle 30 is secured inside the sleeve 32, about one cm of the needle 30 is exposed near the hub 33 of the sleeve for connection to a test stimulator 34, and about one cm is exposed at the distal tip of the sleeve 32 to deliver test stimulation to tissue. The sleeve 32 is electrically insulated or insulated except at its tip. The needle 30 is also electrically insulated, except at its tip.

The tool system 28 also includes a test stimulator 34 of the type described in co-pending U.S. patent application Ser. No. 11/651,165, filed Jan. 9, 2007, and entitled "Systems and Methods for Intra-Operative Stimulation," which is incorporated herein by reference. The test stimulator operates to generate stimulation wave pulses of the same type as the implanted pulse generator 18. The test stimulator may be a hand-held, single use, sterile, and disposable device including a battery sized to keep the test stimulator operational for a predetermined time, e.g., at least about seven hours. The test stimulator 34 includes a connector cable 36 to couple the test stimulator 34 to the needle 30. A sterile patch electrode 38 is also included, which is to be placed on the skin of the individual and coupled to the test stimulator 34, to serve as a return path for the stimulation waveforms.

In use (as will be described in greater detail later), and with the individual subject to anesthesia, the needle 30 is placed tip-first into the sleeve 32 (or the needle may be preloaded into the sleeve), and the sleeve 32 and needle 30 are advanced percutaneously approximately about five centimeters to about seven centimeters into the targeted tissue region in the lower abdomen. The needle 30 and return electrode 38 are coupled to the test stimulator 34, to apply stimulation waveforms through the tip of the needle concurrent with positioning of the needle 30.

Figure 12:
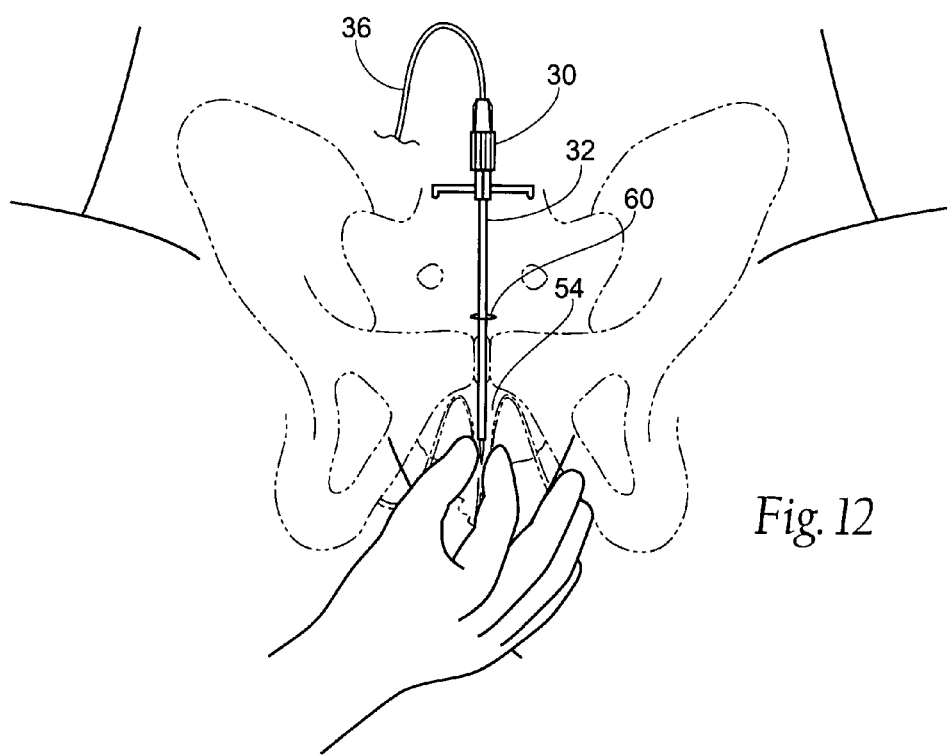
Figure 13:
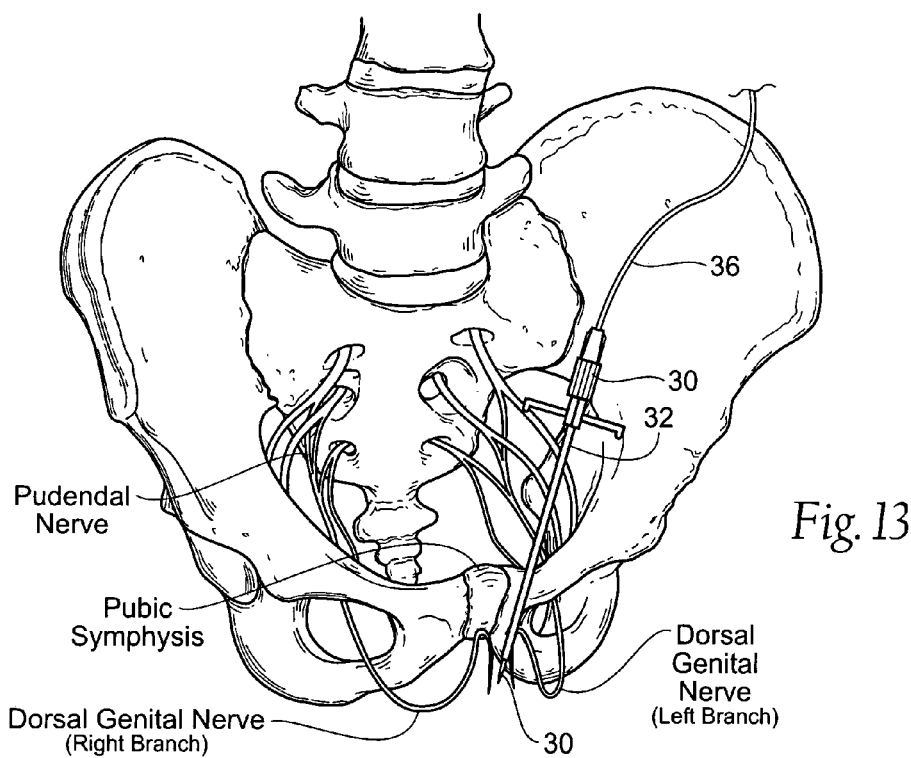

The test stimulator 34 will be used by the physician in the sterile field. The physician slowly turns up the stimulus on the test stimulator 34 and asks the patient what they feel and where they feel the stimulation sensations. The desired sensation can be described as a thumping or buzzing sensation near the clitoris. The physician may continue to penetrate and withdraw the needle 30 and sleeve 32 as necessary in a minimally invasive way, until a subcutaneous location where bilateral stimulation of both left and right branches of the genital nerves results (see FIGS. 11 through 13).

Once this location is found, the needle 30 can be withdrawn from the sleeve 32, followed by insertion of the lead 12, electrode-first, through the sleeve 32 into the location. The test stimulator 34 can then be coupled to the lead 12 through the cable 36 to confirm that the electrode 16 resides in the desired location before tunneling the lead. Then the sleeve 32 is withdrawn which fixes the location of the electrode 16, as will be described in greater detail later.

Figure 42A:
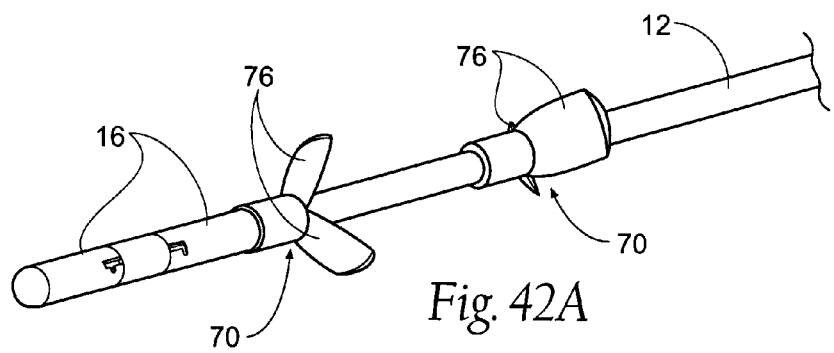
FIGS. 42A and 42B are perspective views of the lead and electrode associated with the system shown in FIGS. 1A and 1B.
Figure 42B:
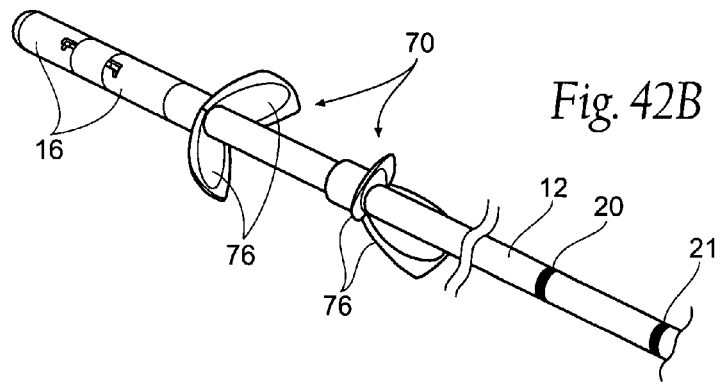

As shown in FIGS. 42A and 42B, two electrodes 16 are included with the lead 12. In order to determine the most efficient and effective configuration, the physician may first apply stimulation to the distal electrode and ask for the patient's response, then the proximal electrode, again asking for the patient's response, and then both electrodes together as one monopolar electrode, along with again asking for the patient's response. The clinical programmer 52 is capable of configuring the pulse generator 18 to apply stimulation to the electrode(s) 16 in at least the configurations described above.

The tool system 28 also includes a tunneling tool 40 and a companion introducer sleeve 41. The tunneling tool 40 is used to pass the implantable lead 12 subcutaneously from the needle incision site 60 to the pulse generator pocket 56. The tunneling tool 40 comprises a stainless steel shaft positioned inside a TEFLON® introducer sleeve 41. The shaft, which may be bendable to allow for physical contours, includes a handle to aid the physician in delivering the tunneling tool to the desired location, and a detachable tip 62 that allows the tunneling tool to cut through tissue. The shaft of the tunneling tool 40 and sleeve 41 are about 15 cm to about 25 cm long, with the tip 62 extending beyond the sleeve 41.

C. Test Screening Tools

In the above description, the surgical tool system 28 is used to implant the implant system 10 in a single surgical procedure. Alternatively, and desirably, a two-stage surgical procedure can be used.

The first stage comprises a screening phase that performs test stimulation using a temporary external pulse generator to evaluate if an individual is a suitable candidate for extended placement of the implantable pulse generator. The first stage can be conducted, e.g., during a nominal two week period. If the patient is a suitable candidate, the second stage can be scheduled, which is the implantation of the pulse generator 18 itself, as described above.

A test screening system 42 (shown in FIG. 3) can be provided to facilitate the two stage procedure. The test screening system 42 includes the lead 12 and electrode 16, which are the same as those included with the implant system 10 shown in FIG. 1A. The test screening system 42 also includes a percutaneous extension cable 44, which is sized and configured to be tunneled subcutaneously from the pocket site to a remote site (e.g., about 10 cm to about 20 cm medially) where it exits the skin. The length of the percutaneous extension cable can vary depending on the anatomy of the patient, and in one representative embodiment can be about 30 cm to about 40 cm, and in one embodiment is 32 cm long. The percutaneous extension cable has a proximal and distal portion. The proximal portion carries a standard female IS-1 receptacle 46 for connection to the industry-standard size plug on the end of the lead 12. The distal portion of the percutaneous extension cable 44 carries a plug 48 that couples, e.g., screws, to an intermediate external extension cable 88, which itself is coupled to an external pulse generator 35, which the test screening system 42 further includes.

In one embodiment, the external pulse generator 35 includes an integral return electrode on its tissue facing side. In an alternative embodiment, the patch return electrode 38 is included, or is otherwise available, to be coupled to the external pulse generator 35.

The test screening system 42 also includes the intermediate external extension cable 88. One end of the external extension cable 88 carries a plug 90 to connect to the external pulse generator 35. The other end of the external extension cable 88 includes a connector 92 to receive the plug 48 of the percutaneous extension cable 44. This end of the external extension cable 88 can also be sized and configured to connect directly to the optional surface patch electrode 38.

In use (as will be described in greater detail later), the physician makes use of the surgical tool system 28, including the needle 30 and sleeve 32, and the tunneling tool 40 to implant the electrode 16 and tunnel the lead 12 to the desired location, in the manner previously described. The components of a surgical tool system 28 can be provided with the test screening system 42. The percutaneous extension cable 44 is coupled to the lead 12. Using the tunneling tool 40 of the surgical tool system 28, the physician subcutaneously creates a tunnel to a suitable exit site, which is desirably remote from the site where the pocket for the implanted pulse generator is to be created in the second phase. The tunneling tool 40 is removed, leaving the sleeve 41 in place. The percutaneous extension cable 44 is then slid through the sleeve 41 and the sleeve is removed. Further details of this will be described in greater detail later. A short length of the percutaneous extension cable 44 that carries the plug 48 extends outside the exit site, for coupling the electrode 16 to the external pulse generator 35 via the intermediate external extension cable 88. The return patch electrode 38 is also coupled to the external pulse generator 35.

The individual patient wears the external pulse generator 35 and return patch electrode 38 for the prescribed test period. The external pulse generator 35 supplies the prescribed stimulation regime. If an improvement in urinary continence is achieved, the second phase is warranted. In the second phase, the percutaneous extension cable 44 is removed and discarded, and the implantable pulse generator is connected to the lead 12 and installed in a pocket remote from the electrode 16 in the manner previously described.

D. Clinician Tools

A clinical tool system 50 is desirably provided to condition the implanted pulse generator 18 to perform in the intended manner.

In the embodiment shown in FIG. 4, the clinical tool system 50 includes a clinical programmer 52 of the type described in co-pending U.S. patent application Ser. No. 11/541,890, filed Oct. 2, 2006, and entitled "Systems and Methods for Clinician Control of Stimulation Systems," which is incorporated herein by reference. The clinical programmer 52 can be placed into transcutaneous communication with an implanted pulse generator 18, e.g., through wireless telemetry that provides reliable, bidirectional communications with the programmer 52, an external patient controller-charger, or a charger via an RF link in the 402 MHz to 405 MHz Medical Implant Communications Service (MICS) band per FCC 47 CFR Part 95, or other VHF/UHF low power, unlicensed bands (see FIG. 38). The clinical programmer 52 may incorporate a custom program operating on a handheld computer or other personal digital appliance (PDA). The clinical programmer 52 or PDA includes an on-board microprocessor powered by a rechargeable, on-board battery (not shown). The microprocessor carries embedded code which may include pre-programmed rules or algorithms that allow a clinician to remotely (i.e., wirelessly) download program stimulus parameters and stimulus sequences parameters into the pulse generator. The microprocessor of the clinical programmer 52 is also desirably able to interrogate the pulse generator and upload operational data from the implanted pulse generator.

II. Implanting the Implant System

A. The Anatomic Landmarks

As already described, certain components of the implant system 10 are sized and configured to be implanted in adipose tissue in a particular location in an individual's lower abdomen, where it has been discovered that effective bilateral stimulation of both the left and right branches of the dorsal genital nerves can be achieved with a single electrode. The main anatomic landmark guiding the unique placement of these components is the pubic symphysis.

As FIG. 6 shows, the hip bones are two large, irregularly shaped bones, each of which develops from the fusion of three bones, the ilium, ischium, and pubis. The ilium is the superior, fan-shaped part of the hip bone. The ala of the ilium represents the spread of the fan. The iliac crest represents the rim of the fan. It has a curve that follows the contour of the ala between the anterior and posterior superior iliac spines.

Figure 7:
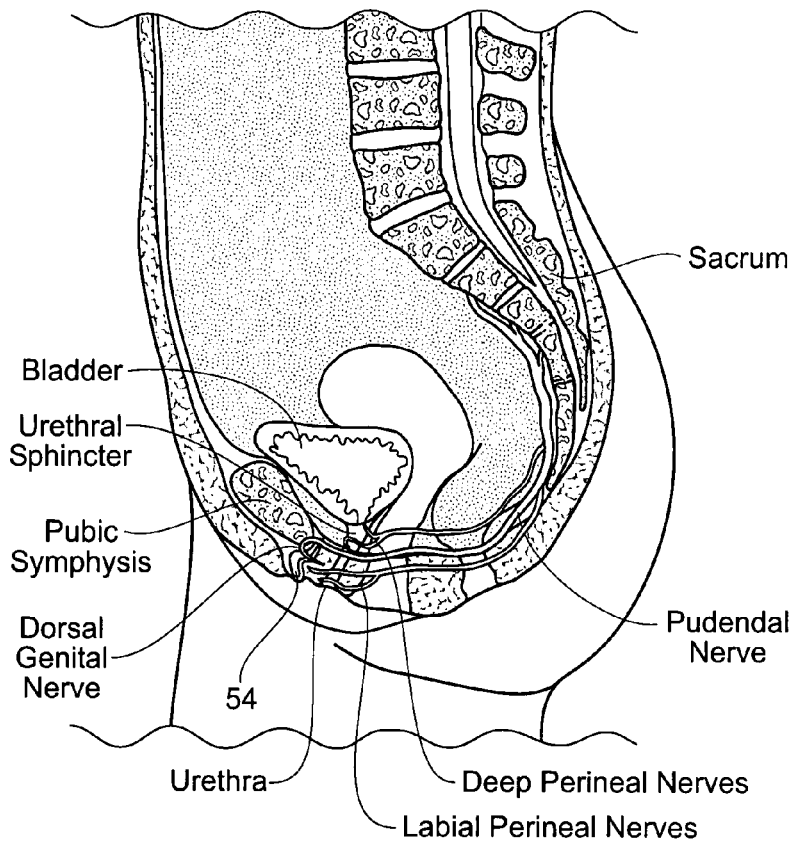
FIG. 7 is a lateral section view of the pelvic girdle region shown in FIG. 6.

As FIGS. 6 and 7 show, the sacrum is formed by the fusion of five originally separate sacral vertebrae. The hip bones are joined at the pubic symphysis anteriorly and to the sacrum posteriorly to form the pelvic girdle (see FIG. 6). The pelvic girdle is attached to the lower limbs. Located within the pelvic girdle are the abdominal viscera (e.g., the ileum and sigmoid colon) and the pelvic viscera (e.g., the urinary bladder and female reproductive organs such as the uterus and ovaries).

Within this bony frame (see FIGS. 6 and 7), the pudendal nerve is derived at the sacral plexus from the anterior divisions of the ventral rami of S2 through S4. The pudendal nerve extends bilaterally, in separate branches on left and right sides of the pelvic girdle. Each branch accompanies the interior pudendal artery and leaves the pelvis through the left and right greater sciatic foramens between the piriformis and coccygeus muscles. The branches hook around the ischial spine and sacrospinous ligament and enter the skin and muscles of the perineum through the left and right lesser sciatic foramen.

Figure 8:
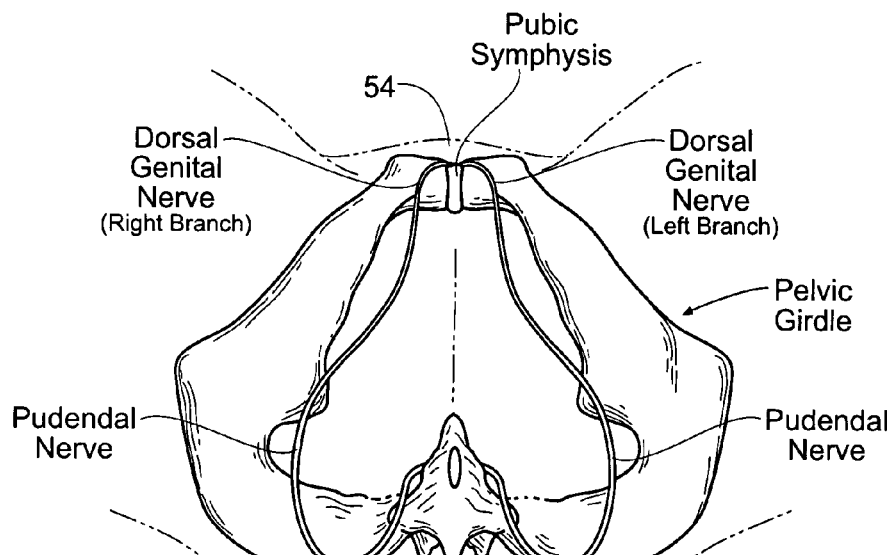
FIG. 8 is an inferior view of the pelvic girdle region shown in FIG. 6.

As shown in the inferior pelvic view of FIG. 8, the bilateral left and right branches of the pudendal nerve extend anteriorly through the perineum, each ending as the dorsal genital nerve of the penis or clitoris. The genital nerves are the chief sensory nerve of the external genitalia. The Figures are largely based upon the anatomy of a female, but the parts of the male perineum are homologues of the female.

As FIGS. 7 and 8 show, in the male and female, adipose tissue 54 overlays the pubic symphysis. The bilateral branches of the genital nerves innervate this tissue region. In the female, this tissue region is known as the mons pubis. In the male, the penis and scrotum extend from this region. Further discussion regarding the fixation of the lead 12 and electrode 16 in adipose tissue 54 will be described later.

Stimulation of the dorsal genital nerves provides direct and selective activation to the sensory fibers that lead to inhibition of the bladder and does not activate other nerve fibers that are present in the pudendal nerve and sacral spinal nerve roots. Access to the dorsal genital nerve near the pubic symphysis can be accomplished in a minimally invasive manner and uses anatomical landmarks and structures of which pelvic health care specialists are expert, as they commonly operate in the pelvic region.

Direct stimulation of the dorsal genital nerve (a purely sensory nerve) should eliminate the variability associated with placement and stimulation of mixed (motor and sensory) nerve bundles (i.e., spillover stimulation to unwanted nerves is eliminated).

This simpler anterior surgical implantation procedure of the present invention avoids risk of injury to the spine associated with sacral nerve stimulation. It does not require fluoroscopy or urodynamics, as the patient's report of sensation and the anatomical landmarks are used to guide placement. Implantation in the described region is in an area in which urologists commonly operate. Further, the approach is less invasive than a deep pelvic approach required to place the Bion.

The placement of the lead/electrode will stimulate bilateral branches of the dorsal genital nerves, since the electrode will be placed at or near where the right and left branches originate. This electrode placement differs from the sacral and pudendal nerve stimulation devices that only stimulate the left or right branch, but not both.

Figure 53:
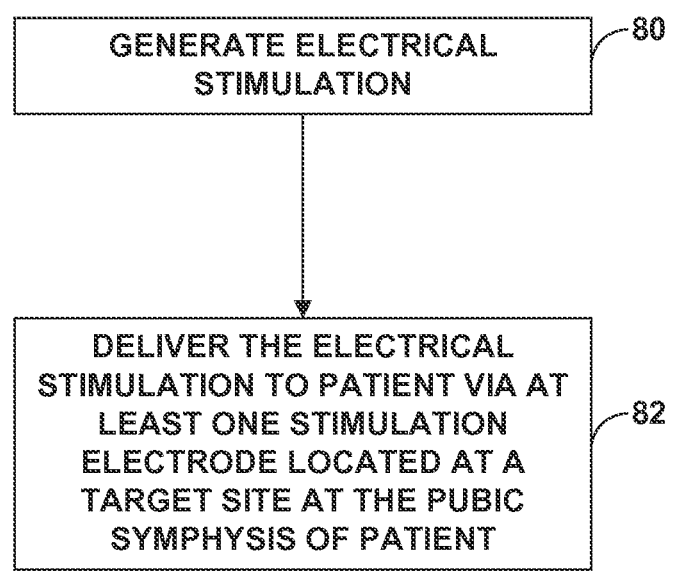
FIG. 53 is a flow diagram illustrating an example technique for delivering stimulation therapy to a patient.

FIG. 53 is a flow diagram illustrating an example technique for delivering stimulation therapy to a patient. As shown in FIG. 53, pulse generator 18 of implant system 10 may generate electrical stimulation (80). Pulse generator 18 may deliver the electrical stimulation to the patient via at least one electrode, e.g., electrode 16 of lead 12, located at a target site at the pubic symphysis of the patient (82). In accordance with examples described herein, the electrical stimulation and the target site may be selected to bilaterally stimulate the left branch and right branch of a dorsal genital nerve of the patient.

B. Implantation Methodology

Representative anterior surgical techniques will now be described to place an electrode 16 and lead 12 in a desired location in adipose tissue 54 at or near the pubic symphysis. It is this desired placement that makes possible the bilateral stimulation of both left and right branches of the dorsal genital nerves with a single lead 12 to provide continence.

These representative surgical implantation methods for implanting the electrode 16 and lead 12, percutaneous extension cable 44, and pulse generator 18, of the present invention allows for more rapid placement of these components for the treatment of incontinence whereby the electrode 16 is placed so as to achieve bilateral stimulation of both left and right branches of the dorsal genital nerves. Implanting the lead 12 and electrode 16 near the dorsal genital nerves can be easily achieved without fluoroscopy, and because of this readily accessible location, implantation times are reduced from current procedures for existing medical electrical leads stimulating the sacral nerve fibers. In the two-stage procedure described below, the first stage may be completed in approximately 30 to 60 minutes, or less, and the second stage may be completed in approximately less than 30 minutes.

Before implantation, and at the physician's discretion, an oral broad spectrum antibiotic may be given and continued for five days. With the patient in a supine position, the lower abdomen from the pubic symphysis to umbilicus and from the anterior iliac spines bilaterally are prepped with Betadine (or Hibiclens Solutions for cases of Betadine allergy).

As before generally described, implantation of the implant system 10 shown in FIGS. 1A and 1B can entail a two-stage surgical procedure, including a test screening phase, or a single stage surgical procedure in which the pulse generator is implanted without a screening phase. Each will now be described.

1. Two-Stage Surgical Procedure

FIGS. 9 to 39 illustrate steps of implanting an implant system 10 in a two-stage surgical procedure. The first stage installs the electrode 16 and lead 12, and connects the lead 12 to a temporary external pulse generator 35. If the use of the external pulse generator 35 achieves the desired results, an implantable pulse generator 18 is implanted in a second stage.

a. The First Stage:
Test Screening Phase

Locating the Lead/Electrode

The patient may undergo monitored anesthesia care (MAC), which is a planned procedure during which the patient undergoes local anesthesia together with sedation and analgesia. During MAC, the patient is sedated and amnestic but always remains responsive when stimulated to do so. Local anesthesia—e.g., 1% Lidocaine (2-5 ccs) or equivalent—may be injected prior to making the anticipated needle 30 incision site 60. The site for the needle incision 60 is desirably located midline or near-midline, over the pubic symphysis aiming toward the clitoris (or the base of the penis in males).

Figure 9:
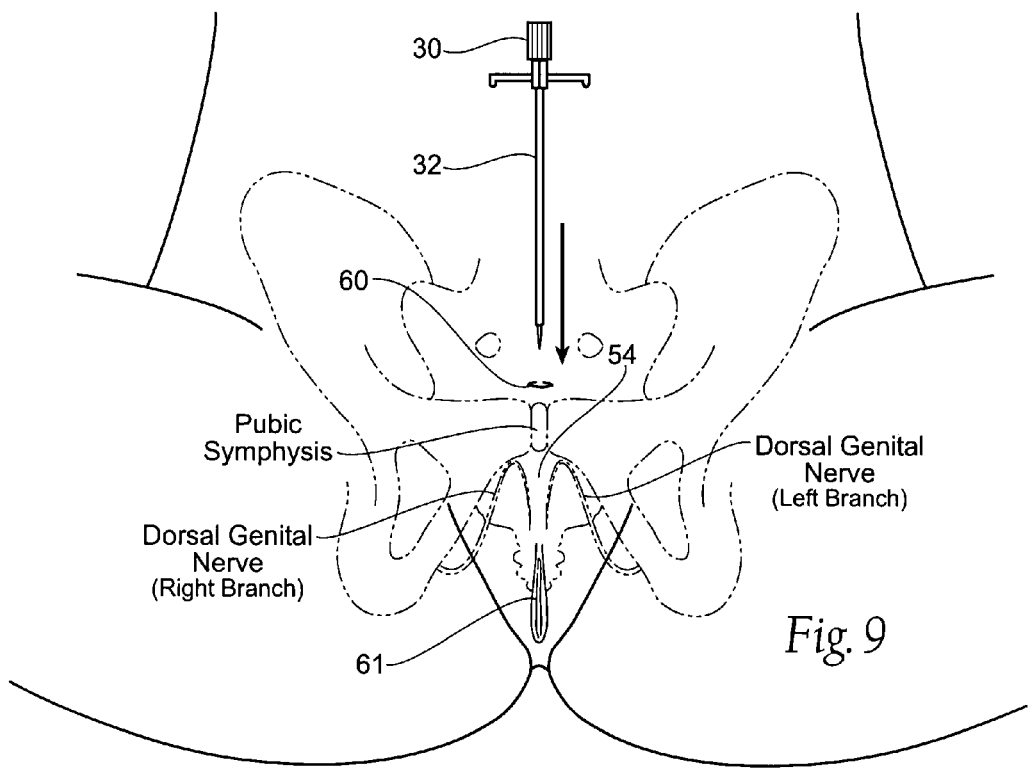
FIGS. 9 to 39 illustrate steps of implanting the system shown in FIGS. 1A and 1B in a two-stage surgical procedure.
Figure 10:
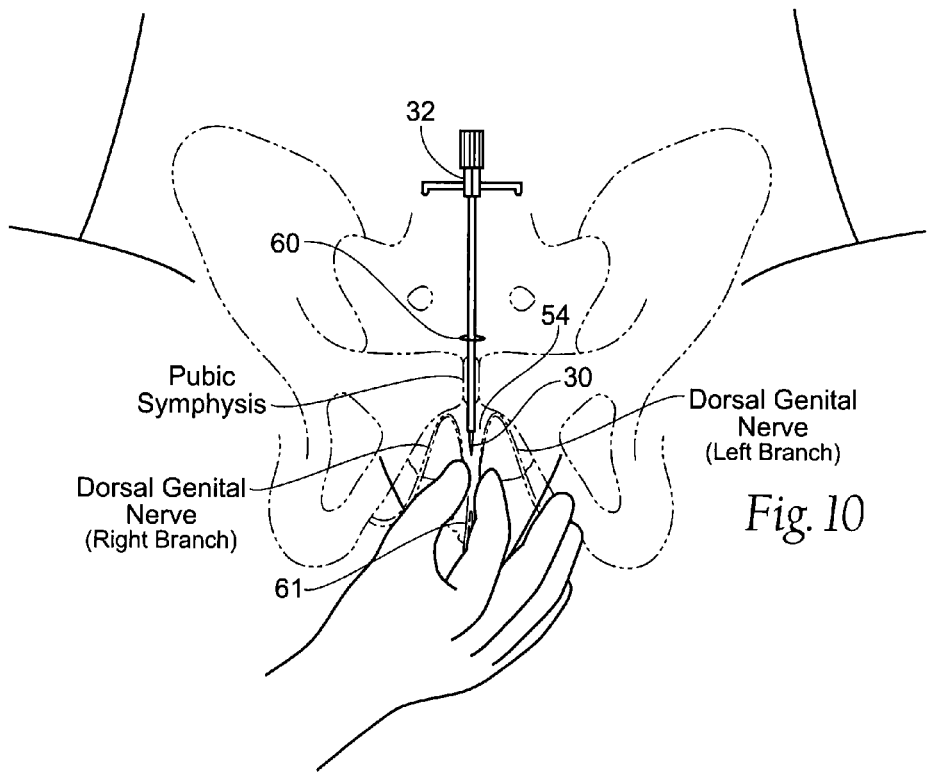
Figure 11:
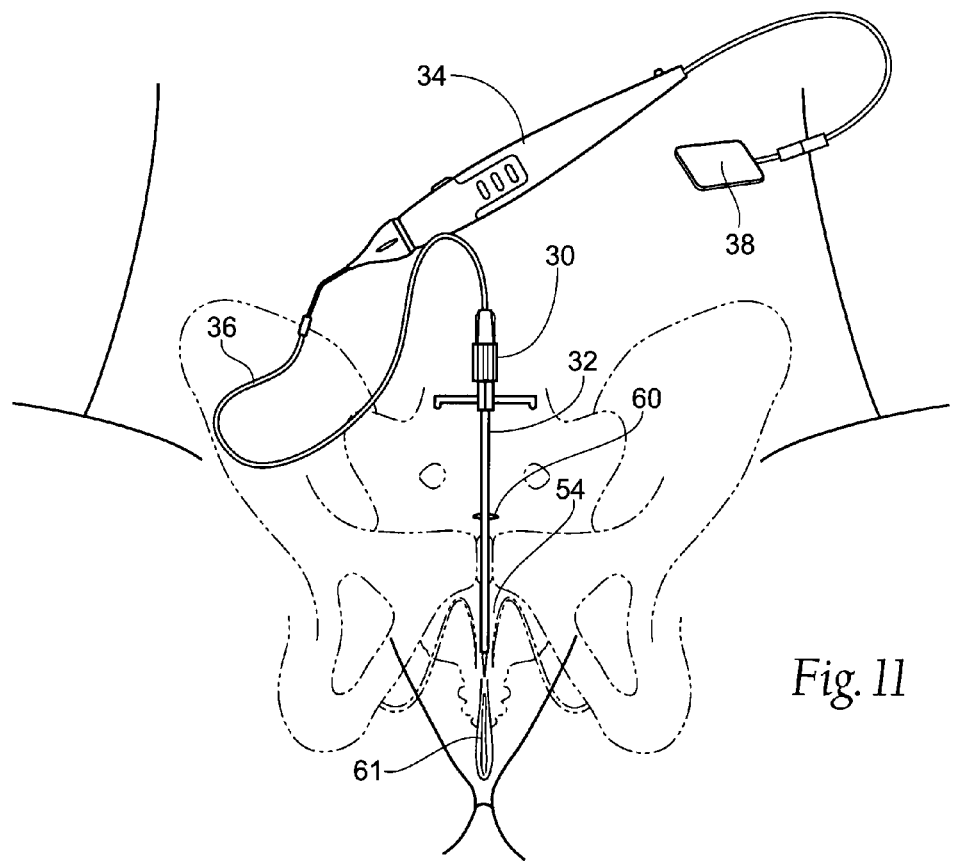

Once local anesthesia is established, and as shown in FIGS. 9 and 10, the needle 30 and sleeve 32 are advanced (the sleeve 32 being pre-loaded over the needle 30) percutaneously into the anesthetized site 60 to a depth of about five centimeters to about seven centimeters necessary to reach the target site between the pubic symphysis and the clitoris 61. It is to be appreciated that this approximate insertion depth may vary depending on the particular anatomy of the patient. The physician may use one hand to guide the needle 30 and the other hand to hold the clitoris 61 to stabilize the surrounding tissue. As FIG. 11 shows, once the needle 30 is positioned, it is coupled to the test stimulator 34 (via the cable 36), to apply stimulation waveforms through the needle tip concurrent with positioning of the needle 30. A patch electrode 38 placed on the skin near the hip of the individual is also coupled to the test stimulator 34 to serve as a return path for the stimulation waveforms.

The test stimulator 34 will be used by the physician in the sterile field. The physician slowly turns up the stimulus on the test stimulator 34 and asks the patient a number of questions to elicit feedback on what they feel and where they feel the stimulation sensations. The desired sensation can be described as a thumping or buzzing sensation near the clitoris. The physician may continue to ask the patient questions and to penetrate and withdraw the needle 30 and sleeve 32 as necessary in a minimally invasive way, until a subcutaneous location where bilateral stimulation of both left and right branches of the genital nerves results (see FIGS. 12 and 13).

Figure 14:
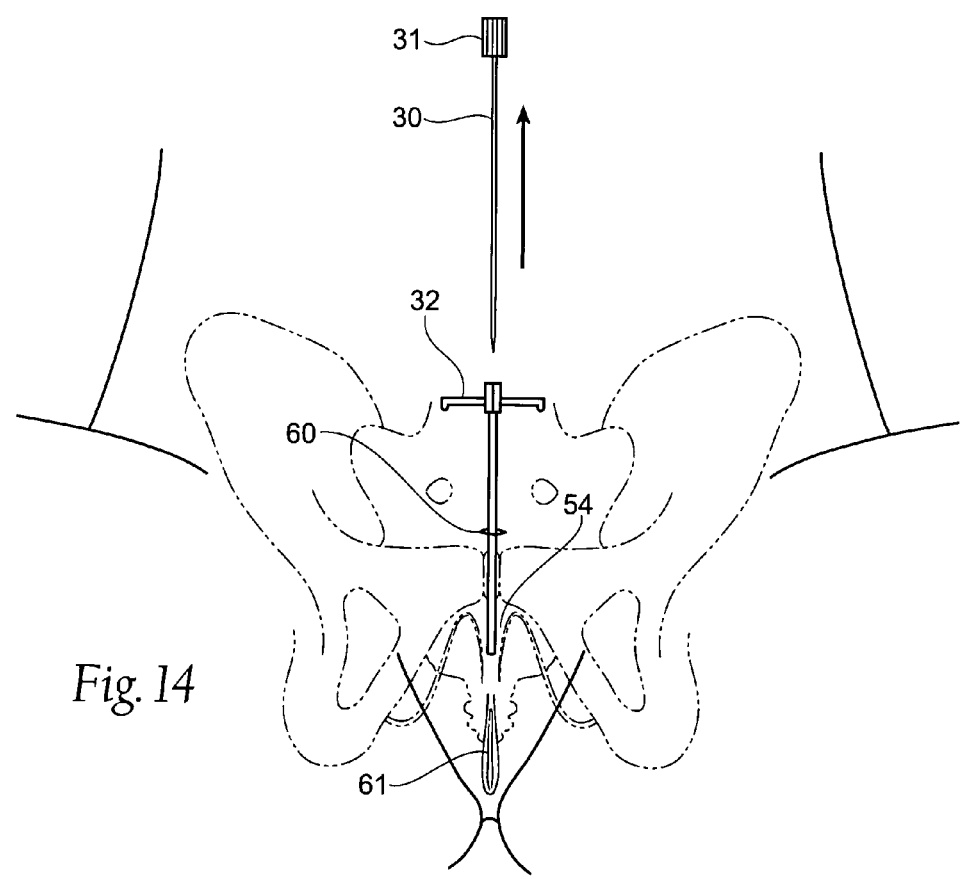

As FIG. 14 shows, once this location is found, the test stimulator 34 is disconnected from the needle 30 and the needle is withdrawn from the sleeve 32.

Figure 15:
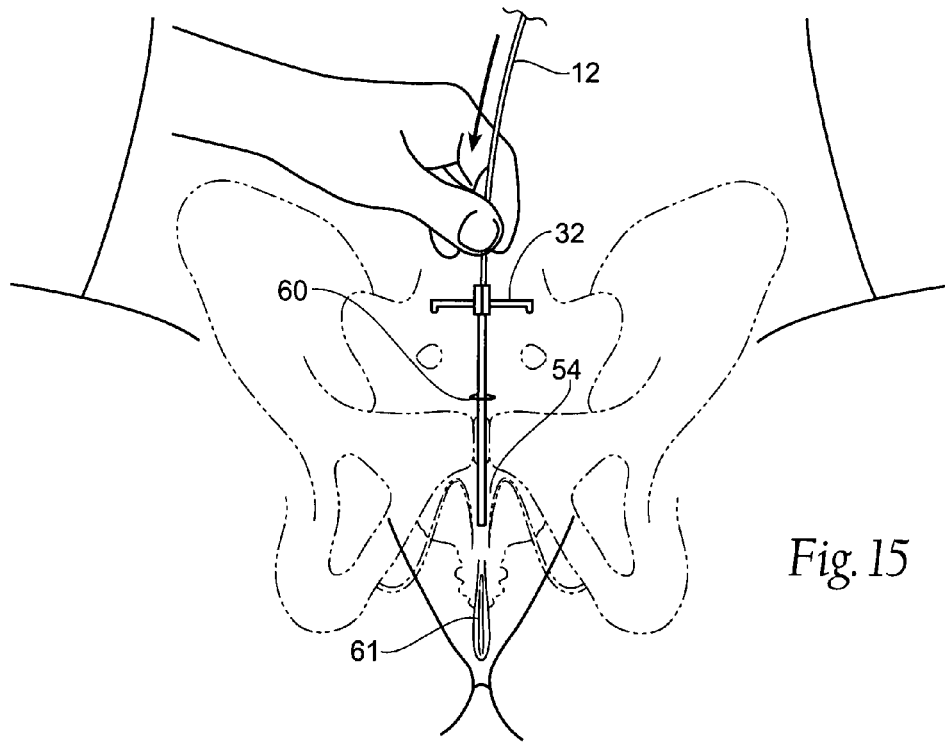
Figure 16:
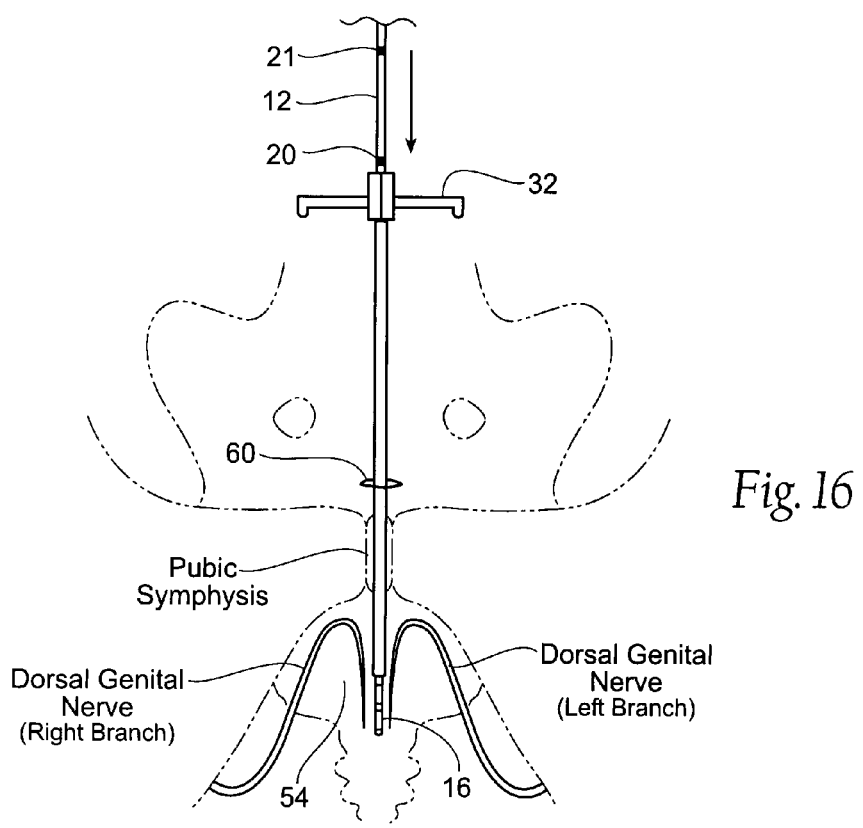
Figure 17:
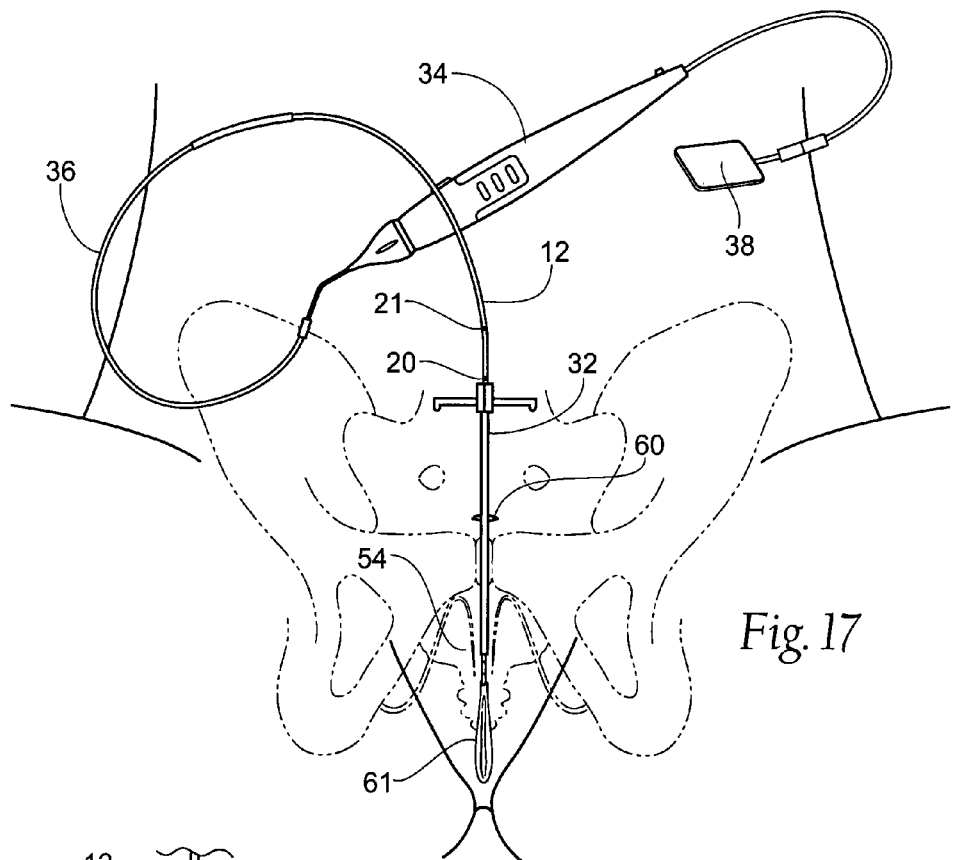

As FIGS. 15 and 16 show, the lead 12, electrode-first, is passed through the sleeve 32. Desirably, a guide wire 94 may be preloaded into a lumen 13 in the lead 12 to provide temporary stiffening during insertion. As FIG. 16 shows, the lead is inserted into the sleeve 32 until a first visual marker 20 on the distal portion of lead 12 indicates that the electrode 16 has been exposed out of the distal end of the sleeve. The lead 12 is now coupled to the test stimulator 34 (via the cable 36), to again apply stimulation waveforms through the electrode 16 concurrent with positioning of the electrode (see FIG. 17). Again, the physician slowly adjusts the stimulation via the test stimulator 34 and asks for the patient feedback of sensation. Based on the patient feedback, the physician repositions the lead if necessary.

Once the optimal location is found, the physician removes the cable 36 from the lead 12, and applies pressure on the skin over top where the electrode 16 is positioned. The guide wire 94 may be withdrawn. This applied pressure helps to secure the lead in place while the sleeve 32 is being removed.

Figure 18A:
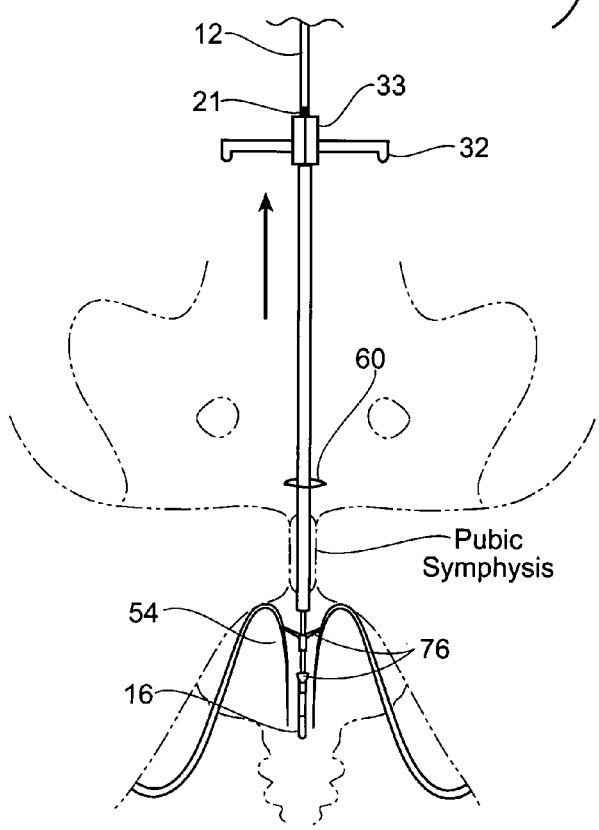
Figure 18B:
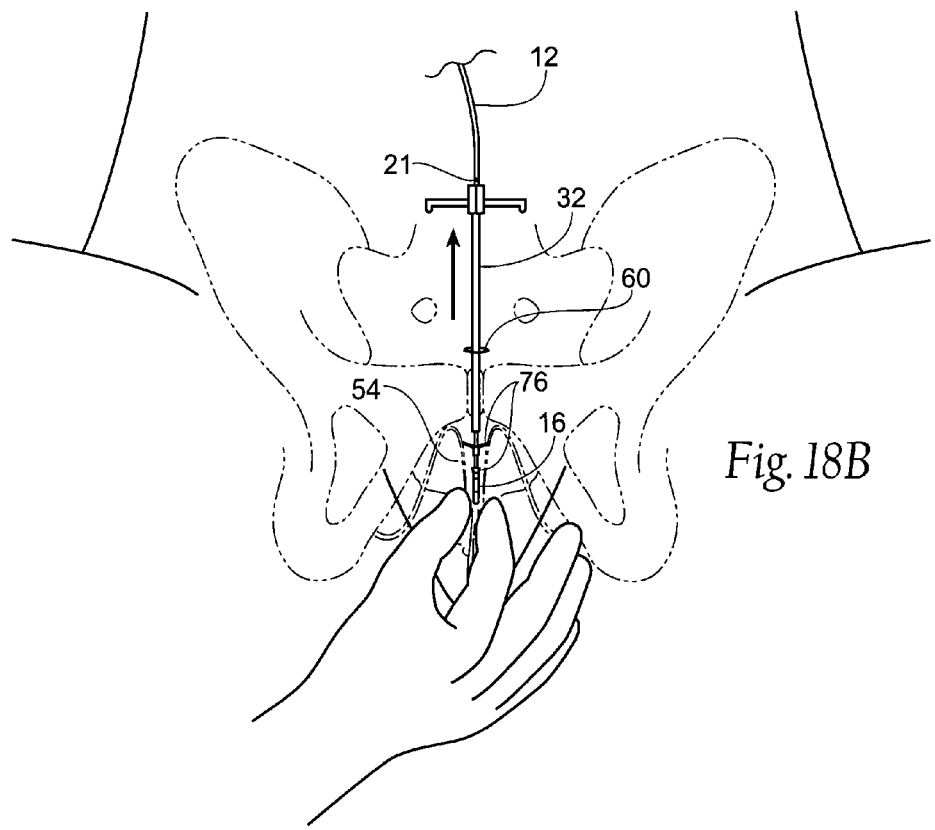
Figure 19:
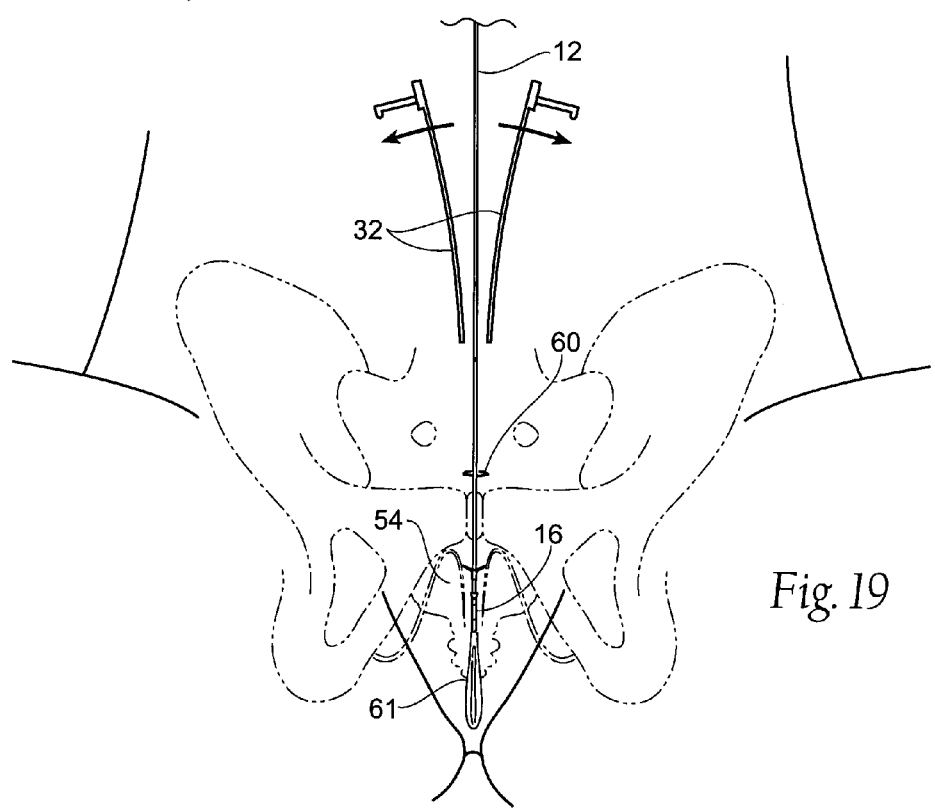
Figure 20:
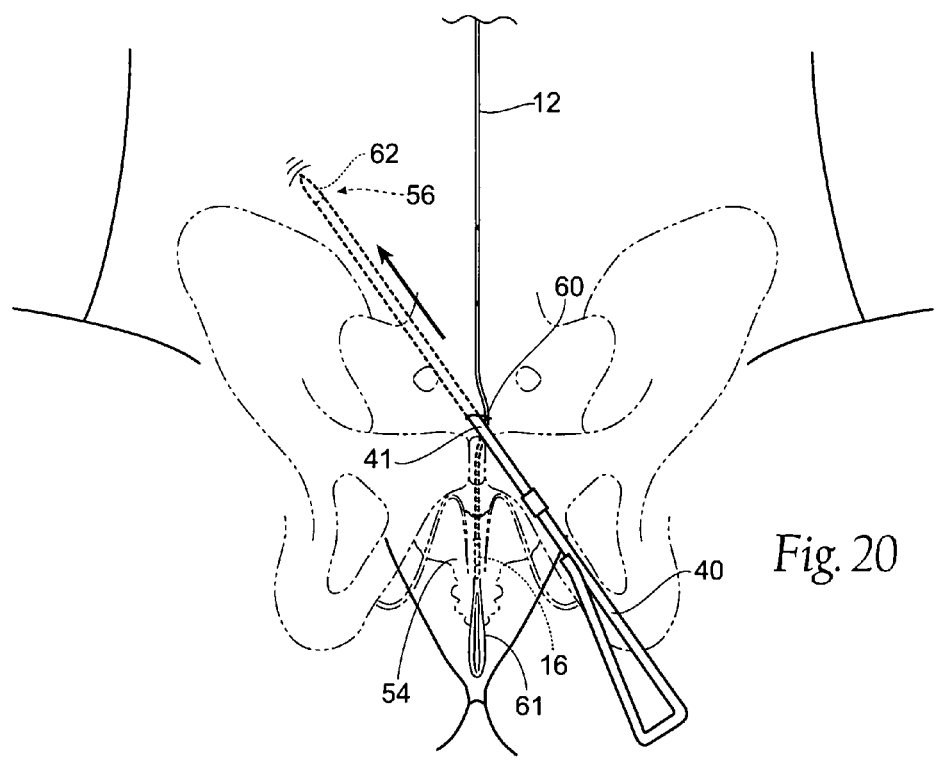

As FIG. 18A shows, the introducing sleeve 32 is withdrawn at least until the second visual lead marker 21 is aligned with the hub 33 on the sleeve, which indicates that the tines 76 on the lead 12 have been deployed, which fixes the location of the electrode 16 in the adipose tissue. With the physician applying pressure, the sleeve 32 can now be pulled back out of the body (see FIG. 18B). Once the introducing sleeve 32 is completely out of the body, and toward the proximal end of the lead 12, the physician separates or peels apart the sleeve 32 into two pieces, as shown in FIG. 19, allowing the sleeve 32 to be removed from the lead.

Optionally, the test stimulator 34 may again be coupled to the lead 12 via the cable 36 (see FIG. 17) to apply stimulation pulses through the electrode 16, to confirm that the electrode 16 resides in the location previously found.

Tunneling the Lead

Having implanted the lead/electrode, a subcutaneous tunnel is formed for connecting the lead 12/electrode 16 to the percutaneous extension cable 44. By using a skin knife, the size of the needle incision site 60 (where the lead 12 now exits the body) may be increased to allow space for the tunneling tool 40. Next, the tunneling tool 40 with sharp tip 62 and sleeve 41 (shown in FIG. 2) is introduced through the needle incision site 60 (see FIG. 20) and pushed toward the pulse generator pocket site 56. Once the tip 62 of the tunneling tool 40 is in a desired position (identified by the physician through sight and feel), a pocket incision 64 is made for forming the subcutaneous pocket 56 for the pulse generator (to be formed in the second stage), followed by passing the tip 62 of the tunneling tool 40 through the newly formed incision 64 (see FIG. 21).

Figure 21:
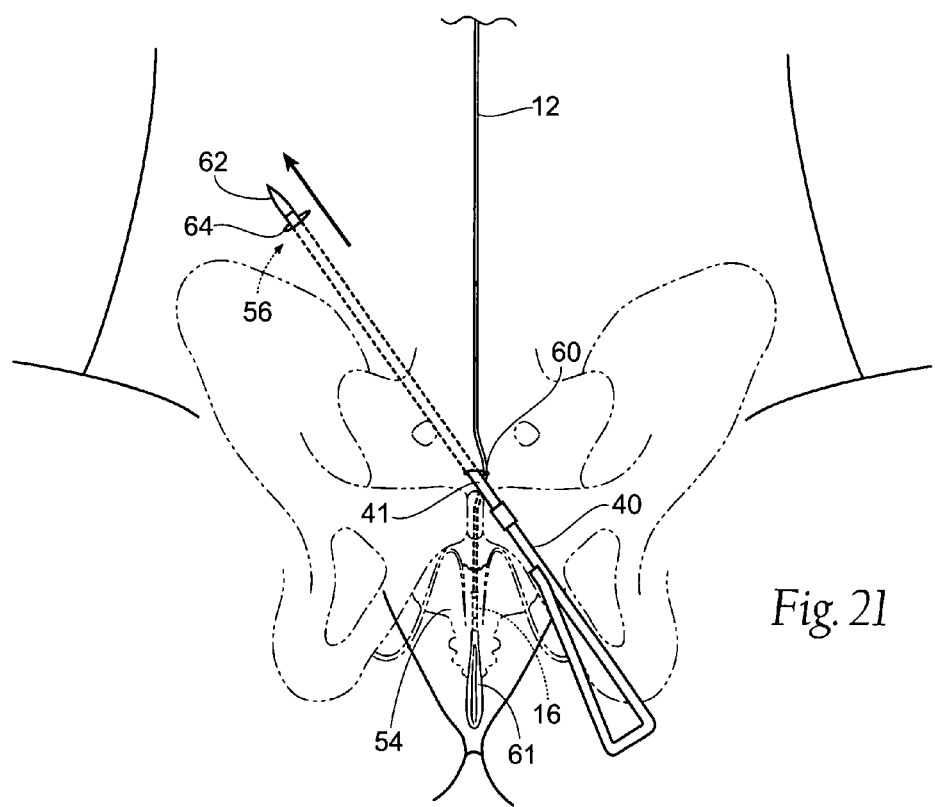
Figure 22:
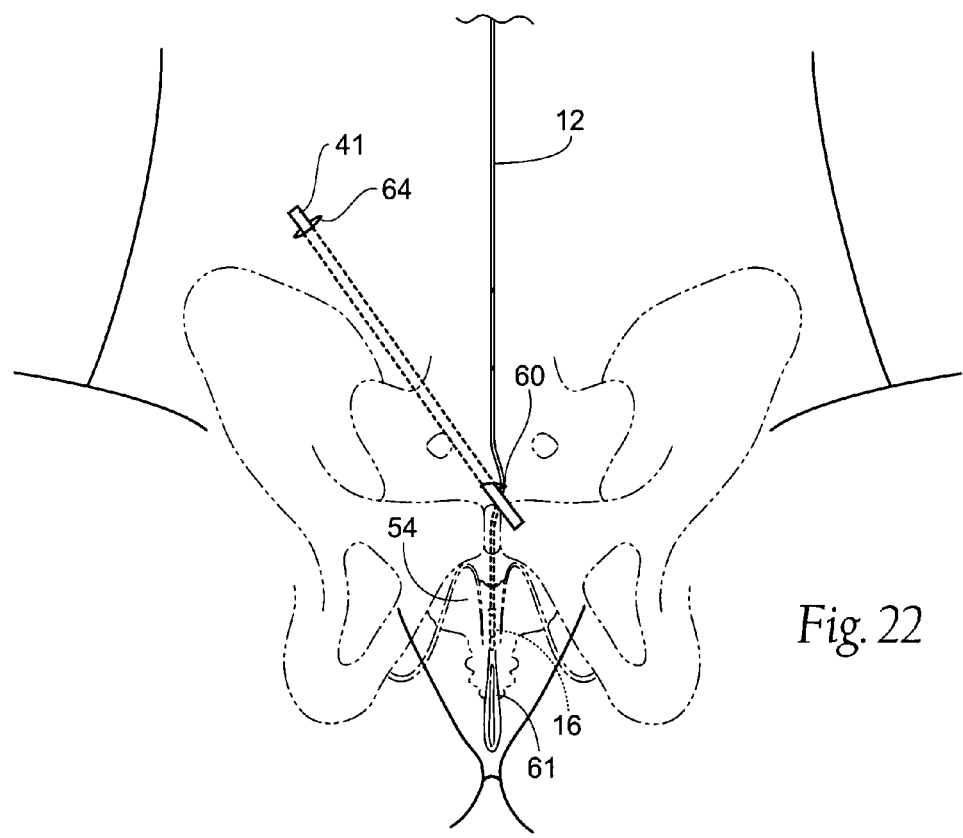

The incision 64 may comprise a lateral approximately 2 cm incision, which, in FIG. 21, is located at or near two fingerbreaths medial to the anterior iliac spine and made in the direction of the dermatomal skin line. Again, local anesthesia—e.g., 1% Lidocaine (2-5 ccs) or equivalent—may be injected before making the incision in this site.

Figure 23:
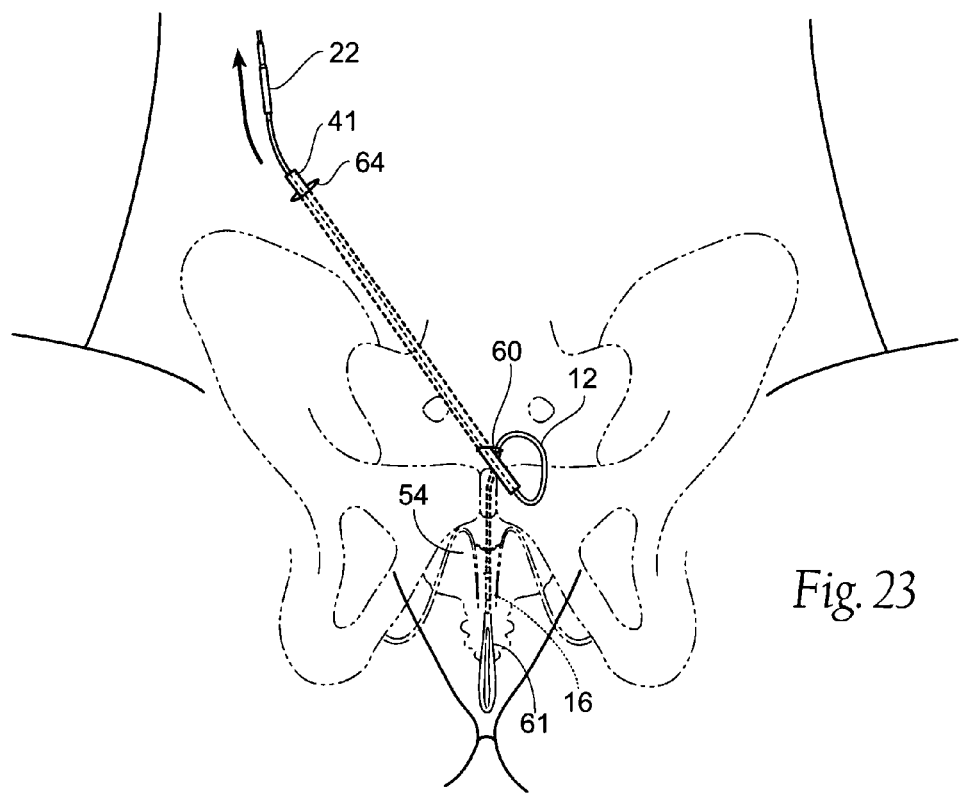
Figure 24:
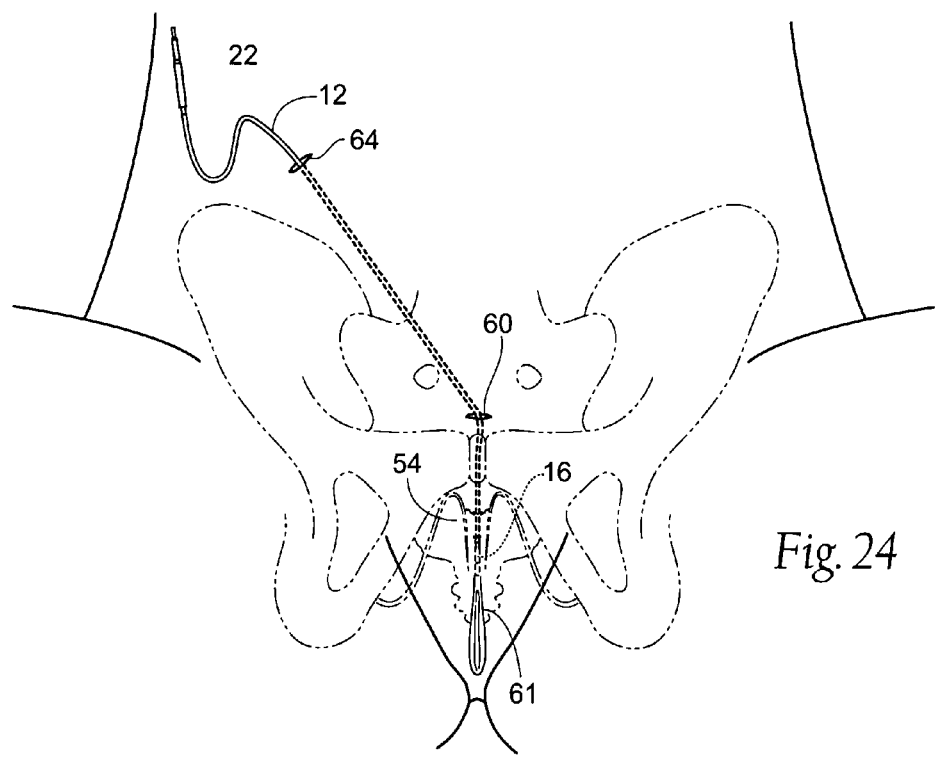
Figure 25:
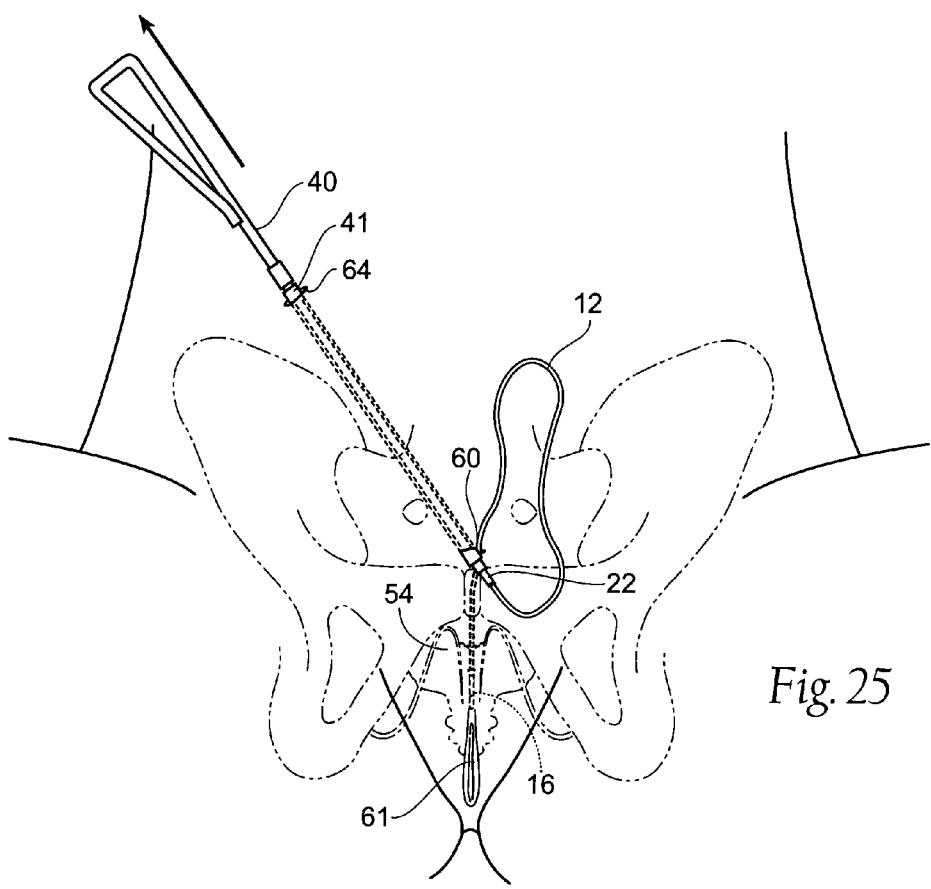

Removal of the tunneling tool 40 leaves the sleeve 41 in place (see FIG. 22), and allows the physician to pass the lead 12 from the needle incision site 60 through the sleeve 41 and to the pocket incision site 64, followed by removal of the sleeve (see FIGS. 23 and 24).

If the physician experiences resistance in pushing the lead 12, the plug 22 on the lead 12 can be attached to the tunneling tool 40 and pulled through the sleeve 41. The tunneling tool 40 with the sharp tip 62 removed is reinserted into the sleeve 41 at the pocket incision site 64 and pushed until the tip exits at the needle incision site 60. The plug 22 of the lead 12 is attached to the tunneling tool 40, and the tunneling tool and lead are retracted out the pocket incision site 64 (see FIG. 25).

It should be appreciated that, in an alternative technique, the tunneling tool 40 may include a removable sharp tip 62 (see FIG. 2) that is present during tunneling, but that is removed once passage through the distant incision site 64 occurs. With the sharp tip 62 removed, the lead 12 can be passed through an open lumen of the tunneling tool 40 to the pocket incision site 64.

It should also be appreciated that the directions described above and below for the tunneling tool 40 may be reversed, i.e., instead of tunneling from the needle incision site 60 to the pocket incision site 64, the tunneling may be done from the pocket incision site to the needle incision site.

Tunneling the Percutaneous Extension Cable

Similar to the procedure described above for tunneling the lead 12, a tunnel is created to extend a percutaneous extension cable 44 from the pocket incision site 64 to a second incision site 66.

Figure 26A:
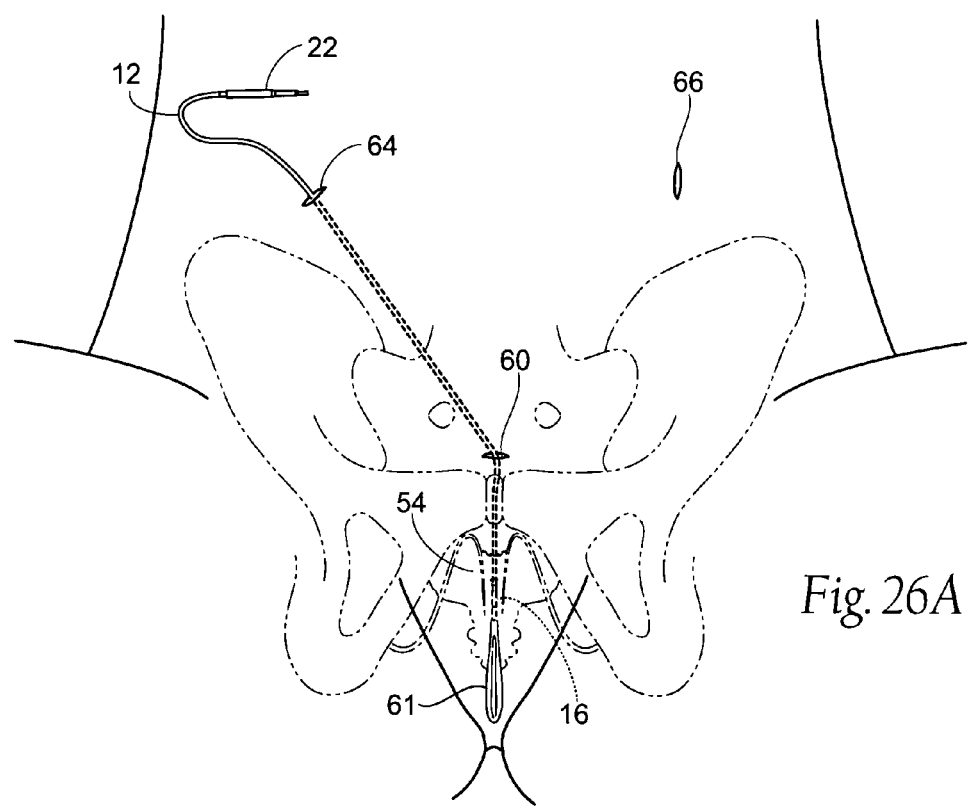
Figure 26B:
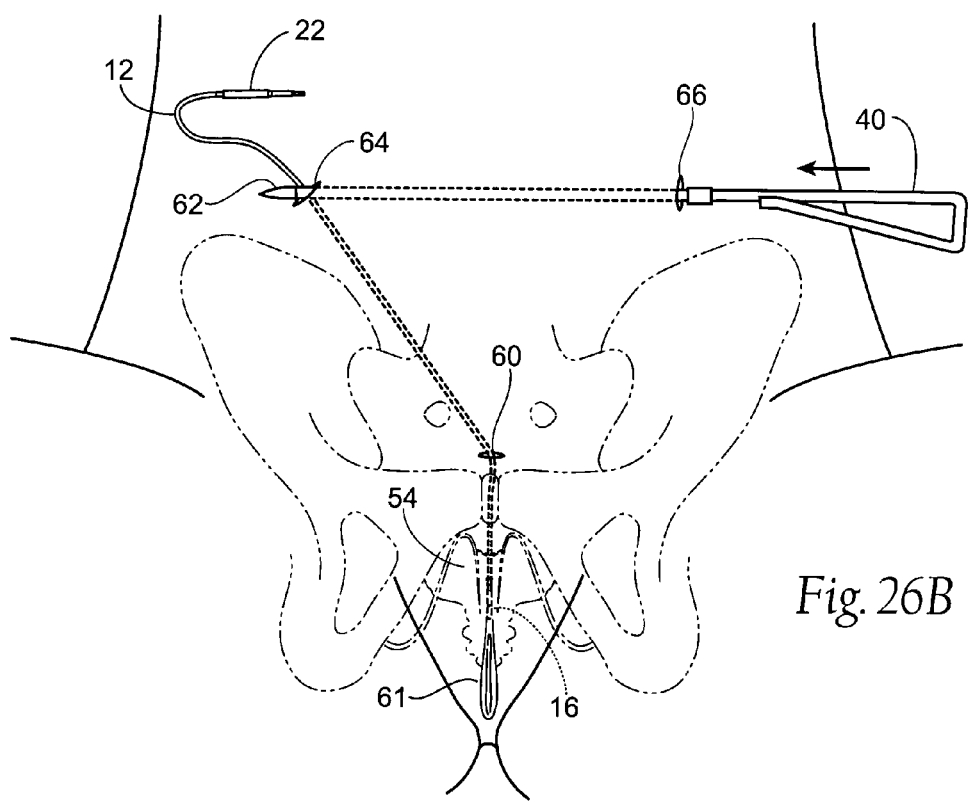
Figure 27A:
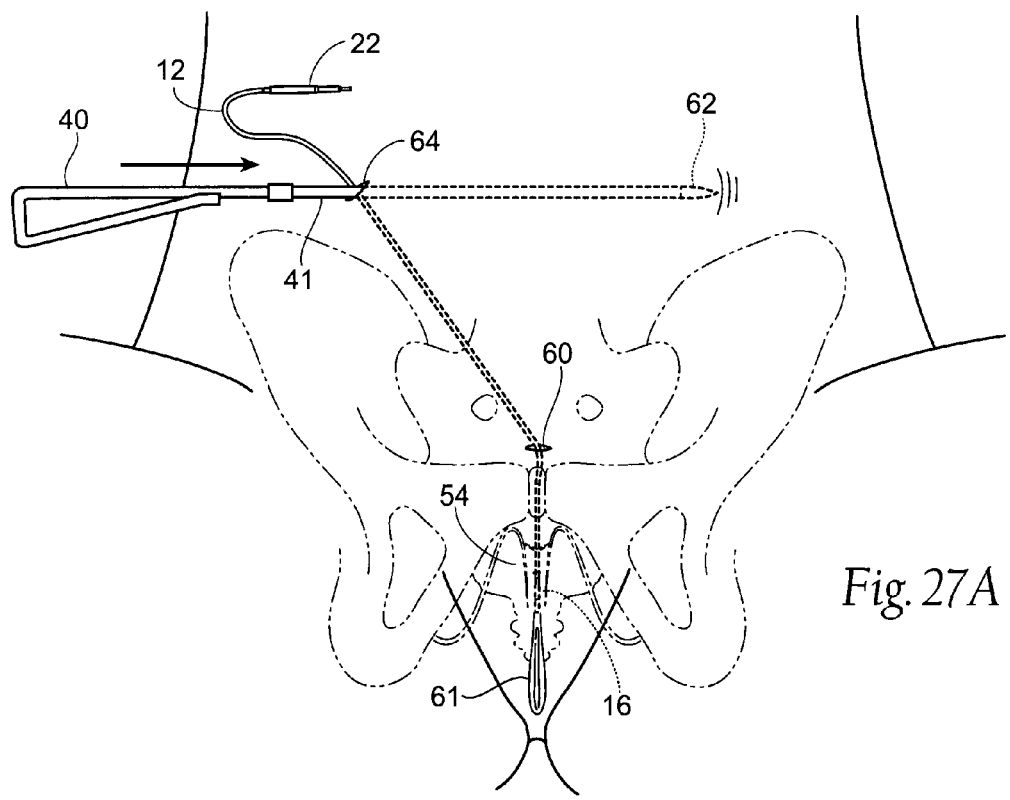
Figure 27B:
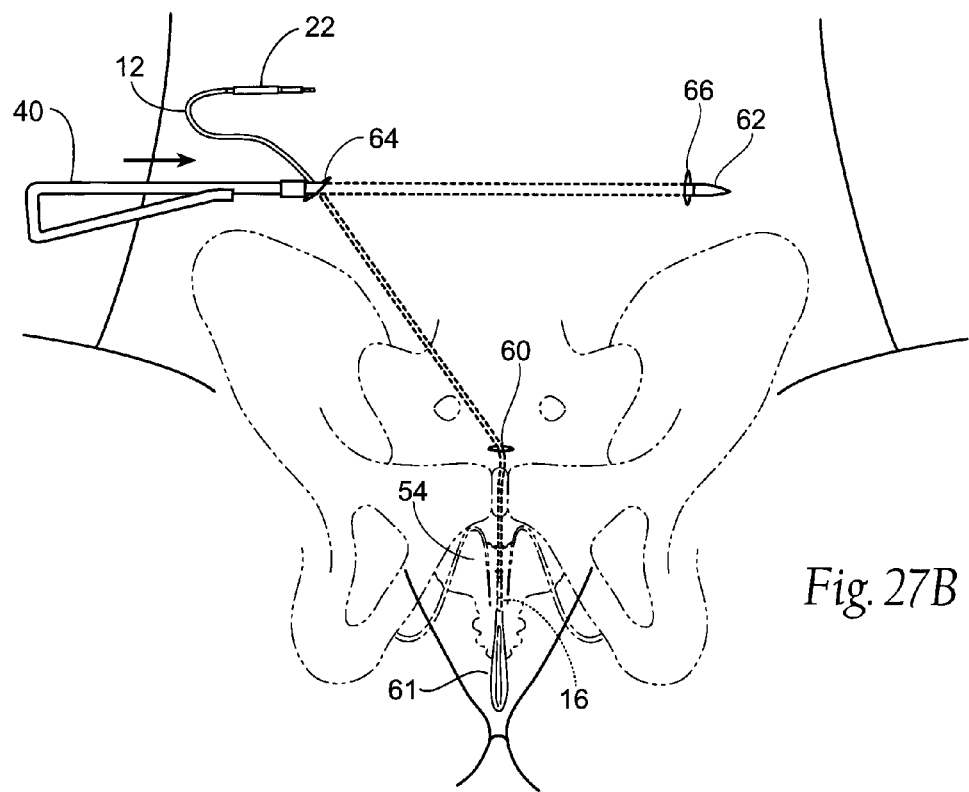
Figure 28:
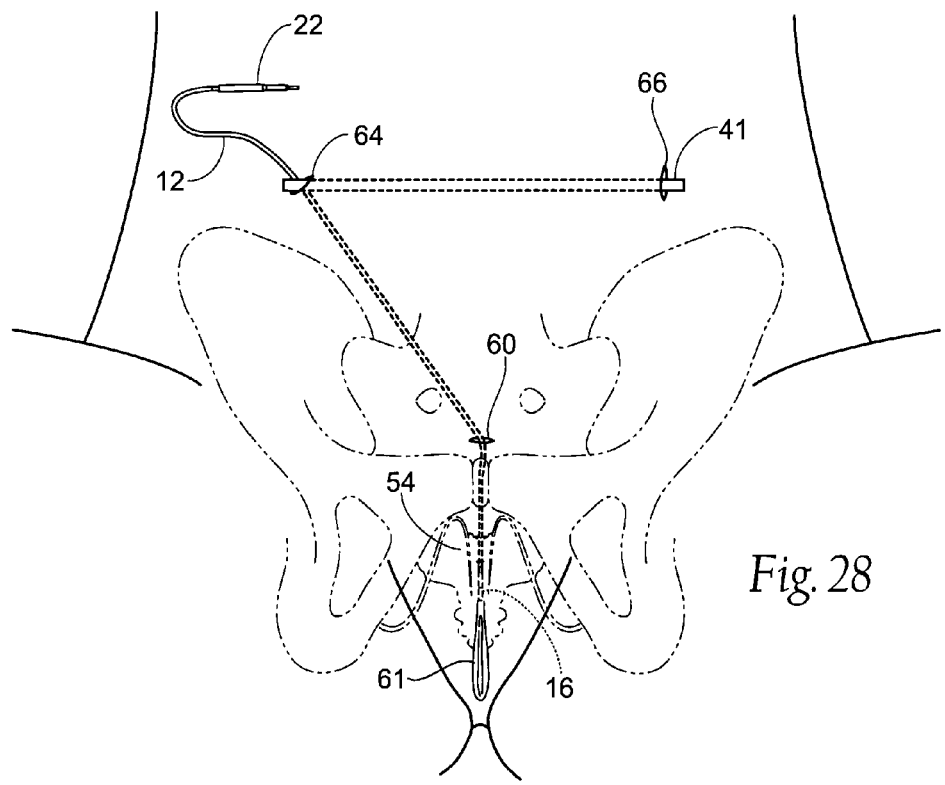

As FIG. 26A shows, a second incision 66 is made at a desired location. Next, a tunnel is made extending across the pelvis. The tunneling tool 40 with sharp tip 62 and sleeve 41 (shown in FIG. 2) is introduced through the second incision site 66 toward the pocket incision site 64, followed by passing the tip of the tunneling tool 40 through the incision 64 (see FIG. 26B). It is to be appreciated that the tunneling tool 40 may also be introduced through the pocket incision site 64 and tunneled to and through the second incision site 66, as shown in FIGS. 27A and 27B.

Figure 29:
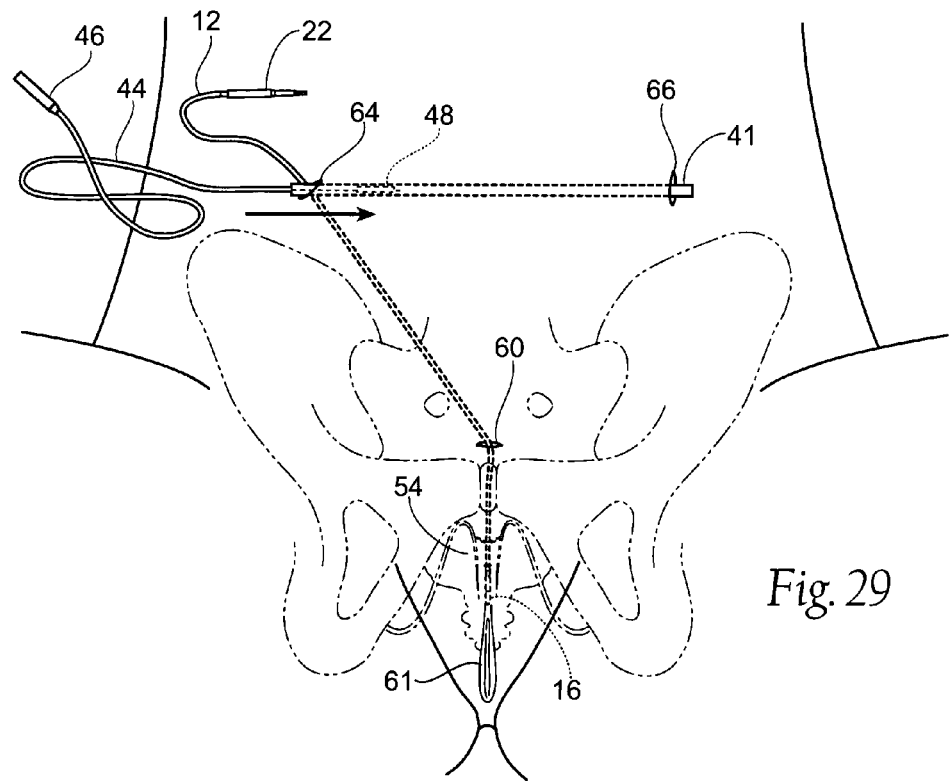
Figure 30:
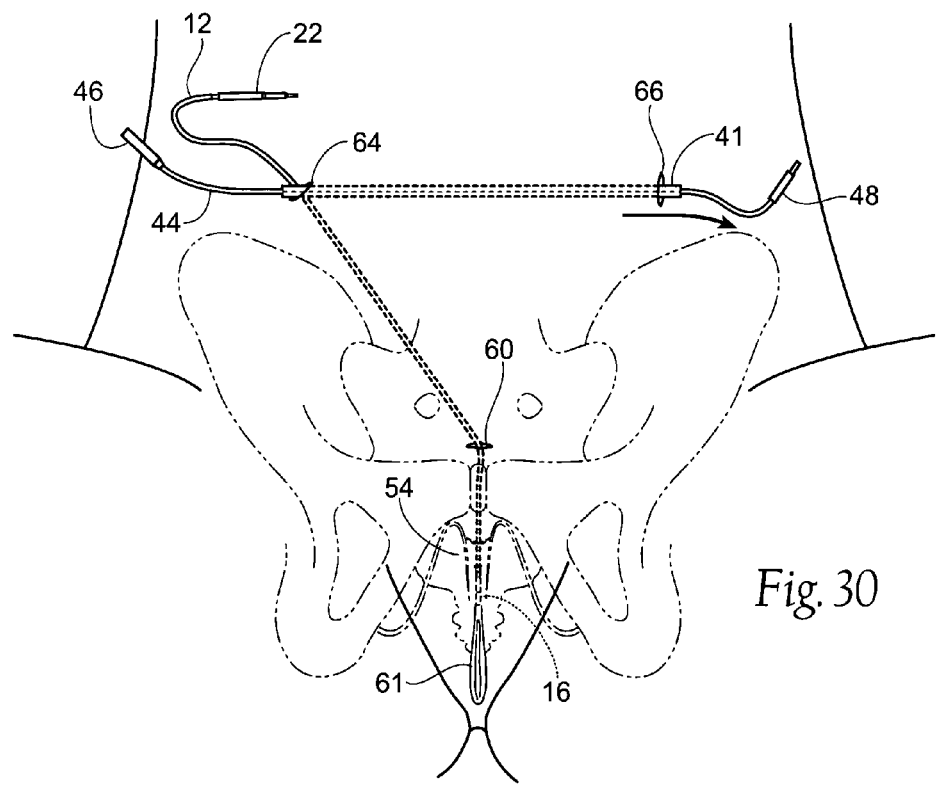

Removal of the tunneling tool 40 leaves the sleeve 41 in place (see FIG. 28), and allows the physician to pass the percutaneous extension cable 44 from the pocket incision site 64 through the sleeve 41 to the second incision site 66, followed by removal of the sleeve (see FIGS. 29 and 30). The plug 22 on the lead 12 can now be connected to the plug 46 on the percutaneous extension cable 44, and the connection can be placed through the incision 64 and under the skin (see FIG. 32).

Figure 31:
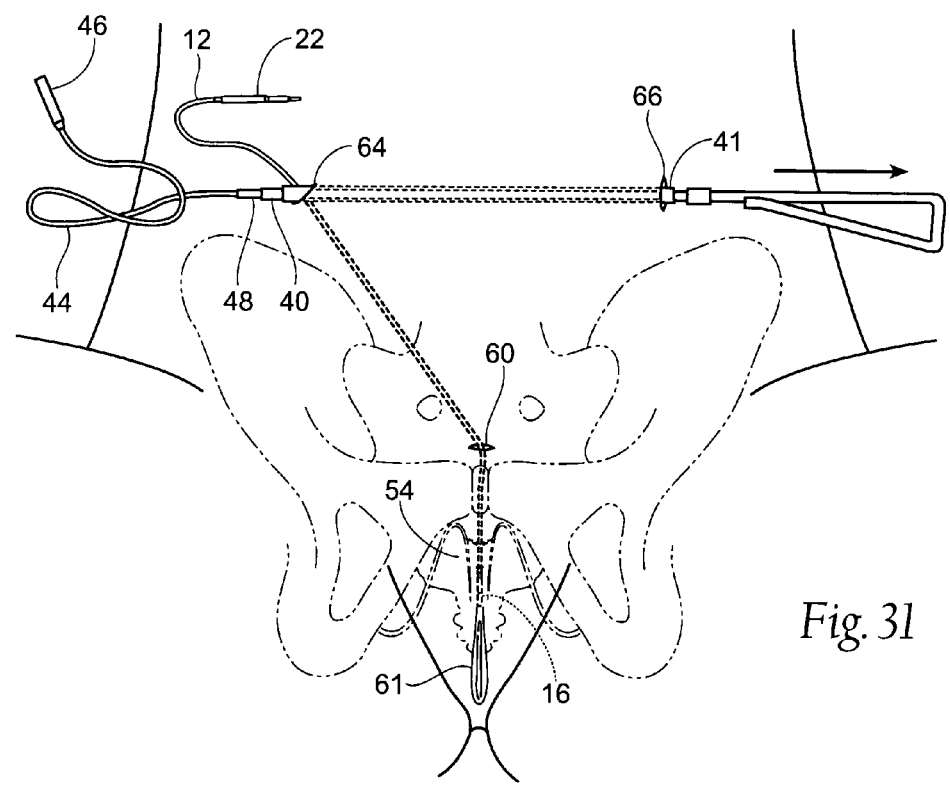
Figure 32:
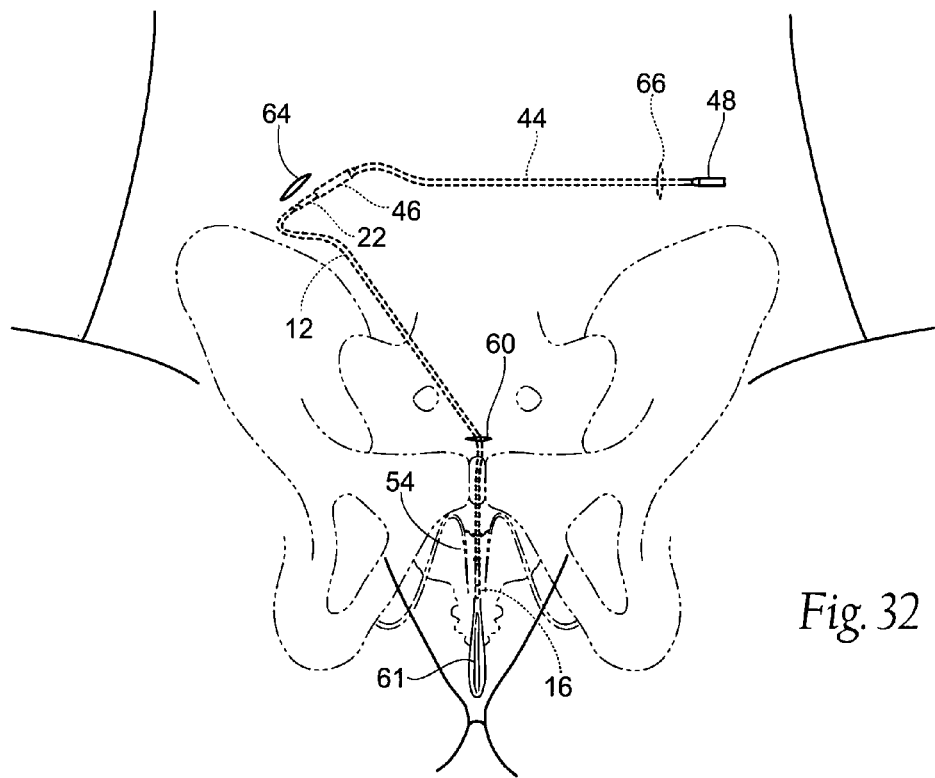

If the physician experiences resistance in pushing the percutaneous extension cable 44, the plug 48 on the percutaneous extension cable 44 can be attached to the tunneling tool 40 and pulled through the sleeve 41 (see FIG. 31). The tunneling tool 40 with the sharp tip 62 removed is reinserted into the sleeve 41 at the second incision site 66 and pushed until the tip exits at the pocket incision site 64. The plug 48 of the percutaneous extension cable 44 is attached to the tunneling tool 40, and the tunneling tool and the plug 48 of the percutaneous extension cable 44 are retracted out the second incision site 66.

In this configuration, should infection occur in the region where the percutaneous extension cable 44 extends from the skin (second incision site 66), the infection occurs away from the region where the pocket 56 for the implanted pulse generator 18 is to be formed (i.e., at the pocket incision site 64). The pocket incision site 64 and the lead tunnel all the way to the electrode 16 are thereby shielded from channel infection during the first stage, in anticipation of forming a sterile pocket 56 for the implantable generator in the second stage.

It should be appreciated that, in an alternative technique, the tip 62 of the tunneling tool 40 may be removed, and the percutaneous extension cable 44 is passed through an open lumen of the tunneling tool 40 to the second incision site. Withdrawal of the tunneling tool 40 delivers the plug 48 of the percutaneous extension cable 44 through the second incision 66 into the procedural field.

Figure 33:
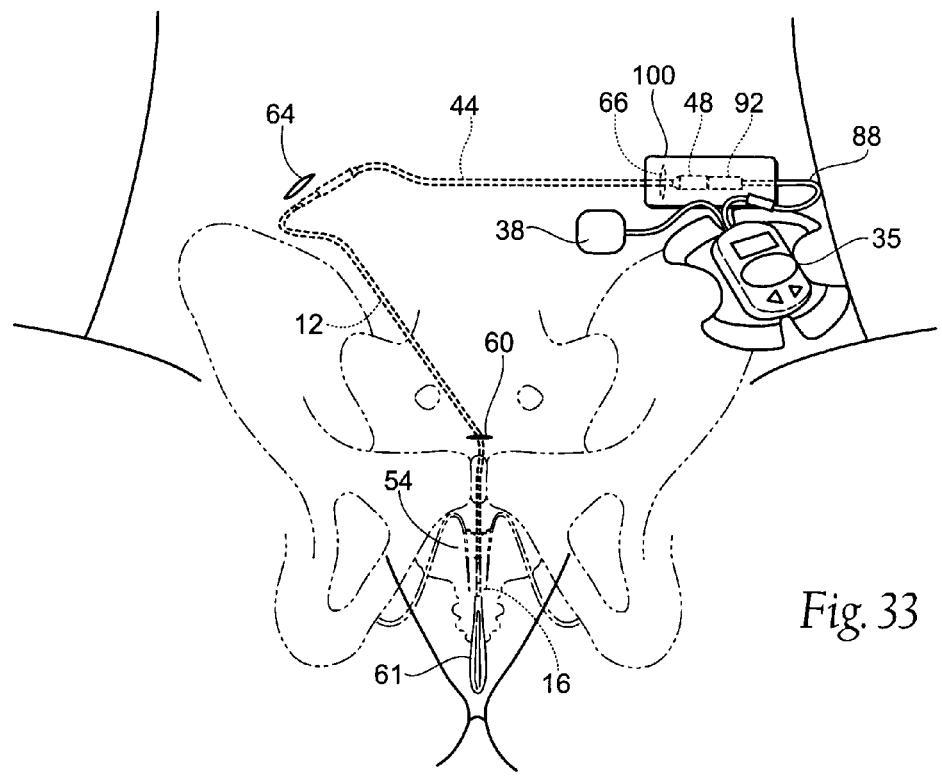

Once the plug 48 of the percutaneous extension cable 44 extends out of the second incision 66, the plug 48 is connected to the external extension cable 88 (as FIG. 33 shows). The connection is then secured externally to the skin with a piece of TEGADERM™ dressing or sterile tape 100, for example, which may also cover the incision site 66. Additional pieces may be used as necessary. The remainder of the percutaneous cable 44 is located under the skin and is free of exposure to outside contamination. The sterile tape 100 covering the exit site and the re-growth of tissue maintains this sterile barrier.

Figure 39:
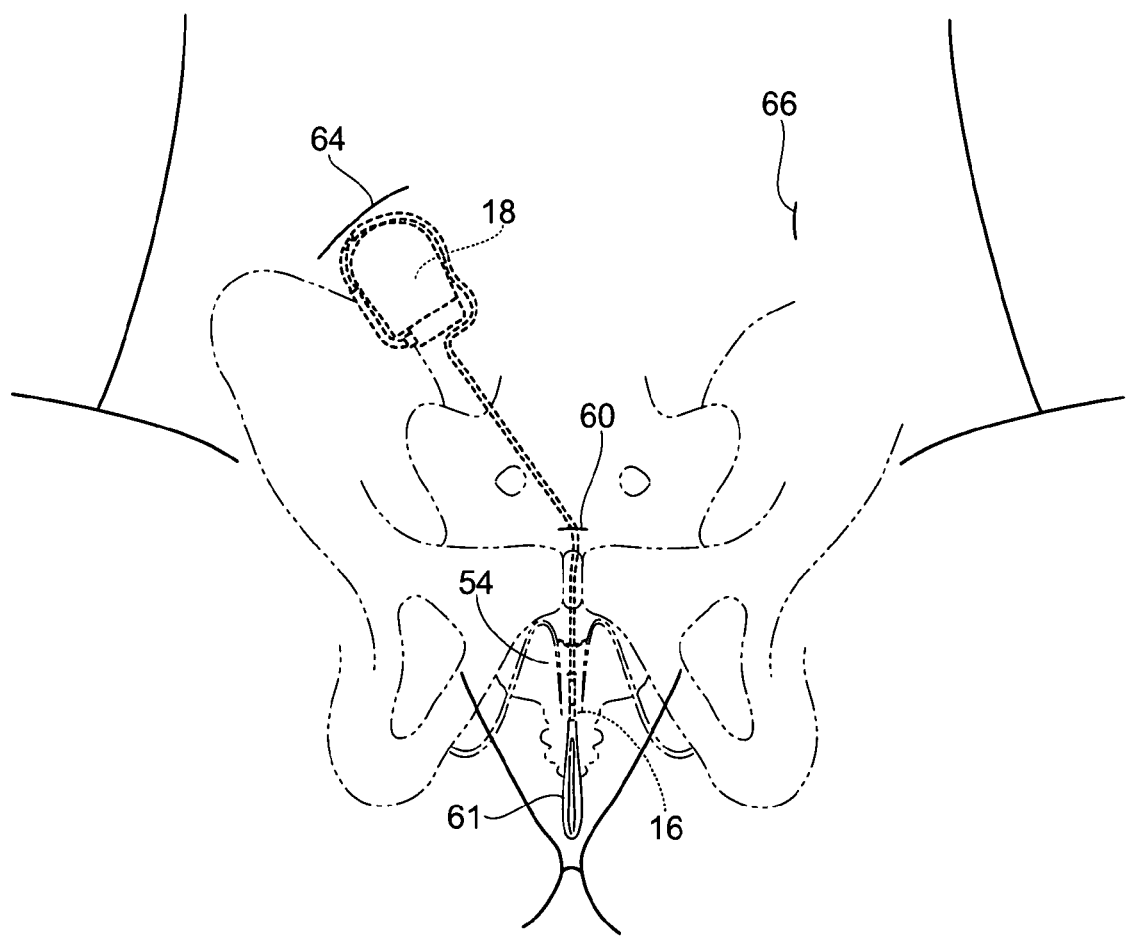

At the physician's discretion, some or all of the wound sites may be irrigated with irrigation solutions and closed using DERMABOND® glue, STERI-STRIP® material, or stitches of 4-0 VICRYL®, for example, as FIG. 39 shows.

For this first stage, an external pulse generator 35 can be used of the type described in U.S. Pat. No. 7,120,499, issued Oct. 10, 2006, and entitled "Portable Percutaneous Assemblies, Systems, and Methods for Providing Highly Selective Functional or Therapeutic Neurostimulation," which is incorporated herein by reference. Optionally, an external pulse generator 35 can be used of the type described in co-pending U.S. patent application Ser. No. 11/595,556, filed Nov. 10, 2006, and entitled "Portable Assemblies, Systems, and Methods for Providing Functional or Therapeutic Neurostimulation," which is also incorporated herein by reference.

Figure 3:
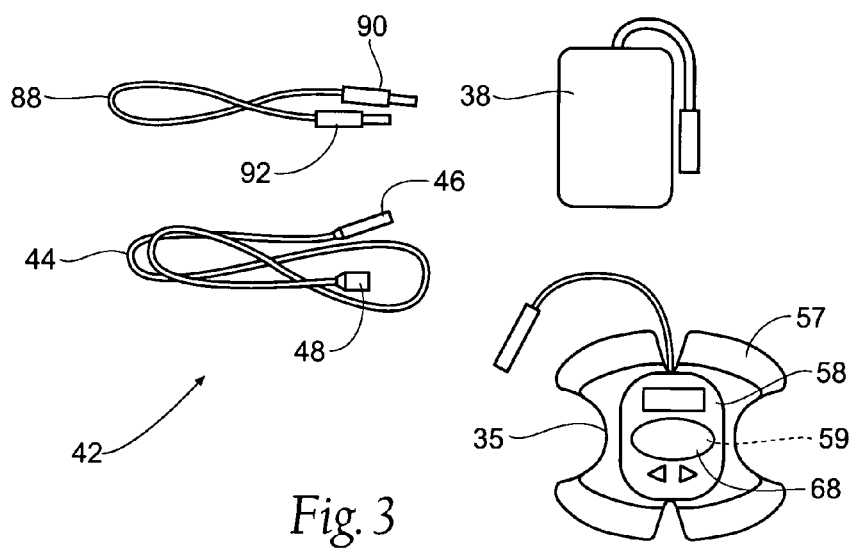
FIG. 3 is a plane view of test screening system that can used when the system shown in FIG. 1A is implanted in a two stage surgical procedure.

As shown in FIGS. 3 and 33, the device 35 may be electrically coupled to the percutaneous extension cable 44 through the extension cable 88. The external pulse generator 34 comprises a skin-worn patch or carrier 57. The carrier 57 can be readily carried, e.g., by use of a pressure-sensitive adhesive, without discomfort and without affecting body image on, for example, an arm, a leg, or torso of an individual. In place of worn on the skin, the patch or carrier may also be carried by the patient, or secured to clothing, a bed, or to movable devices to allow for patient mobility.

The carrier 57 may include a return electrode on its tissue facing surface, and carries a removable and replaceable electronics pod 58, which generates the desired electrical current patterns. The pod 58 houses microprocessor-based, programmable circuitry that generates stimulus currents, time or sequence stimulation pulses, monitors system status, and logs and monitors usage. The electronics pod 58 may be configured, if desired, to accept wireless RF based commands for both wireless programming and wireless patient control.

The electronics pod 58 also includes an electrode connection region (not shown), to physically and electrically couple the lead 12 to the circuitry of the electronics pod. The electronics pod 58 further includes a power input bay 59, to receive a small, lightweight, disposable power source 68, which can be released and replaced as prescribed. The power source 68 provides power to the electronics pod 58.

It is contemplated that, in a typical regime prescribed using the external pulse generator 35 in the test screening phase, an individual will be instructed to regularly remove and discard the power source 68 (e.g., about once a day, once a week, or as necessary), replacing it with a fresh power source. This arrangement simplifies meeting the power demands of the electronics pod 58 and easily allows the prescription of therapies of differing duration (e.g., apply stimulation every eight hours, every day, or once a week). The use of the external pulse generator 35 thereby parallels a normal, accustomed medication regime, with the power source 68 being replaced at a prescribed frequency similar to an individual administering a medication regime in pill form.

Figure 34:
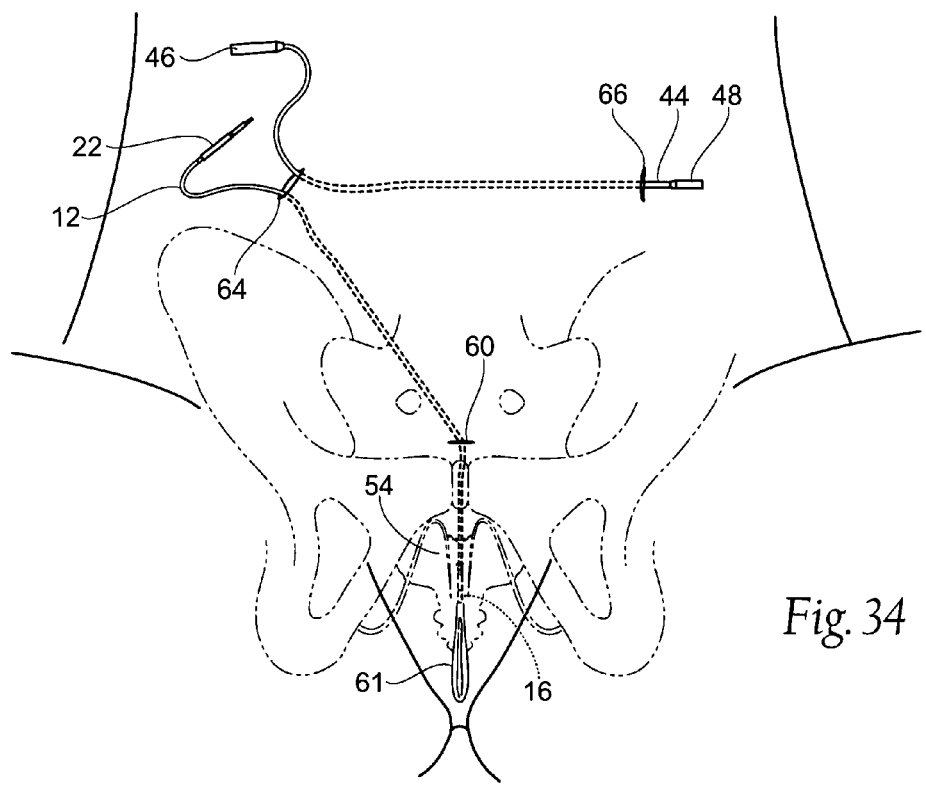

As previously described, the external pulse generator is coupled to the exposed plug 48 of the percutaneous extension cable through the external extension cable 88, as FIG. 33 shows. Optionally, a return patch electrode 38 may be placed on the skin and likewise coupled to the external pulse generator 35. The individual wears the external pulse generator 35 (e.g., in a belt holster or taped to the skin) and return patch electrode 38 (on the skin) for the prescribed test period. The external pulse generator 35 supplies the prescribed stimulation regime. If an improvement in urinary continence is achieved during the test phase, the second phase of the surgical procedure is scheduled to proceed.

b. The Second Stage:
Removing the Percutaneous Extension Cable and Implanting the Pulse Generator The same preoperative antibiotics and skin prep as previously described may be performed, again at the physician's discretion. In the second stage, the external pulse generator 35, return patch electrode 38 (if used), and external extension cable 88 are disconnected from the percutaneous extension cable 44, and may be discarded. Under MAC and/or local anesthesia, the incision 64 is reopened. As shown in FIG. 34, the connection between the percutaneous extension cable 44 and lead 12 is removed from the pocket incision 64 and disconnected.

Forming the Pulse Generator Pocket

Figure 35:
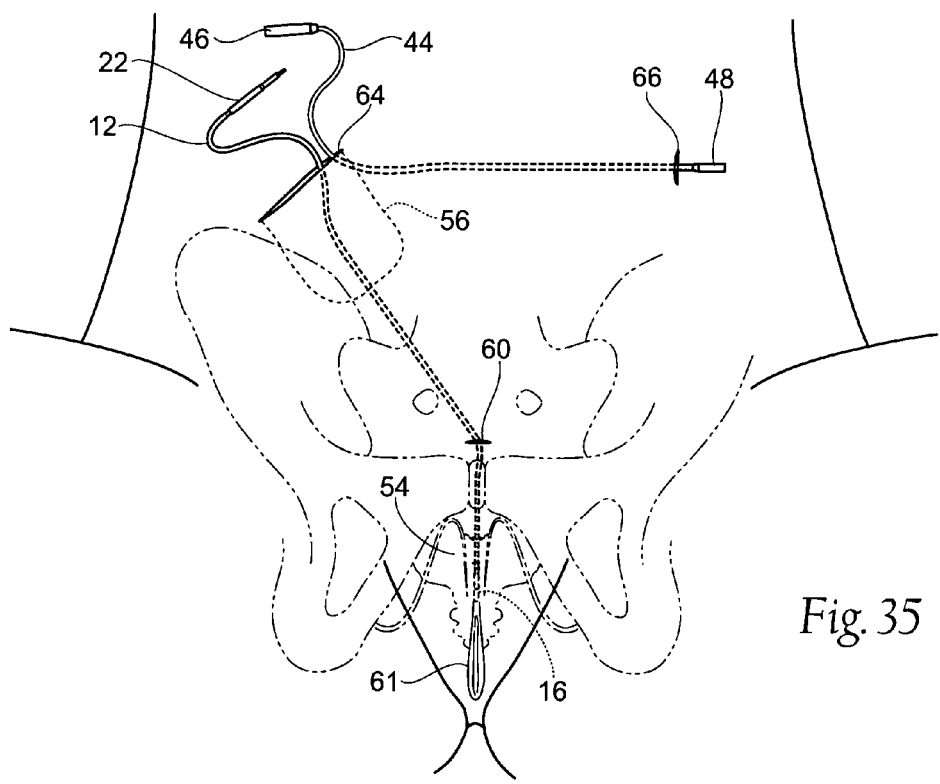

The pocket incision 64 may need to be enlarged to form a subcutaneous pocket 56 to accept the pulse generator 18. The incision 64 is made large enough to accept the index or dissecting finger of the implant physician. As FIG. 35 shows, the subcutaneous pocket 56 is made to accept the pulse generator 18 using blunt dissection techniques of the subcutaneous tissues. The axis of the pocket 56 may follow the direction of the dermatomal skin line and the entrance site of the lead 12/electrode 16.

Connecting the Lead to the Pulse Generator

Prior to removing the pulse generator 18 from its sterile package 110, the clinical programmer 52 is used to turn the pulse generator on and wirelessly communicate with the pulse generator to confirm proper operation. Once operation of the pulse generator is confirmed, and the lead 12 has been disconnected from the percutaneous extension cable 44, the plug 22 can be connected to the connector 14 on the pulse generator 18. A set screw 23 is provided on the pulse generator 18 to positively secure the plug 22 within the connector 14. The physician inserts the plug 22 into the connector 14, and then, using the torque tool 24 provided, tightens the set screw 23 to secure the lead 12 to the pulse generator 18 (see FIGS. 36A and 36B).

Implanting the Pulse Generator

Figure 36A:
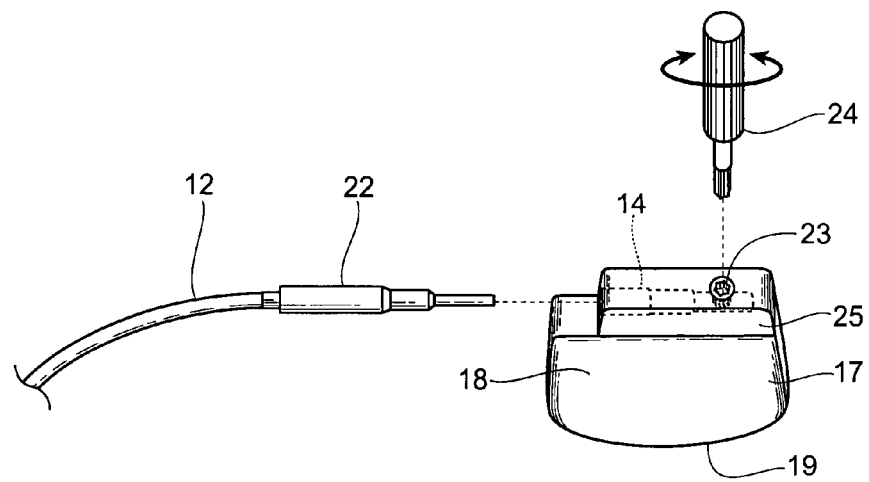
Figure 36B:
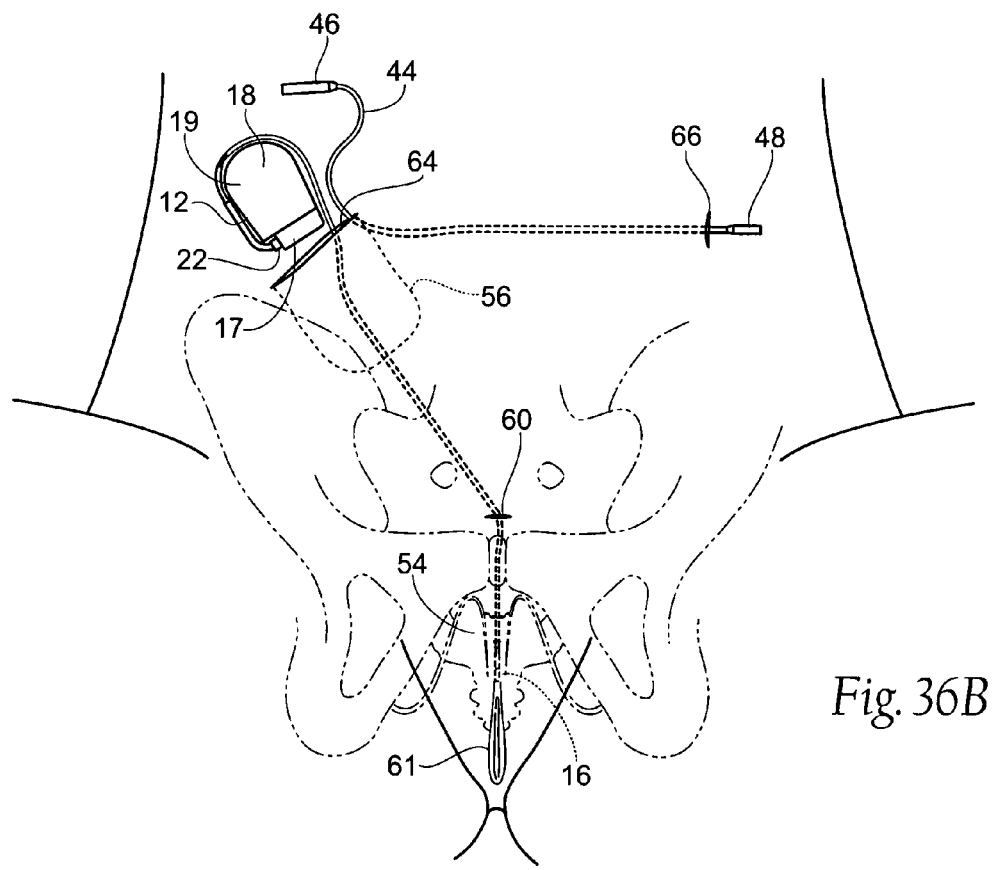

Once the lead 12 has been connected to the pulse generator 18, the lead 12 and pulse generator can be placed into the pocket 56. The pulse generator 18 is desirably pear or teardrop shaped with a small or narrow end 17 and a larger or wider end 19, with a header 25 coupled to the narrow end 17. As FIGS. 36B and 37 show, this geometry allows the narrow end 17 of the pulse generator 18 (including the header 25), to be placed into the skin pocket 56 first, with the wider end 19 being pushed in last.

Figure 37:
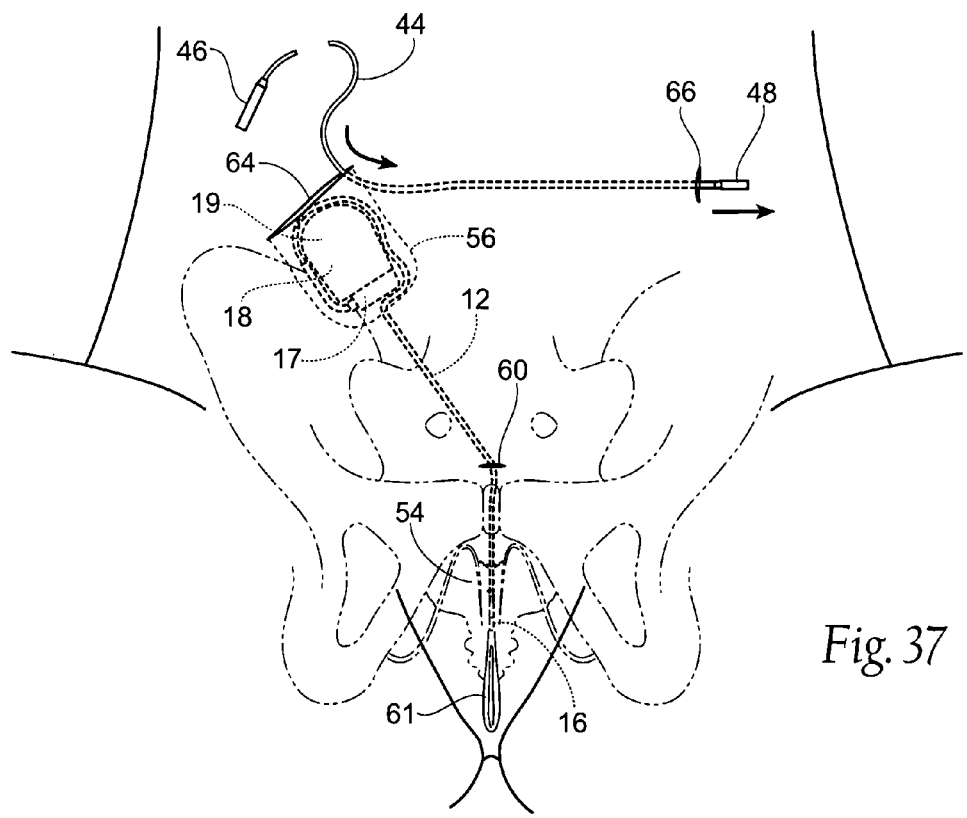

Either prior to or after placing the pulse generator 18 into the pocket 56, the receptacle 46 on the proximal end of the percutaneous extension cable 44 may be cut off to allow the percutaneous extension cable 44 to be removed by pulling the cable 44 through the second incision 66, as FIG. 37 shows. The percutaneous extension cable may be discarded.

The external facing surface of the implanted pulse generator 18 is desirably located about 0.5 cm to about 2.0 cm from the external surface of the skin (as can be seen in FIG. 1A), and more desirably about 1.0 cm from the external surface of the skin. The cable is oriented with an open loop of cable around the pulse generator (not across the pulse generator) to allow for motion of the abdominal contents without transmitting forces along the cable and lead (see FIGS. 36 and 37). The external facing surface may include etching to help the physician identify which side is the intended external facing surface. The patient may be asked to move, i.e., sit up and lay back down, to be certain that the pulse generator 18 is properly positioned within the pocket 56 and at the desired implant depth.

Figure 38:
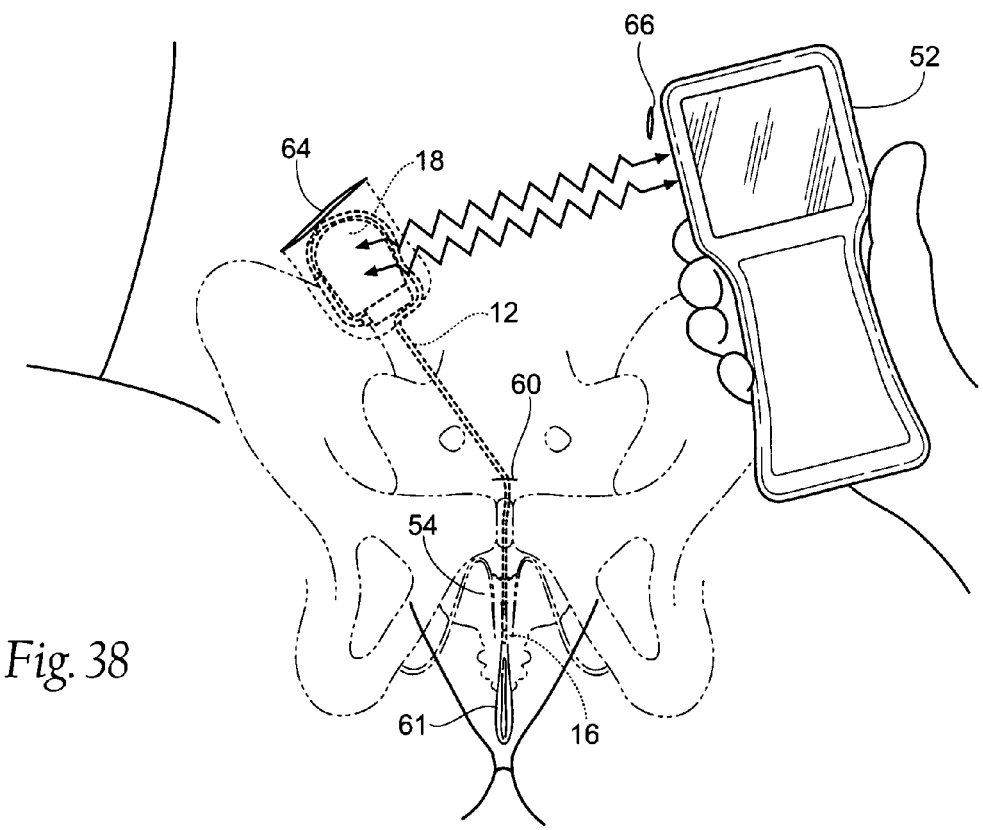

As can be seen in FIGS. 38 and 39, the clinical programmer 52 is again used to turn on the pulse generator 18 and to test the stimulus response. The clinical programmer would use wireless telemetry and may be located either inside or outside of the surgical field, e.g., up to about three to six feet away from the implanted pulse generator 18.

Once proper pulse generator operation is confirmed, the incision site 64 is closed. At the physician's discretion, the incision site 64 may be irrigated with irrigation solutions (e.g., ½ strength betadine or Hibiclens solution), and closed using DERMABOND® glue, STERI-STRIP® material, or stitches of 4-0 VICRYL®, for example, as FIG. 39 shows. Dressing is desirably applied for about twenty-four hours. The incisions are desirably kept dry for forty-eight hours.

2. Single Stage Surgical Procedure

The figures used to illustrate the steps of implanting the implant system 10 in a two stage surgical procedure will also be used to illustrate the steps of implanting the implant system 10 in a single stage surgical procedure. The single stage surgical procedure eliminates the test screening phase (i.e., temporary use of the external pulse generator 35), and in the single surgical procedure implants the pulse generator 18 in the pulse generator pocket 56.

Locating the Lead/Electrode

The same preoperative antibiotics and skin prep as previously described are performed. Under MAC and/or local anesthesia, the electrode 16/lead 12 is located as previously described for the first stage of the two stage procedure, and as shown in FIGS. 9 through 19.

Tunneling the Lead

Having implanted the lead/electrode, a subcutaneous tunnel is formed for connecting the lead 12 to the pulse generator 18. The tunneling tool 40 is manipulated by the physician to route the lead 12 subcutaneously to the pocket site 56 where the pulse generator 18 is to be implanted. The lead 12 is tunneled as previously described for the first stage of the two stage procedure, and as shown in FIGS. 20 through 25.

Forming the Pulse Generator Pocket

After placement of the lead 12 as FIG. 24 shows, the pocket incision 64 is enlarged to form a subcutaneous pocket 56 to accept the pulse generator 18 using blunt dissection techniques of the subcutaneous tissues, as previously described for the second stage of the two stage procedure, and as shown in FIG. 35.

Connecting the Lead to the Pulse Generator

With the pocket 56 formed, and the lead 12 and plug 22 delivered into the procedural field, the lead can now be connected to the pulse generator 18. The lead 12 is connected to the pulse generator 18 as previously described for the second stage of the two stage procedure, and as shown in FIGS. 36A and 36B.

Implanting the Pulse Generator

Once the lead 12 has been connected to the pulse generator 18, the lead 12 and pulse generator can be placed into the pocket 56 as previously described for the second stage of the two stage procedure, and as shown in FIGS. 37 through 39.

At the physician's discretion, some or all of the wound sites may be irrigated with irrigation solutions (e.g., ½ strength betadine or Hibiclens solution), and closed using DERMA-BOND® glue, STERI-STRIP® material, or stitches of 4-0 VICRYL®, for example, as FIG. 39 shows. Dressing is desirably applied for about twenty-four hours. The incisions are desirably kept dry for forty-eight hours.

Using the surgical tool system 28, the implant system 10 can be implanted in the manner shown in FIGS. 5A and 5B.

III. Features of the Lead and Electrode

A. Implantation in Adipose Tissue

Neurostimulation leads and electrodes that may be well suited for implantation in muscle tissue are not well suited for implantation in soft adipose tissue 54 in the targeted location at or near the pubic symphysis. This is because adipose tissue 54 is unlike muscle tissue, and also because the vascularization and innervation of tissue at or near the pubic symphysis is unlike tissue in a muscle mass. Muscular tissue is formed by tough bundles of fibers with intermediate areolar tissue. The fibers consist of a contractile substance enclosed in a tubular sheath. The fibers lend bulk, density, and strength to muscle tissue that are not found in soft adipose tissue 54. Muscles are also not innervated with sensory nerves or highly vascularized with blood vessels to the extent found in the pubic region of the body.

Figure 40:
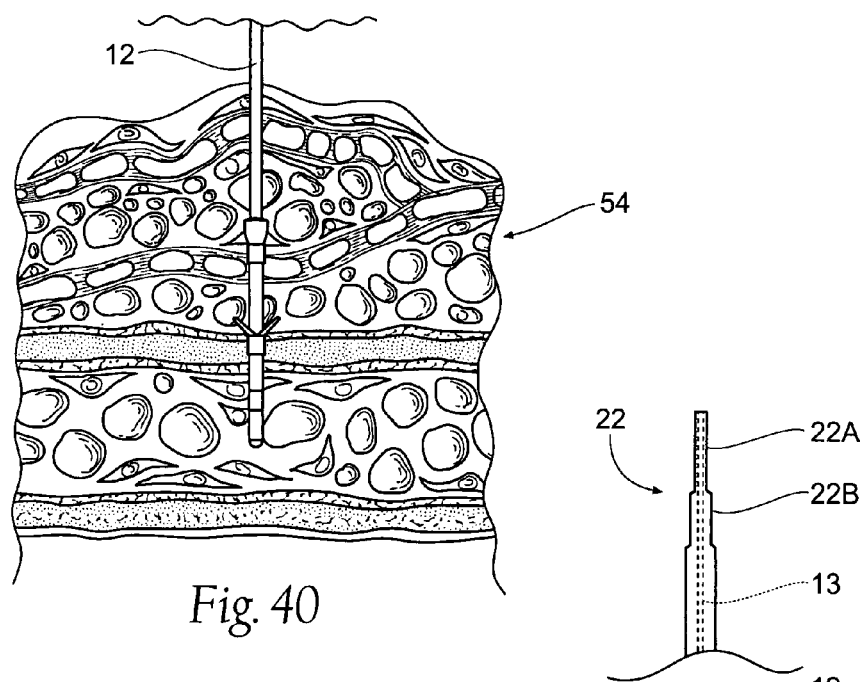
FIGS. 40 and 41 are anatomic section views of the adipose tissue region shown in FIG. 39 with a single lead and electrode associated with the system shown in FIG. 1A, after having been implanted.

Adipose tissue 54 (see FIG. 40) consists of small vesicles, called fat-cells, lodged in the meshes of highly vascularized areolar tissue containing minute veins, minute arteries, and capillary blood vessels. The fat-cells vary in size, but are about the average diameter of 1/500 of an inch. They are formed of an exceedingly delicate protoplasmic membrane, filled with fatty matter, which is liquid during life and turns solid after death. They are round or spherical where they have not been subject to pressure; otherwise they assume a more or less angular outline. The fat-cells are contained in clusters in the areolae of fine connective tissue, and are held together mainly by a network of capillary blood vessels, which are distributed to them.

Figure 41:
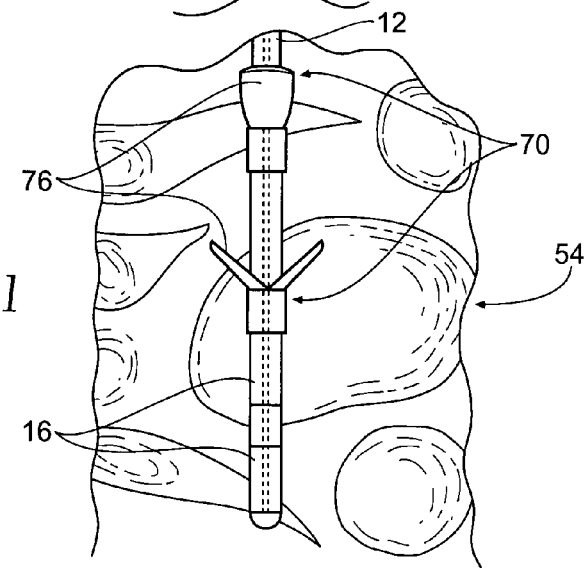

The lead 12 and electrode 16 are sized and configured to be inserted into and to rest in soft adipose tissue 54 (see FIGS. 40 and 41) in the lower abdomen without causing pain or discomfort or impact body image. Desirably, the lead 12 and electrode 16 can be inserted using the small (e.g., smaller than 16 gauge) introducer sleeve 32 with minimal tissue trauma. The lead 12 and electrode 16 are formed from a biocompatible and electrochemically suitable material and possess no sharp features that can irritate tissue during extended use. Furthermore, the lead 12 and electrode 16 possess mechanical characteristics including mechanical compliance (flexibility) along their axis (axially), as well as perpendicular to their axis (radially), and unable to transmit torque, to flexibly respond to dynamic stretching, bending, and crushing forces that can be encountered within soft, mobile adipose tissue 54 in this body region without damage or breakage, and to accommodate relative movement of the pulse generator coupled to the lead 12 without imposing force or torque to the electrode 16 which tends to dislodge the electrode.

Furthermore, the lead 12 and electrode 16 desirably include an anchoring means 70 for providing retention strength to resist migration within or extrusion from soft, mobile adipose tissue 54 in this body region in response to force conditions normally encountered during periods of extended use (see FIGS. 42A and 42B). In addition, the anchoring means 70 is desirably sized and configured to permit the electrode 16 position to be adjusted easily during insertion, allowing placement at the optimal location where bilateral stimulation of the left and right branches of the genital nerves occurs. The anchoring means 70 functions to hold the electrode at the implanted location despite the motion of the tissue and small forces transmitted by the lead due to relative motion of the connected pulse generator due to changes in body posture or external forces applied to the abdomen. However, the anchoring means 70 should allow reliable release of the electrode 16 at higher force levels, to permit withdrawal of the implanted electrode 16 by purposeful pulling on the lead 12 at such higher force levels, without breaking or leaving fragments, should removal of the implanted electrode 16 be desired.

B. The Lead

Figure 43:
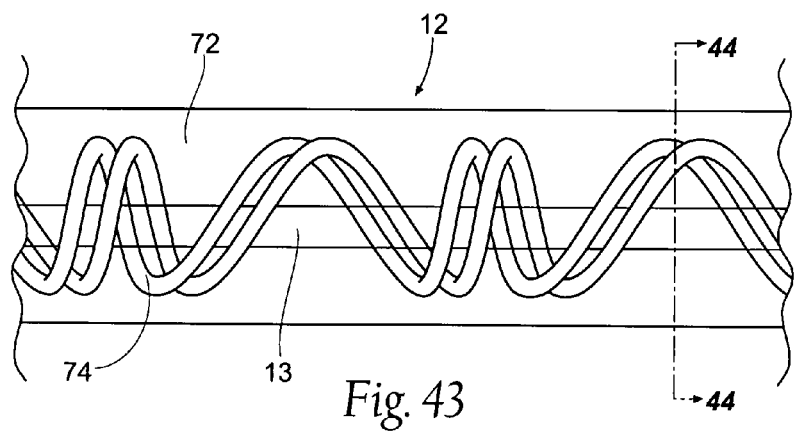
FIG. 43 is a side interior view of a representative embodiment of a lead of the type shown in FIGS. 42A and 42B.
Figure 44:
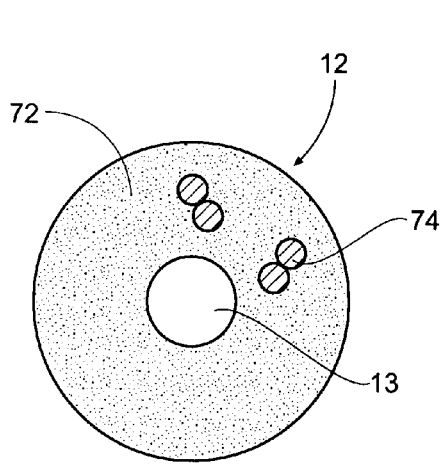
FIG. 44 is an end section view of the lead taken generally along line 44-44 in FIG. 43.

FIGS. 43 and 44 show a representative embodiment of a lead 12 that provide the foregoing features. The implantable lead 12 comprises a molded or extruded component 72, which encapsulates one or more stranded or solid wire elements 74, and includes the connector 22 (shown in FIG. 41). The wire element may be bifilar, as shown in FIG. 44, and may be constructed of coiled MP35N nickel-cobalt wire or wires that have been coated in polyurethane. In a representative embodiment with two electrically conductive surfaces 16 (as described below), one wire element 74 is coupled to the distal electrode 16 and the pin 22A of the connector 22. A second wire element 74 is coupled to the proximal electrode 16 and the ring 22B on the connector 22. The molded or extruded lead 12 can have an outside diameter as small as about one (1) mm, and desirably about 1.9 mm. The lead 12 may also include an inner lumen 13 having a diameter about 0.2 millimeters to about 0.5 millimeters, and desirably about 0.35 millimeters. The lead 12 may be approximately 10 cm to 40 cm in length. The lead 12 provides electrical continuity between the connector 22 and the electrode 16.

The coil's pitch can be constant or, as FIG. 43 shows, the coil's pitch can alternate from high to low spacing to allow for flexibility in both compression and tension. The tight pitch will allow for movement in tension, while the open pitch will allow for movement in compression.

A standard IS-1 or similar type connector 22 at the proximal end provides electrical continuity and mechanical attachment to the pulse generator 18. The lead 12 and connector 22 all may include provisions (e.g., lumen 13) for a guidewire that passes through these components and the length of the lead 12 to the conductive electrode 16 at the distal end.

C. The Electrode

The electrode 16 may comprise one or more electrically conductive surfaces. Two conductive surfaces are show in FIGS. 42A and 42B. The two conductive surfaces can be used either A) as one two individual stimulating (cathodic) electrodes in a monopolar configuration using the metal case of the pulse generator 18 as the return (anodic) electrode or B) either the distal or proximal conductive surface as a individual stimulating (cathodic) electrode in a monopolar configuration using the metal case of the pulse generator 18 as the return (anodic) electrode or C) in bipolar configuration with one electrode functioning as the stimulating (cathodic) electrode and the other as the return (anodic) electrode.

In general, bipolar stimulation is more specific than monopolar stimulation—the area of stimulation is much smaller—which is good if the electrode 16 is close to the target nerve. But if the electrode 16 is farther from the target nerve, then a monopolar configuration could be used because with the pulse generator 18 acting as the return electrode, activation of the nerve is less sensitive to exact placement than with a bipolar configuration.

In use, a physician may first attempt to place the electrode 16 close to the left and right branches of the dorsal genital nerve so that it could be used in a bipolar configuration, but if bipolar stimulation failed to activate the nerve, then the electrode 16 could be switched to a monopolar configuration. Two separate conductive surfaces on the electrode 16 provide an advantage because if one conductive surface fails to activate the target nerve because it is too far from the nerve, then stimulation with the second conductive surface could be tried, which might be closer to the target nerve. Without the second conductive surface, a physician would have to reposition the electrode to try to get closer to the target nerve.

The electrode 16, or electrically conductive surface or surfaces, can be formed from PtIr (platinum-iridium) or, alternatively, 316L stainless steel. Each electrode 16 possess a conductive surface of approximately 10 mm$^2$-20 mm$^2$ and desirably about 16.5 mm$^2$. This surface area provides current densities up to 2 mA/mm2 with per pulse charge densities less than about 0.5 μC/mm2. These dimensions and materials deliver a charge safely within the stimulation levels supplied by the pulse generator 18.

Each conductive surface has an axial length in the range of about three to five millimeters in length and desirably about four millimeters. When two or more conductive surfaces are used, either in the monopolar or bipolar configurations as described, there will be an axial spacing between the conductive surfaces in the range of 1.5 to 2.5 millimeters, and desirably about two millimeters.

D. The Anchoring Means

In the illustrated embodiment (see FIGS. 42A and 42B), the lead is anchored by anchoring means 70 specifically designed to secure the electrode 16 in the layer of adipose tissue in electrical proximity to the left and right branches of the dorsal genital nerve, without the support of muscle tissue. The anchoring means 70 takes the form of an array of shovel-like paddles or scallops 76 proximal to the proximal-most electrode 16 (although a paddle 76 or paddles could also be proximal to the distal most electrode 16, or could also be distal to the distal most electrode 16). The paddles 76 as shown and described are sized and configured so they will not cut or score the surrounding tissue.

The paddles 76 are desirably present relatively large, generally planar surfaces, and are placed in multiple rows axially along the distal portion of lead 12. The paddles 76 may also be somewhat arcuate as well, or a combination of arcuate and planar surfaces. A row of paddles 76 comprises two paddles 76 spaced 180 degrees apart. The paddles 76 may have an axial spacing between rows of paddles in the range of six to fourteen millimeters, with the most distal row of paddles 76 adjacent to the proximal electrode, and each row may be spaced apart 90 degrees. The paddles 76 are normally biased toward a radially outward condition into tissue.

In this condition, the large surface area and orientation of the paddles 76 allow the lead 12 to resist dislodgement or migration of the electrode 16 out of the correct location in the surrounding tissue. In the illustrated embodiment, the paddles 76 are biased toward a proximal-pointing orientation, to better resist proximal migration of the electrode 16 with lead tension. The paddles 76 are desirably made from a polymer material, e.g., high durometer silicone, polyurethane, or polypropylene, bonded to or molded with the lead 12.

The paddles 76 are not stiff, i.e., they are generally pliant, and can be deflected toward a distal direction in response to exerting a pulling force on the lead 12 at a threshold axial force level, which is greater than expected day-to-day axial forces. The paddles 76 are sized and configured to yield during proximal passage through tissue in result to such forces, causing minimal tissue trauma, and without breaking or leaving fragments, despite the possible presence of some degree of tissue in-growth. This feature permits the withdrawal of the implanted electrode 16, if desired, by purposeful pulling on the lead 12 at the higher axial force level.

Desirably, and as previously described, the anchoring means 70 is prevented from fully engaging body tissue until after the electrode 16 has been deployed. The electrode 16 is not deployed until after it has been correctly located during the implantation (installation) process.

Figure 45:
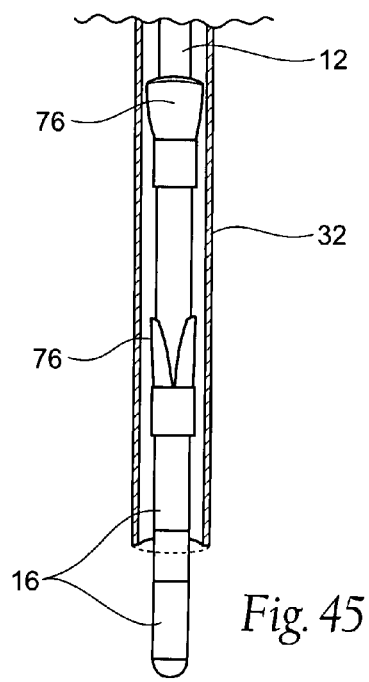
FIG. 45 is an elevation view, in section, of a lead and electrode of the type shown in FIGS. 34 and 35 residing within an introducer sleeve for implantation in a targeted tissue region, the anchoring members being shown retracted within the sheath.

More particularly, and as previously described, the lead 12 and electrode 16 are intended to be percutaneously introduced through the sleeve 32 shown in FIG. 45. As shown in FIG. 45, the paddles 76 assume a collapsed condition against the lead 12 body when within the sleeve 32. In this condition, the paddles 76 are shielded from contact with tissue. Once the location is found, the sleeve 32 can be withdrawn, holding the lead 12 and electrode 16 stationary. Free of the sleeve 32, the paddles 76 spring open to assume their radially deployed condition in tissue, fixing the electrode 16 in the desired location. In the radially deployed condition, the paddles have a diameter (fully opened) of about four millimeters to about six millimeters, and desirably about 4.8 millimeters.

The lead has two ink markings 20, 21 to aid the physician in its proper placement. The most distal marking 20 (about 11 cm from the tip) aligns with the external edge of the introducer sleeve 32 when the tip of the lead is at the tip of the sleeve 32. The more proximal marking 21 (about 13 cm from the tip) aligns with the external edge of the sleeve 32 when the introducer has been retracted far enough to expose the tines 76. A central lumen 13 allows for guidewire 94 insertion and removal to facilitate lead placement. A funnel 95 may be included to aid in inserting the guidewire 94 into the lumen 13 in the lead 12.

The anchoring means 70 may be positioned about 10 millimeters from the distal tip of the lead, and when a second anchoring means 70 is used, the second anchoring means 70 may be about 20 millimeters from the distal tip of the lead.

The position of the electrode 16 relative to the anchoring means 70, and the use of the sleeve 32, allows for both advancement and retraction of the electrode delivery sleeve 32 during implantation while simultaneously delivering test stimulation. The sleeve 32 can be drawn back relative to the lead 12 to deploy the anchoring means 70, but only when the physician determines that the desired electrode location has been reached. The withdrawal of the sleeve 32 from the lead 12 causes the anchoring means 70 to deploy without changing the position of electrode 16 in the desired location (or allowing only a small and predictable, set motion of the electrode 16). Once the sleeve 32 is removed, the flexible, silicone-coated or polyurethane-coated lead 12 and electrode 16 are left implanted in the tissue.

IV. Extension Cables

FIGS. 46A through 47B show representative embodiments of extension cables 44 and 88 respectively. The percutaneous extension cable 44, as previously described, is sized and configured to be tunneled subcutaneously from the pocket site to a remote site where it exits the skin. The length of the percutaneous extension cable can vary depending on the anatomy of the patient, and location of the remote site. The percutaneous extension cable has a proximal and distal portion. The proximal portion 126 carries a standard female IS-1 receptacle 46 for connection to the industry-standard size plug on the end of the lead 12. The distal portion 128 of the percutaneous extension cable 44 carries a plug 48 that couples, e.g., screws, to the intermediate external extension cable 88, which itself couples to the external pulse generator 35.

Figure 46A:
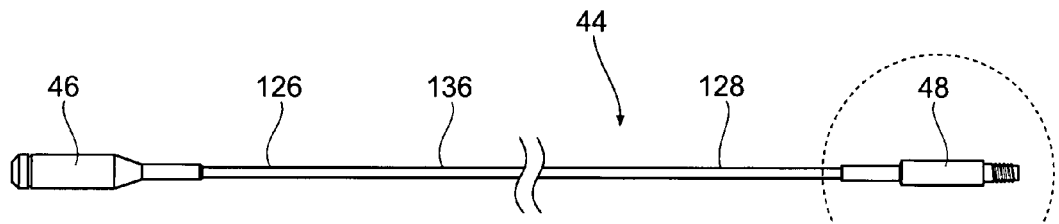
FIGS. 46A and 46B are side views in partial section of the percutaneous extension cable and associated connectors.
Figure 46B:
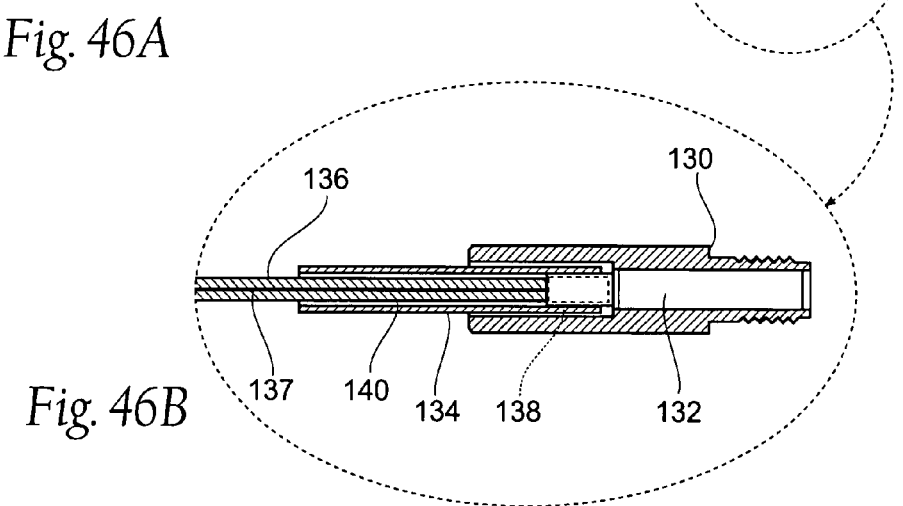

The plug 48 is sized and configured to comprise a touch-proof connector. As can be seen in FIG. 46B, the plug 48 includes a threaded socket housing 130. Within the threaded socket housing 130 is a crimp style socket 132 for receipt of the contact pin 152 from the external extension cable 88, i.e. the electrical connection is between the socket 132 in the plug 48 and the pin 152 in the connector 92. The threaded socket housing 130 and threaded pin housing 150 enclose the contacts, and provide the mechanical thread to align and connect the contacts. The socket 132 is recessed approximately 0.5 mm within the socket housing 130, which provides that connector with its touch proof designation feature (per EN 60601-1:1990 part 56.3.c). A strain relief 134 may be coupled to the proximal portion of the housing 130.

The percutaneous extension cable 44 also comprises a molded or extruded component 136, which encapsulates one or more stranded or solid wire elements 137, and electrically couples the receptacle 46 and the plug 48. The wire element 137 may be a solid or multifilament wire, and may be constructed of coiled MP35N nickel-cobalt wire or 316L stainless steel wires that have been coated in polyurethane or a fluoropolymer such as perfluoroalkoxy (PFA), or other wire configurations known in the art.

A shim 138 may comprise a stainless steel wire shim, and may be inserted into the socket 132 with the deinsulated wire element 137 and crimped within the socket. An adhesive 140 (e.g., silicon), may be used to fill the space between the strain relief 134 and the extruded component 136. An adhesive may also be used to bond the socket 132 within the housing 130.

Figure 47A:
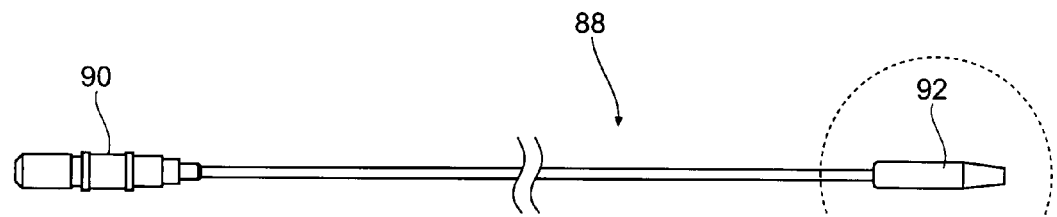
FIGS. 47A and 47B are side views in partial section of the external extension cable and associated connectors.
Figure 47B:
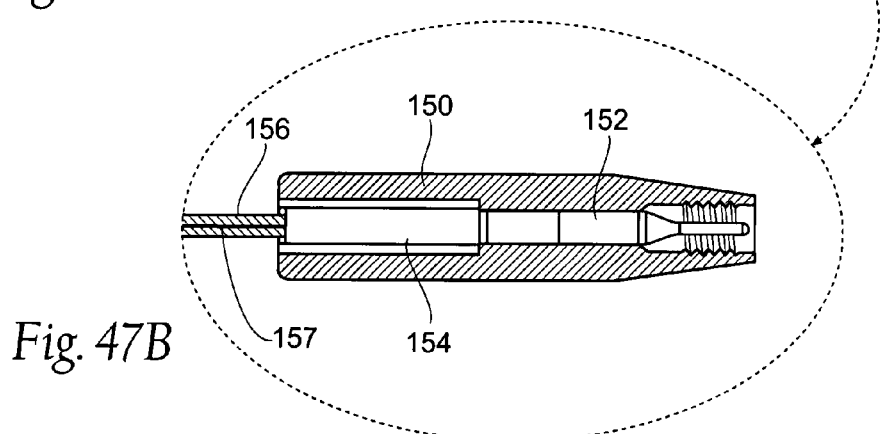
Figure 48A:
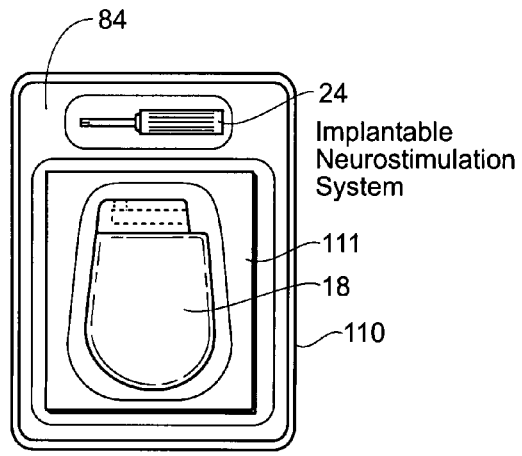
FIGS. 48A to 52 are plane views of kits used in either the single stage implant procedure, or the two-stage implant procedure, or both, to implant the system shown in FIGS. 1A and 1B for use.
Figure 48B:
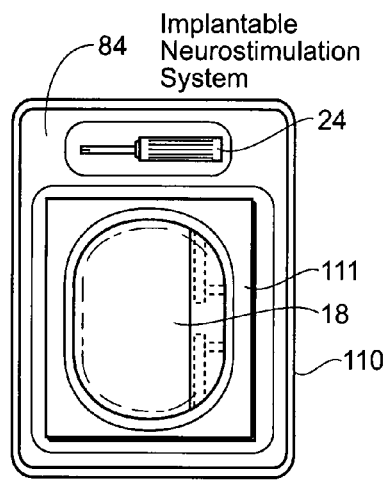
Figure 49:
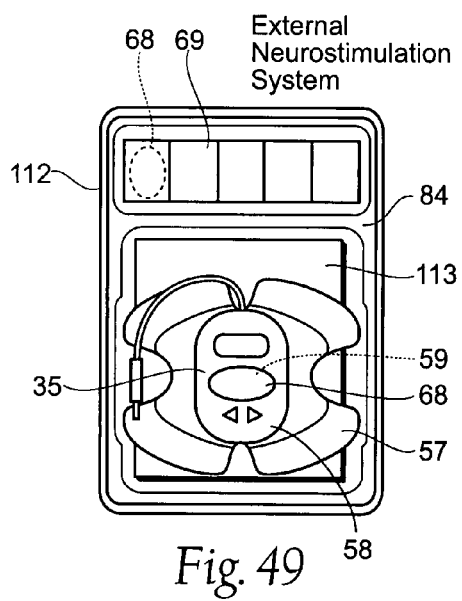
Figure 50:
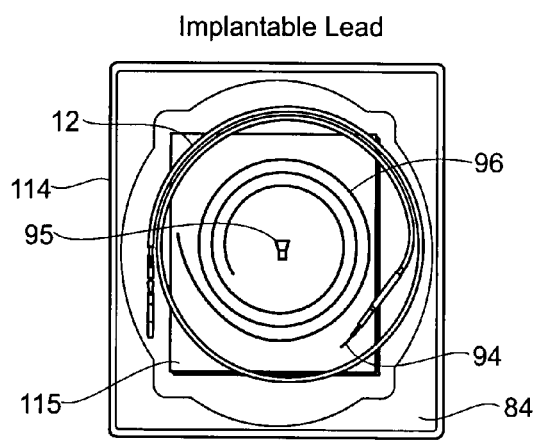
Figure 51:
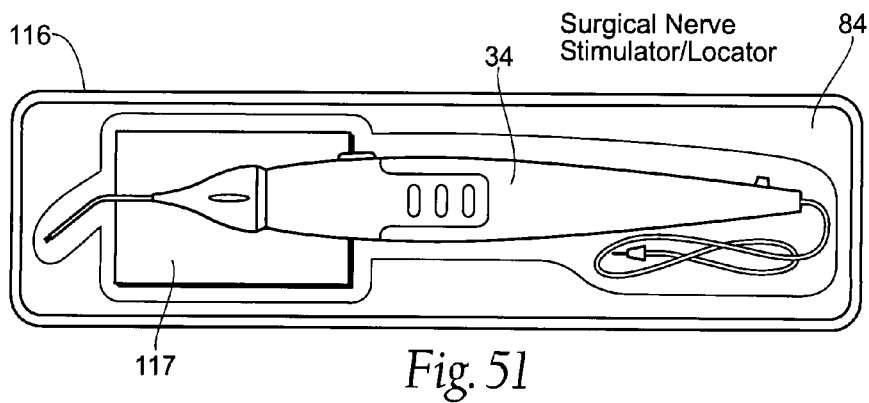
Figure 52:
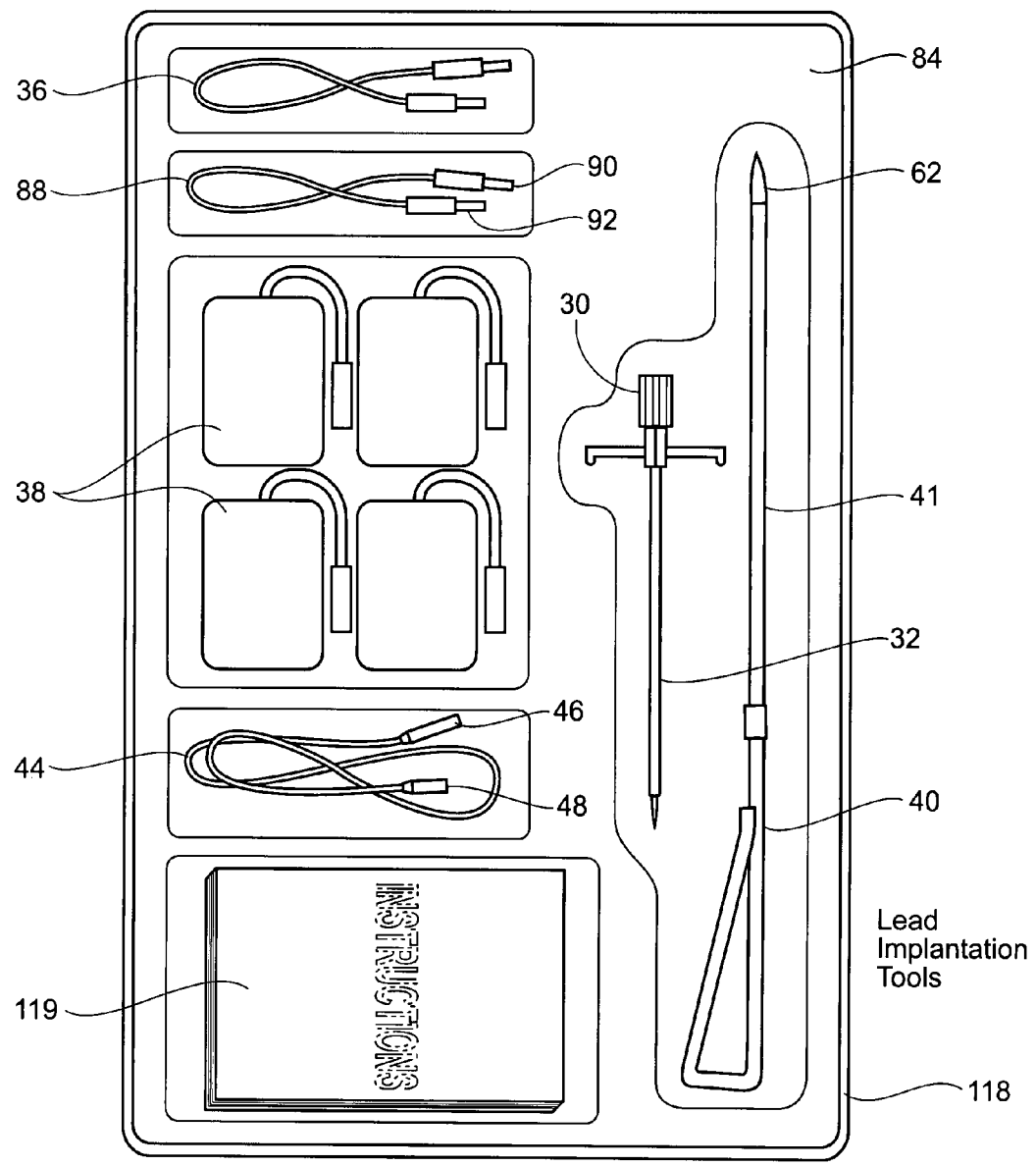

The test screening system 42 also includes the intermediate external extension cable 88 (see FIGS. 47A and 47B). One end of the external extension cable 88 carries a touch proof plug 90 to connect to the external pulse generator 35. The other end of the external extension cable 88 includes a connector 92 to couple to the plug 48 of the percutaneous extension cable 44. This end (i.e., the connector 92) of the external extension cable 88 can also be sized and configured to connect directly to the optional surface patch electrode 38.

The external extension cable 88 also comprises a molded or extruded component 156, which encapsulates one or more stranded or solid wire elements 157, and electrically couples the plug 90 and the receptacle 92. The wire element 157 may be a solid or multifilament wire, and may be constructed of coiled MP35N nickel-cobalt wire or 316L stainless steel wires that have been coated in polyurethane or a fluoropolymer such as perfluoroalkoxy (PFA), or other wire configurations known in the art. The wire element may also be encapsulated in a PVC jacket.

The connector 92 comprises a threaded pin housing 150. Within the threaded pin housing 150 is a crimp style pin 152 for coupling with the socket 132 from the percutaneous extension cable 44. Heat shrink tubing 154 may be used with the deinsulated wire element 157 to couple the extruded component 156 to the pin 152. An adhesive 160 (e.g., silicon), may be used to fill the space between the heat shrink 154 and the pin housing 150. An adhesive may also be used to bond the pin 152 within the housing 150.

V. Kits

As FIGS. 48A through 52 show, the various tools and devices as just described can be consolidated for use in functional kits 110, 112, 114, 116, and 118. FIG. 48B shows an alternative embodiment of pulse generator 18. Each of these kits 110, 112, 114, 116, and 118 can take various forms, and the arrangement and contents of the kits can vary. In the illustrated embodiment, each kit 110, 112, 114, 116, and 118 comprises a sterile, wrapped assembly. The kits may be sterilized using Ethylene Oxide, for example. Each kit 110, 112, 114, 116, and 118 includes an interior tray 84 made, e.g., from die cut cardboard, plastic sheet, or thermo-formed plastic material, which hold the contents. Each kit 110, 112, 114, 116, and 118 also preferably includes directions 111, 113, 115, 117, and 119 for using the contents of the kit to carry out a desired procedure or function.

The directions 111, 113, 115, 117, and 119 can, of course vary. The directions 111, 113, 115, 117, and 119 shall be physically present in the kits, but can also be supplied separately. The directions 111, 113, 115, 117, and 119 can be embodied in separate instruction manuals, or in video or audio tapes, CD's, and DVD's. The instructions 111, 113, 115, 117, and 119 for use can also be available through an internet web page.

As representative examples, implantable neurostimulation kit 110 includes the pulse generator 18 and the torque tool 24 used to positively couple the connector 22 on the lead 12 to the pulse generator 18. As previously describes, instructions 111 for implantation and/or use may also be included.

The external neurostimulation kit 112 includes the external pulse generator 35 and an organizer 69 that can take the form of a daily pill case that includes one or more compartments to hold one or more disposable power sources 68 for each day or period of the prescribed power source replacement regime.

Instructions 113 may also be included. The instructions 113 prescribe use of the external pulse generator 35, including the periodic removal and replacement of the power source 68 with a fresh power source 68. Thus, the instructions 113 prescribe a neurostimulation regime that includes a periodic "powering" or dosing (via a power source replacement) of the external pulse generator 35 in the same fashion that pill-based medication regime directs periodic "dosing" of the medication by taking of a pill. In the context of the external pulse generator 35, a power source 68 becomes the therapeutic equivalent of a pill (i.e., it is part of a user action taken to extend treatment).

The implantable lead kit 114 includes one guide wire 94 pre-inserted into the lead 12 central lumen 13, and an extra guide wire 96 may also be provided. In addition, a guiding funnel 95 may also be provided to aid the insertion of a guide wire into the central lumen 13 of the lead 12. Instructions 115 may also be included.

The surgical nerve stimulator/locator kit 116 includes the test stimulator 34 and instructions for use 117.

The lead implantation tools kit 118 is adapted for carrying out portions of the single stage implant procedure and two-stage implant procedure as previously described. The kit 118 includes the introducer needle 30 inside the sleeve 32, and the tunneling tool 40, including the sleeve 41 and sharp tip 62, and one or more patch electrodes 38 for use on a temporary basis during the screening phase. The percutaneous extension cable 44 for connecting the lead 12 to the external pulse generator 35, connector cable 36 for connecting the test stimulator to the needle 30 and lead 12, and the intermediate external extension cable 88 for connecting the external pulse generator 35 to the percutaneous extension cable 44, are also included.

The instructions 119 for use in the kit 118 may direct the use of these instruments to implant the lead 12 and electrode 16, tunnel the lead 12 and percutaneous extension cable 44, connect the external pulse generator 35, form the subcutaneous pocket, and implant the pulse generator 18 in the subcutaneous pocket in the manner previously described and as shown in FIGS. 9 to 39. The instructions 119 for use can also direct use of the test stimulator 34, the patient controller-charger 26 to operate the implanted pulse generator 18, as well as use of the clinician programmer 52 to program the implanted pulse generator 18.

Other tools as needed, such as the patient controller-charger 26 and the clinical programmer 52, may also be provided in kit form or may be available for use in the surgical suite.

VI. Representative Indications

Due to its technical features, the implant system 10 can be used to provide beneficial results in diverse therapeutic and functional restorations indications.

For example, in the field of urology or urologic dysfunctions, possible indications for use of the implant system includes the treatment of (i) urinary and fecal incontinence; (ii) micturition/retention; (iii) restoration of sexual function; (iv) defecation/constipation; (v) pelvic floor muscle activity; and/or (vi) pelvic pain.

Various features of the invention are set forth in the following claims.

We claim:

1. A method comprising:
creating a first incision near-midline over a pubic symphysis of a patient,
inserting a distal portion of a lead through the first incision, wherein the lead includes the distal portion and a proximal portion, the distal portion including at least one stimulation electrode, wherein the distal portion is inserted through the first incision to position the at least one stimulation electrode at a target site at the pubic symphysis,
creating a second incision remote from the first incision,
tunneling the proximal portion of the lead between the first incision and the second incision,
coupling the lead to a pulse generator,
delivering electrical stimulation from the pulse generator to the patient via the at least one stimulation electrode, wherein the electrical stimulation and target site are selected to bilaterally stimulate the left branch and right branch of a dorsal genital nerve of the patient, and
wherein the at least one stimulation electrode is located such that the electrical stimulation bilaterally stimulates the left branch and right branch of the dorsal genital nerve substantially simultaneously.

2. A method according to claim 1, further including implanting the pulse generator in the second incision.

3. A method according to claim 1, wherein the second incision is located in an anterior pelvic region.

4. A method according to claim 1, wherein the stimulation electrode is sized and configured to be implanted in adipose tissue.

5. A method according to claim 1, wherein the distal portion of the lead includes at least one visual marker.

6. A method according to claim 1, wherein the distal portion of the lead includes a flexible anchoring structure comprising an array of expandable shovel-like paddles.

7. A method according to claim 6, wherein the shovel-like paddles define a scalloped shape.

8. A method according to claim 1, wherein the pulse generator includes a larger end and a smaller end and allows the smaller end of the case to be placed into the second incision first, with the larger end being pushed in last.

9. The method of claim 1, wherein the at least one stimulation electrode comprises a first stimulation electrode, wherein delivering the electrical stimulation from the pulse generator to the patient via the at least one stimulation electrode comprises delivering unipolar electrical stimulation to the patient via the first stimulation electrode.

10. The method of claim 1, wherein the at least one stimulation electrode comprises a first stimulation electrode and a second stimulation electrode, wherein delivering the electrical stimulation from the pulse generator to the patient via the at least one stimulation electrode comprises delivering bipolar electrical stimulation to the patient via the first stimulation electrode and the second stimulation electrode.

11. The method of claim 1, wherein the at least one stimulation electrode comprises a first stimulation electrode and a second stimulation electrode, wherein the lead includes a first lead including the first stimulation electrode and a second lead including the second stimulation electrode, and wherein delivering electrical stimulation from the pulse generator to the patient via the at least one stimulation electrode comprises delivering electrical stimulation from the pulse generator to the patient via at least one of the first stimulation electrode and the second stimulation electrode.

12. The method of claim 1, wherein the at least one stimulation electrode is located in adipose tissue of the patient.

13. The method of claim 1, wherein the pulse generator includes a rechargeable battery and a power receiving coil coupled to the rechargeable battery, wherein the power receiving coil is configured to transcutaneously receive an externally generated radio frequency magnetic field to recharge the rechargeable battery.

14. The method of claim 1, wherein the pulse generator comprises an implantable pulse generator.

15. A method comprising:
implanting a stimulation electrode at a target site at a pubic symphysis of a patient,
coupling the stimulation electrode to a pulse generator configured to generate electrical stimulation, and
activating the pulse generator to deliver the electrical stimulation to the patient via the stimulation electrode, wherein the electrical stimulation and target site are selected to bilaterally stimulate the left branch and right branch of a dorsal genital nerve of the patient.

16. A method according to claim 15, wherein implanting the stimulation electrode at the target site at the pubic symphysis comprises implanting the stimulation electrode at the target site at the pubic symphysis without fluoroscopy.

17. A method according to claim 15, wherein the method is performed without urodynamics.

18. A method according to claim 15, wherein the stimulation electrode further comprises a lead comprising a proximal portion and a distal portion, the distal portion including the stimulation electrode and at least one visual marker, and implanting the stimulation electrode further includes visually observing the lead marker for desired electrode placement.

19. A method according to claim 15, further including requesting feedback from the patient about sensations felt during the implant as a result of applying electrical stimulation.

20. The method of claim 15, wherein delivering the electrical stimulation from the pulse generator to the patient via the stimulation electrode comprises delivering unipolar electrical stimulation to the patient via the stimulation electrode.

21. The method of claim 15, wherein the stimulation electrode comprises a first stimulation electrode, wherein the lead comprises a first lead including the first stimulation electrode, wherein a second lead including a second stimulation electrode is coupled to the pulse generator, and wherein delivering electrical stimulation from the pulse generator to the patient via the stimulation electrode comprises delivering electrical stimulation from the pulse generator to the patient via at least one of the first stimulation electrode and the second stimulation electrode.

22. The method of claim 15, wherein the stimulation electrode is located in adipose tissue of the patient.

23. The method of claim 15, wherein the stimulation electrode is located such that the electrical stimulation stimulates the left branch and right branch of the dorsal genital nerve substantially simultaneously.

24. The method of claim 15, wherein the pulse generator includes a rechargeable battery and a power receiving coil coupled to the rechargeable battery, wherein the power receiving coil is configured to transcutaneously receive an externally generated radio frequency magnetic field to recharge the rechargeable battery.

25. The method of claim 15, wherein the pulse generator comprises an implantable pulse generator.

26. The method of claim 15, wherein delivering electrical stimulation from the pulse generator to the patient via the stimulation electrode comprises delivering unipolar electrical stimulation from the pulse generator to the patient via the stimulation electrode, and wherein the stimulation electrode is located such that the electrical stimulation bilaterally stimulates the left branch and right branch of the dorsal genital nerve substantially simultaneously.

27. The method of claim 15, wherein delivering electrical stimulation from the pulse generator to the patient via the stimulation electrode comprises delivering bipolar electrical stimulation from the pulse generator to the patient via the stimulation electrode and wherein the stimulation electrode is located such that the electrical stimulation bilaterally stimulates the left branch and right branch of the dorsal genital nerve substantially simultaneously.

28. A method comprising:
generating electrical stimulation via a pulse generator; and
delivering the electrical stimulation from the pulse generator to a patient via at least one stimulation electrode located at a target site at a pubic symphysis of the patient, wherein the electrical stimulation and the target site are selected to bilaterally stimulate the left branch and right branch of a dorsal genital nerve of the patient.

29. The method of claim 28, wherein the at least one stimulation electrode comprises a first stimulation electrode, wherein delivering the electrical stimulation from the pulse generator to the patient via the at least one stimulation electrode comprises delivering unipolar electrical stimulation to the patient via the first stimulation electrode.

30. The method of claim 28, wherein the at least one stimulation electrode comprises a first stimulation electrode and a second stimulation electrode, wherein delivering the electrical stimulation from the pulse generator to the patient via the at least one stimulation electrode comprises delivering bipolar electrical stimulation to the patient via the first stimulation electrode and the second stimulation electrode.

31. The method of claim 28, wherein the at least one stimulation electrode comprises a first stimulation electrode and a second stimulation electrode, wherein the lead includes a first lead including the first stimulation electrode and a second lead including the second stimulation electrode, and wherein delivering electrical stimulation from the pulse generator to the patient via the at least one stimulation electrode comprises delivering electrical stimulation from the pulse generator to the patient via at least one of the first stimulation electrode and the second stimulation electrode.

32. The method of claim 28, wherein the at least one stimulation electrode is located in adipose tissue of the patient.

33. The method of claim 28, wherein the at least one stimulation electrode is located such that the electrical stimulation stimulates the left branch and right branch of the dorsal genital nerve substantially simultaneously.

34. The method of claim 28, wherein the implantable pulse generator includes a rechargeable battery and a power receiving coil coupled to the rechargeable battery, and wherein the power receiving coil configured to transcutaneously receive an externally generated radio frequency magnetic field to recharge the rechargeable battery.

35. The method of claim 28, wherein the pulse generator comprises an implantable pulse generator.

36. The method of claim 28, wherein delivering electrical stimulation from the pulse generator to the patient via the at least one stimulation electrode comprises delivering unipolar electrical stimulation from the pulse generator to the patient via the at least one stimulation electrode, and wherein the electrical stimulation stimulates the left branch and right branch of the dorsal genital nerve substantially simultaneously.

37. The method of claim 28, wherein delivering electrical stimulation from the pulse generator to the patient via the at least one stimulation electrode comprises delivering bipolar electrical stimulation from the pulse generator to the patient via the at least one stimulation electrode, and wherein the electrical stimulation stimulates the left branch and right branch of the dorsal genital nerve substantially simultaneously.

* * * * *